US008021356B2

(12) United States Patent
Uchiyama et al.

(10) Patent No.: US 8,021,356 B2
(45) Date of Patent: Sep. 20, 2011

(54) CAPSULE MEDICATION ADMINISTRATION SYSTEM, MEDICATION ADMINISTRATION METHOD USING CAPSULE MEDICATION ADMINISTRATION SYSTEM, CONTROL METHOD FOR CAPSULE MEDICATION ADMINISTRATION SYSTEM

(75) Inventors: Akio Uchiyama, Yokohama (JP); Hironobu Takizawa, Tokyo (JP); Hidetake Segawa, Tokyo (JP); Hironao Kawano, Tokyo (JP)

(73) Assignee: Olympus Corporation, Tokyo (JP)

( * ) Notice: Subject to any disclaimer, the term of this patent is extended or adjusted under 35 U.S.C. 154(b) by 1920 days.

(21) Appl. No.: 10/951,099

(22) Filed: Sep. 27, 2004

(65) Prior Publication Data
US 2005/0148847 A1 Jul. 7, 2005

(30) Foreign Application Priority Data

Sep. 29, 2003 (JP) .................................. 2003-338260
Oct. 29, 2003 (JP) .................................. 2003-368918
May 27, 2004 (JP) .................................. 2004-157590

(51) Int. Cl.
*A61K 9/22* (2006.01)
(52) U.S. Cl. ..................................... 604/890.1; 600/407
(58) Field of Classification Search ............... 604/890.1, 604/891.1, 892.1, 135, 244, 65–67; 600/309, 600/587, 593, 160, 407; 607/40
See application file for complete search history.

(56) References Cited

U.S. PATENT DOCUMENTS

| 5,279,607 A * | 1/1994 | Schentag et al. ............ 604/890.1 |
| 2001/0051766 A1 * | 12/2001 | Gazdzinski .................... 600/309 |
| 2002/0099310 A1 | 7/2002 | Kimchy et al. |

FOREIGN PATENT DOCUMENTS

| JP | 58-81022 | 5/1983 |
| JP | 60-217326 | 10/1985 |
| JP | 5-168680 | 7/1993 |
| JP | 07-111985 | 5/1995 |
| JP | 7085133 B | 9/1995 |
| JP | 7-311834 | 11/1995 |
| JP | 8-131403 | 5/1996 |
| JP | 10-262945 | 10/1998 |
| JP | 2835051 | 10/1998 |
| JP | 2002-186672 | 7/2002 |

(Continued)

OTHER PUBLICATIONS

Japanese Official Action dated Jan. 26, 2010 together with an English language translation.

(Continued)

*Primary Examiner* — Christopher D Koharski
(74) *Attorney, Agent, or Firm* — Scully, Scott, Murphy & Presser, P.C.

(57) ABSTRACT

This capsule medication administration system includes: a capsule type medical device which includes a drug retention section, a drug release section which releases a drug which is retained in the drug retention section, and a communication section which sends and receives signal between the outside; an external device which includes an external communication section which sends and receives signal between the capsule type medical device; a condition input section which inputs conditions for operating the drug release section to the external device; an information acquisition section which acquires information for comparison with conditions which have been inputted by the condition input section; and a comparison section which compares together the information which has been acquired by the information acquisition section and the conditions which have been inputted with the condition input section; and the drug release section is controlled based upon the result of comparison.

52 Claims, 37 Drawing Sheets

FOREIGN PATENT DOCUMENTS

| | | |
|---|---|---|
| JP | 2002-360508 | 12/2002 |
| JP | 2835051 | 12/2002 |
| JP | 2003-38424 | 2/2003 |
| JP | 2004-041709 | 2/2004 |
| WO | WO 00/22975 | 4/2000 |
| WO | WO 02/058531 A2 | 8/2002 |
| WO | WO 03/001966 A2 | 1/2003 |

OTHER PUBLICATIONS

Japanese Office Action dated Mar. 1, 2011 together with an English language translation.

Korean Office Action dated Apr. 8, 2011 together with English translation.

* cited by examiner

TREATMENT TOOL FOR ATTACHING CLIP · CLIP · ALIMENTARY CANAL LUMEN WALL

CLIP · ALIMENTARY CANAL LUMEN WALL

CAPSULE MEDICATION ADMINISTRATION SYSTEM, MEDICATION ADMINISTRATION METHOD USING CAPSULE MEDICATION ADMINISTRATION SYSTEM, CONTROL METHOD FOR CAPSULE MEDICATION ADMINISTRATION SYSTEM

BACKGROUND OF THE INVENTION

1. Field of the Invention

The present invention relates to a capsule medication administration system which administers medication to a diseased part, such as a superficial disorder or the like, within the living body.

The present invention relates to a medication administration method and a control method for capsule medication administration system, which utilize a capsule medication administration system which can easily and moreover directly approach a target site, such as a superficial disorder or the like, within the living body.

Priority is claimed on Japanese Patent Application No. 2004-157590 filed on 27 May 2004, Japanese Patent Application No. 2003-338260 filed on 29 Sep. 2003, and Japanese Patent Application No. 2003-368918 filed on 29 Oct. 2003, the contents of which are incorporated herein by reference.

2. Description of Related Art

Nowadays, as device for administering a drug to a patient more safely and also more effectively, while suppressing excessive administration and side effects, attention is being directed towards drug delivery systems (DDS).

Such a drug delivery system is a system which uses a drug more effectively by regulating the biological activity of the medicament and its side effects, targeting the diseased part, controlling the release of the drug (controlled release), improving the absorption of the drug, regulating the chemical stability and the metabolic activity and so on of the drug, and causing the drug to act upon a superficial disorder within the living body in the required amount and for just the required period of time. With such a drug delivery system, the technique for taking advantage of it is different according to the type of the disorder; for example, if the superficial disorder which is the diseased part is a malignant tumor, a technique is obtained of targeting and controlled release and the like.

Furthermore, for specifying the above described type of superficial disorder, it is conventional for a physician or the like to specify the diseased part based upon information which has been obtained by some type of diagnostic device, such as, for example, an X-ray CT device, an MRI device (a magnetic resonance image imaging device) a nuclear medical device (a gamma camera, a SPECT or a PET), an ultrasonic wave diagnostic device, an endoscope device, or the like.

On the other hand, as a device for, without imposing a burden upon the patient, checking for a superficial disorder as above described or upon his state of health, there is a known capsule type medical device which is orally ingested to within the living body. With this kind of capsule type medical device, various types of information may be provided; for example, it is known to take photographs at random of various parts within the living body, to take samples or the like from within the living body, to release a drug, and the like. As one such device, there is known a capsule endoscope which performs formation of an image after releasing a foaming agent at a predetermined position (the large intestine) within the living body and thereby distending the luminar portion within his body (for example, refer to paragraphs 0006 through 0049 and to FIG. 1 through FIG. 5 of Japanese Unexamined Patent Application, First Publication No. 2003-38424).

The above described capsule endoscope is provided with a capsule shaped body which has a hemispherical shaped and transparent member at its one end surface and a hemispherical mesh member at its other end surface.

Furthermore, on the inside of the transparent member, i.e. in the interior of the capsule body, there are provided a LED which emits light for illumination to the interior of the living body, and an image formation optical system which forms an image of the interior of the living body.

Yet further, a pH sensor is provided to the capsule body so as to be exposed upon the outer surface thereof. The pH value which has been detected by this pH sensor is sent to a control processing circuit, and, when it has been decided from the change of the pH value that the capsule has arrived at the large intestine, this is transmitted from a transmission antenna towards the outside of the living body. Even further, as well, the image data which has been formed into an image by the above described image formation optical system is transmitted from the transmission antenna towards the outside of the living body, after having been subjected to predetermined processing. Moreover, a plurality of micro capsules are housed on the inside of the mesh member, and are broken down by emission of ultrasound, and a foaming agent is stored in the insides of these micro capsules which generates a gas by reaction with water.

When a check is to be performed by using this capsule endoscope, the patient first swallows the capsule endoscope so as to ingest it to within his body. The capsule endoscope which has thus been ingested to within the living body shifts within his digestive organs while detecting the pH value within his body by using the pH sensor. When the capsule endoscope arrives at the large intestine, the control processing circuit decides, based upon change of the pH value which has been detected by the pH sensor, that the capsule endoscope has arrived at the large intestine, and issues a notification to that effect to the exterior of the living body from the transmission antenna. When medical staff or the like on the outside of the living body have received this signal which has been transmitted, the medical staff or the like emit an ultrasonic wave towards the living body using an ultrasonic wave generator. When the ultrasonic wave is thus emitted, since it breaks down the micro capsules, accordingly the foaming agent inside them is released within the large intestine through the mesh member.

And this foaming agent reacts with the water component within the large intestine and generates gas, thus distending the interior of the large intestine. Due to this, it becomes possible to form an image using the image formation optical system over a wide range of the interior of the large intestine which has thus been distended.

In this manner, the above described capsule endoscope is one with is equipped with the above described functions of targeting and controlled release, i.e. of releasing the foaming agent from the micro capsules at a predetermined position (the large intestine) in the living body. In particular, new attention is being paid to this kind of capsule type medical device as one device for implementing the above described drug delivery system, since it can simply and conveniently be ingested to the interior of the living body.

SUMMARY OF THE INVENTION

The present invention proposes a capsule medication administration system, including: a capsule type medical device which includes a drug retention section, a drug release section which releases a drug which is retained in the drug retention section, and a communication section which transmits signal to the outside and receives from thereof; an external device which includes an external communication section which transmits signal to the capsule type medical device and receives from it; a condition input section which inputs conditions for causing the operation of the drug release section to the external device; an information acquisition section which acquires information for comparison with conditions which have been inputted with the condition input section; and a comparison section which compares together the information which has been acquired by the information acquisition section and the conditions which have been inputted with the condition input section; wherein a medication position specification device which supplies data for deciding upon a site for which medication is required is connected to the condition input section; and the drug release section is controlled based upon the result of comparison by the comparison section.

With the present invention, it is desirable for the comparison section to be provided to the external device.

With the present invention, it is desirable for the capsule type medical device to include, within a casing, an observation section which acquires in-vivo information, and a control section which causes the observation section to operate when an in-vivo information acquisition signal has been received by the communication section; for the external communication section to be equipped with the function of transmitting the in-vivo information acquisition signal towards the capsule type medical device, based upon the comparison decision result of the comparison section; for the communication section to be equipped with the function of receiving the in-vivo information acquisition signal; for the communication section to be equipped with the function of transmitting the in-vivo information which has been acquired by the observation section to outside his body; for the external communication section to be equipped with the function of receiving the in-vivo information; and for the comparison section to be equipped with the function of, along with deciding whether or not to administer medication based upon the in-vivo information which has been received by the external communication section, also, when it has decided to administer medication, controlling the external communication section so as to transmit a release signal towards the capsule type medical device.

With the present invention, it is desirable for the medication position specification device to be an endoscope device which includes an insertion section which, along with being inserted within the living body, also includes an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto; for the information acquisition section of the capsule type medical device to include an image formation section which forms images of the interior of the living body; and for the communication section to transmit the positional information itself, based upon the period of time that has elapsed from oral ingestion to within the living body, and the image information which has been imaged by the image formation section which corresponds thereto.

With the present invention, it is desirable for the specification device to be an endoscope device which includes an insertion section which, along with being inserted within the living body, also includes an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto; for the information acquisition section of the capsule type medical device to include an image formation section which forms images of the interior of the living body, and a measurement section which measures the moving distance within the living body; and for the communication section to transmit the positional information itself, based upon the moving distance which has been measured by the measurement section, and the image information which has been imaged by the image formation section which corresponds thereto.

With the present invention, it is desirable for the comparison section to be provided to the capsule type medical device.

With the present invention, it is desirable for the specification device to be an endoscope device which includes an insertion section which, along with being inserted within the living body, also includes an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto; for the information acquisition section of the capsule type medical device to include an image formation section which forms images of the interior of the living body; and for a detection section which detects its own the positional information, based upon the period of time that has elapsed from oral ingestion to within the living body, and the image information which has been imaged by the image formation section which corresponds thereto.

With the present invention, it is desirable for the specification device to be an endoscope device which includes an insertion section which, along with being inserted within the living body, also includes an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto; for the information acquisition section of the capsule type medical device to include an image formation section which forms images of the interior of the living body, and a measurement section which measures the moving distance within the living body; and for a detection section which detects its own the positional information, based upon the moving distance which has been measured by the measurement section, and the image information which has been imaged by the image formation section which corresponds thereto.

With the present invention, it is desirable for the information acquisition section of the capsule type medical device to include a sensor which, while shifting within the living body, measures the hardness of the living tissue with which it is in contact; and for the comparison section, in addition to its own positional information and positional information for the diseased part, also to make its decision by comparing whether or not it has arrived at the position of the diseased part, based upon the hardness of the living tissue which has been measured by the sensor.

With the present invention, it is desirable for there to be further included the capsule type medical device which is orally ingested within the living body, and a specification device which specifies a diseased part for which medication is required and the position of the diseased part; for the specification device to include a marking device which makes a mark at the position of the diseased part which has been specified; and for the information acquisition section of the capsule type medical device to include a marker detection section which detects the marker, and there is included a release control device which causes the drug release section to operate when the marker has been detected by the marker detection section.

With the present invention, it is desirable for the specification device to be an endoscope device which includes an insertion section which is inserted within the living body; and for the marking device to make the marker at the diseased part by using a tip end section of the insertion section.

With the present invention, it is desirable for the marking device to be an emission device which emits an ultrasonic wave or an electromagnetic wave at the diseased part which passes through the living body and has directivity from outside the living body towards the interior thereof; and for the marker detection section to detect the ultrasonic wave or the electromagnetic wave.

With the present invention, it is desirable for there to be further included a traversed distance calculation device which obtains the distance traversed within the lumen from the information of the medication position specification device, and for the information acquisition section to be a moving distance detection device.

With the present invention, it is desirable for the condition input section to simplify or to approximate the information from the medication position specification device.

With the present invention, it is desirable for the medication position specification device to include an external in-vivo information acquisition device which acquires information about the interior of the living body from outside his body.

With the present invention, it is desirable for the medical position specification device to include an external marker to the living body for detecting the relative position of the site within the living body and the site external to the living body.

With the present invention, it is desirable for the external in-vivo information acquisition device to be a transilluminated image acquisition device which acquires a transilluminated image of the interior of the living body from outside the living body.

With the present invention, it is desirable for the transilluminated image acquisition device to be an X-ray device.

With the present invention, it is desirable for the transilluminated image acquisition device to be a PET device.

With the present invention, it is desirable for the external in-vivo information acquisition device to be a tomographic image acquisition device which acquires a tomographic image of the interior of the living body from outside the living body.

With the present invention, it is desirable for the tomographic image acquisition device to be capable of acquiring a three dimensional image of the interior of the living body based upon a plurality of tomographic images.

With the present invention, it is desirable for the tomographic image acquisition device to be a CT device.

With the present invention, it is desirable for the tomographic image acquisition device to be an MRI device.

With the present invention, it is desirable for the tomographic image acquisition device to be an ultrasonic tomopraphic device.

With the present invention, it is desirable for the medication position specification device to have an in-body insertion section which is inserted into the living body.

With the present invention, it is desirable for the in-body insertion section to be included an in-body indicator device which places an indicator within the living body.

With the present invention, it is desirable for the in-body indicator device to be an indicator liquid indwell device which discharges or injects?? an indicator liquid which becomes an indicator in the living body.

With the present invention, it is desirable for the indicator liquid to be a dye or a fluorescent dye.

With the present invention, it is desirable for the indicator liquid to be a radioactive substance or a magnetic substance.

With the present invention, it is desirable for the indicator to be an indicator which has the difference of reflectivity ratio with respect to living tissue within the coelom.

With the present invention, it is desirable for the medication position specification device to be an endoscope device which has an in-body insertion section.

With the present invention, it is desirable for the endoscope device to be provided an insertion amount detection section which detects the insertion distance of the in-body insertion section to within the living body.

With the present invention, it is desirable for the endoscope device to be provided an in-body indicator device which places an indicator within the living body, and the indicator is a clip or a stent made from metal.

With the present invention, it is desirable for the in-body insertion section to be a capsule type medical device for acquiring in-vivo information, comprises an in-vivo information acquisition device which acquires information about the interior of the living body.

With the present invention, it is desirable for the capsule type medical device for acquiring in-vivo information to be provided a moving distance calculation device which calculates the moving distance, based upon the variation along with the passage of time of the surface information of the living body lumen wall which has been acquired by the in-vivo information acquisition device.

With the present invention, it is desirable for the capsule type medical device for acquiring in-vivo information to include, within a capsule shaped casing, a measurement device for observation which measures the moving distance within the living body, a memory which records the moving distance which has been measured by the measurement device for observation and the in-vivo information which has been acquired by the in-vivo information acquisition device with a correspondence being established between them, and a specification device which specifies the body part for which medication is required and the moving distance to the diseased part, based upon the in-vivo information which has been recorded in the memory; and for the capsule type medical device for medication which is equipped with the drug retention section and the drug release section to include, within a capsule shaped casing, a measurement device for medication which measures the moving distance within the living body, a decision device which decides whether or not the moving distance which has been measured by the measurement device for medication is the moving distance which has been specified by the specification device, and a control device which causes the drug release section to operate, when the decision device has decided that it is the moving distance which has been specified.

With the present invention, it is desirable for the capsule type medical device for acquiring in-vivo information to include, within a capsule shaped casing, a measurement device for observation which measures the moving distance within the living body, and a transmission device which transmits the moving distance which has been measured by the measurement device for observation and the in-vivo information which has been acquired by the in-vivo information acquisition device towards the external device with a correspondence being established between them; for the external device to include a specification device which acquires in-vivo information by the exterior communication device, and specifies the diseased part for which medication is required, and the moving distance to the diseased part, based upon the in-vivo information which has been received; and for the capsule type medical device for medication which is equipped with the drug retention section and the drug release section to include, within a capsule shaped casing, a measurement device for medication which measures the moving distance within the living body, a decision device which decides whether or not the moving distance which has been measured by the measurement device for medication is the moving distance which has been specified by the specification device, and a control device which causes the drug release section to operate, when the decision device has decided that it is the moving distance which has been specified.

With the present invention, it is desirable for the capsule type medical device for acquiring in-vivo information to include, within a capsule shaped casing, a position transmission device which transmits positional information for itself to outside the living body; for the external device to include a position detection device which detects the position information which has been transmitted by the position communication device, specification device which specifies the diseased part for which medication is required, the moving distance to the diseased part, based upon the in-vivo information which has been received by the external communication section, and the positional information which has been detected by the position detection device; and for the capsule type medical device for medication which is equipped with the drug retention section and the drug release section to include, within a capsule shaped casing, a measurement device for medication which measures the moving distance within the living body, a decision device which decides whether or not the moving distance which has been measured by the measurement device for medication is the moving distance which has been specified by the specification device, and a control device which causes the drug release section to operate, when the decision device has decided that it is the moving distance which has been specified.

With the present invention, it is desirable for the capsule type medical device for acquiring in-vivo information to be provided a measurement device for observation which measures the moving distance within the living body.

With the present invention, it is desirable for the capsule type medical device for acquiring in-vivo information to include, as the in-vivo information acquisition device, an image formation device which forms an image of the interior of the living body, and an illumination device which illuminates the interior of the living body.

With the present invention, it is desirable for the capsule type medical device for acquiring in-vivo information to include, as the in-vivo information acquisition device, a blood sensor which detects hemorrhage within the living body.

With the present invention, it is desirable for the capsule type medical device for acquiring in-vivo information to include an in-body indicator device which places an indicator within the living body.

With the present invention, it is desirable for the in-body indicator device to place the indicator within the living body intermittently.

With the present invention, it is desirable for the in-body indicator device to discharge or to inject the indicator at constant time intervals.

With the present invention, it is desirable for the in-body indicator device to discharge or to inject the indicator at constant distance intervals.

With the present invention, it is desirable for there to be included a capsule type medical device which includes an indicator detection device which detects an indicator which is left within the coelom, and a release control device which controls the drug release section based upon the information of the indicator detection device.

With the present invention, it is desirable for the capsule type medical device for acquiring in-vivo information to include an external communication section which transmits to the exterior in-vivo information which has been acquired by the in-vivo information acquisition device, and movement information of the in-body indicator device; and for the capsule medication administration system includes an external device which receives the information which has been transmitted to the exterior by the external communication section.

With the present invention, it is desirable for the capsule medication administration system to include: within a capsule shaped casing which is orally ingested to within the living body, a drug retention section which retains a drug; a drug release section which releases the drug which has been retained in the drug retention section; a release control device which causes the operation of the drug release section; and an indicator detection device which detects an indicator which indicates a drug release position; and for the indicator detection device to be a device which detects a plurality of markings which have been made within the living body; for the release control device to include a memory which stores the specified marking in advance as a marking number; and for the release device to be caused to operate by counting the markings which have been detected by the detection device, when this count agrees with the number which is stored in the memory.

With the present invention, it is desirable for the capsule medication administration system to include: a capsule shaped casing which is orally ingested within the living body; a transmission device which transmits the in-vivo information which has been acquired by the in-vivo information acquisition device and the indicator which has been left within the coelom by the in-body indicator device to the exterior of the casing; and an information processing section which establishes a correspondence between the in-vivo information which has been acquired by the in-vivo information acquisition device and information about the indicator which has been left within the living body by the marking device.

With the present invention, it is desirable for the capsule medication administration system to include a storage device which stores information which has been processed by the information processing section.

The present invention proposes a medication administration method using a capsule medication administration system, comprising the steps of: supplying data for deciding upon a site for which medication is required from a medication position specification device to a condition input section;

inputting conditions for causing the operation of a drug release section via the condition input section to an external device; comparing the conditions for causing the operation of the drug release section which have been inputted to the external device, and information which has been acquired by an information acquisition section, using a comparison section; transmitting the result of comparison by the comparison section to the capsule type medical device via an external communication section of the external device and a communication section of the capsule type medical device; and releasing a drug which has been retained by the drug retention section from the drug release section.

With the present invention, it is desirable for information about the interior of the living body to be acquired from outside the living body by an external in-vivo information acquisition device which is equipped with the medication position specification device.

With the present invention, it is desirable for an in-body insertion section which is equipped with the medication position specification device to be inserted into the living body.

With the present invention, it is desirable for an indicator to be placed within the living body by an in-body indicator device which is equipped with the in-body insertion section.

With the present invention, it is desirable for an endoscope device which has an in-body insertion section to be used as the medication position specification device.

With the present invention, it is desirable for, along with acquiring in-vivo information by using the endoscope device, an indicator to be affixed within the living body by using the endoscope device.

With the present invention, it is desirable for a capsule type medical device which includes an in-vivo information acquisition device which has an in-body insertion section to be used as the medication position specification device.

The present invention proposes a control method for capsule medication administration system, including: a step of obtaining in-vivo information; a step of determining a medication position within the living body; a step of appending an indicator near the medication position; a step of inserting within the coelom a capsule for medication which includes a device for detecting the indicator, a drug retention section, a drug release section, and a release control device; a step of detecting the indicator; and a step of performing control of the drug release section.

The present invention proposes a control method for capsule medication administration system, including: a step of obtaining in-vivo information; a step of leaving an indicator within the living body; a step of establishing a correspondence between in-vivo information which has been obtained by the step of obtaining in-vivo information, and the fact that the step of leaving an indicator within the living body has been performed, and recording the same as in-vivo information; a step of determining a medication position based upon the in-vivo information; a step of setting the medication position into a capsule for medication which includes a device for detecting the indicator, a drug retention section, a drug release section, and a release control device; a step of inserting the capsule for medication within the coelom; a step of detecting the indicator; a step of detecting the medication position; and a step of performing control of the drug release section.

DETAILED DESCRIPTION OF THE INVENTION

In the following, the first embodiment of the capsule medication administration system of the present invention will be explained with reference to FIG. 1 through FIG. 6.

Figure 1:
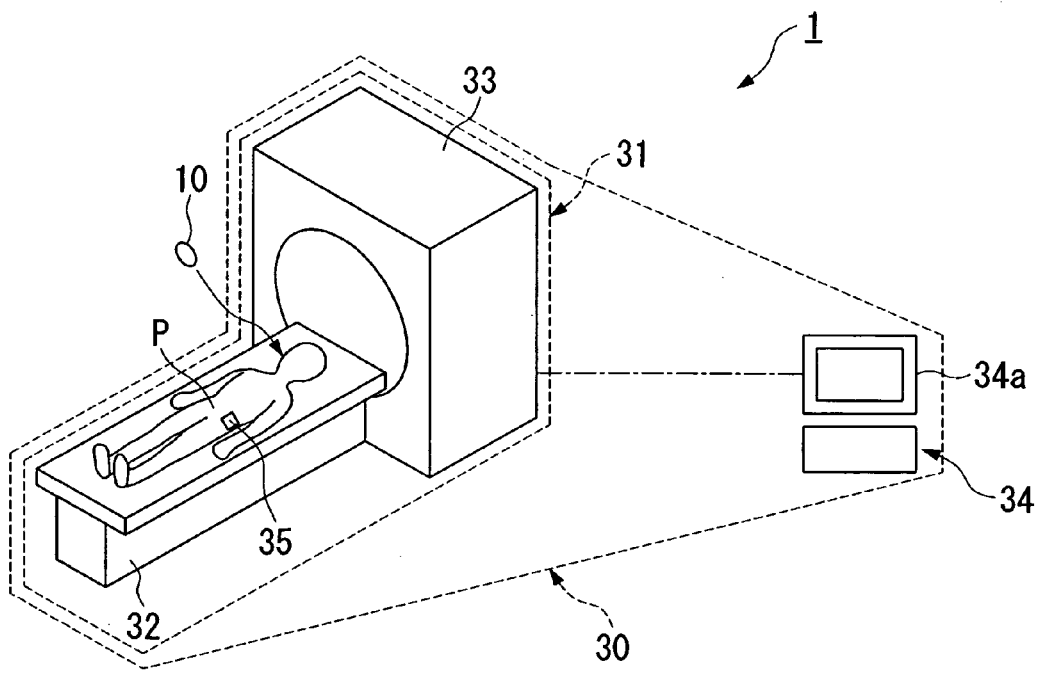
FIG. 1 is a schematic figure showing a first embodiment of the capsule medication administration system according to the present invention.
Figure 2:
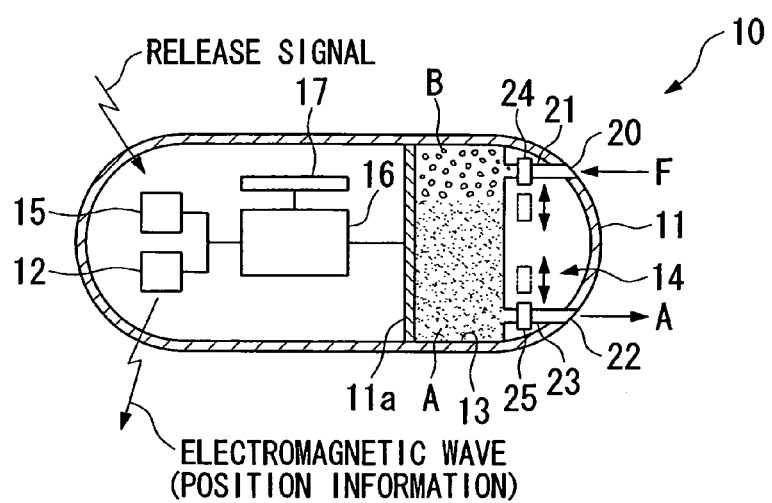
FIG. 2 is a sectional view showing a capsule for medication which is used in the capsule medication administration system shown in FIG. 1.

The capsule medication administration system 1 of this embodiment, as shown in FIG. 1 and FIG. 2, includes a capsule for medication (a capsule type medical device) 10 and a unit 30 external to the living body. The capsule for medication 10 includes an information transmission section 12 which, after having been orally ingested to within the living body, transmits information about its own position within the living body to outside of the living body. The unit 30 external to the living body includes a specification device 31 (a medication position specification device) which specifies a diseased part X for which medication is required (refer to FIG. 3), and the position of this diseased part X. In this embodiment, an X-ray computer tomography device (hereinafter termed an X-ray CT device) is used as the specification device 31. It should be understood that the specification device 31 is not limited to being an X-ray CT device as in this embodiment; it would also be possible to employ various other types of medical diagnostic device, such as a MRI scanner, a PET scanner, an X-ray observation device, an ultrasonic wave observation device, or the like.

As shown in FIG. 2, the capsule for medication 10 includes, within a capsule shaped casing 11, an information transmission section 12, a reservoir 13 (a drug retention section) which retains a drug A, a release section (a drug release section) 14 which releases the drug A which has been retained in the reservoir 13, a reception section 15 which receives a release signal which has been transmitted from the unit 30 external to the living body, a control section 16 which causes the release section 14 to operate when the reception section 15 has received the release signal, and a battery 17 which supplies electrical power to these various structural components. The information communication section 12 and the reception section 15 constitute a communication section.

The casing 11 is formed from plastic or the like so as enclose its interior tightly, and, at one end of its interior, the above described reservoir 13 is provided as surrounded by a wall portion 11a and the inner peripheral surface of the casing 11. A body fluid intake conduit 21 and a drug release conduit 23 are connected to the reservoir 13. This body fluid intake conduit 21 includes a body fluid intake aperture 20 which opens to the outer surface of the casing 11, while the drug release conduit 23 includes a drug release aperture 22 which opens to the outer surface of the casing 11. The body fluid intake aperture 20 and the drug release aperture 22 are formed in plurality around the perimeter of the one end of the casing 11. To the body fluid intake conduit 21 there is provided an opening and closing valve 24 which opens and closes the conduit by approaching towards and moving away from the conduit. To the drug release conduit 23 as well, there is also provided an opening and closing valve 25 of the same sort. The body fluid intake aperture 20, the body fluid intake conduit 21, the drug release aperture 22, the drug release conduit 23, and the two opening and closing valves 24 and 25 constitute the above described release section 14.

Into the interior of the reservoir 13, in addition to the drug A, there is charged a chemical B, such as a foaming agent or the like, which is expandable, i.e. which has the characteristic of reacting and expanding when it comes into contact with a water component. The drug A is stored on the side of the drug release conduit 23, while the expandable chemical B is stored on the side of the body fluid intake conduit 21, so as to be adjacent to the drug A. When the opening and closing valves 24 and 25 are opened, body fluid F is taken in from the exterior of the casing 11 into the interior of the reservoir 13 and reacts with the expandable chemical B, and the drug A is released to the exterior of the casing 11 due to the elevation of the pressure within the reservoir 13 which is caused by the expansion of the expandable chemical B.

It should be understood that, when storing the drug A in the interior of the reservoir 13, first the expandable chemical B is put in, and, after this it is possible to store the drug A at high density in the interior of the reservoir 13 by inserting the drug A from the drug release aperture 22 and causing the expandable chemical B to spill over from the body fluid intake aperture 20.

The control section 16 receives the release signal and operates the opening and closing valves 24 and 25. It should be understood that, in its initial state, each of these opening and closing valves 24 and 25 is arranged in a position to close off its one of the conduits 21 and 23.

The information transmission section 12 transmits electromagnetic waves which include information about the position of the capsule for medication 10 to the exterior of the living body.

As shown in FIG. 1, the specification device 31 includes a cot 32, a detector 33, and a personal computer 34 (hereinafter termed a PC). The cot 32 can be shifted forwards and backwards while in its state of carrying the patient P. By emitting X-rays towards the patient P who is shifting while being carried upon the cot 32, and by also detecting the X-rays which are emitted, the detector 33 acquires image information of the patient P such as tomographic images and the like. It should be understood that, not only may the detector 33 acquire tomographic images of the patient P, but it may also acquire solid three dimensional images.

The PC 34, along with performing predetermined procedures such as image processing upon the image information which has been acquired by the detector 33, also is equipped with the function of overall control of the shifting of the cot 32 and the operation of the detector 33. Furthermore, the PC 34 includes a display monitor 34a which displays images after the predetermined processing has been performed. A physician or the like can perform diagnosis, and can specify the diseased part X, based upon the images which are displayed upon the display monitor 34a.

Figure 3:
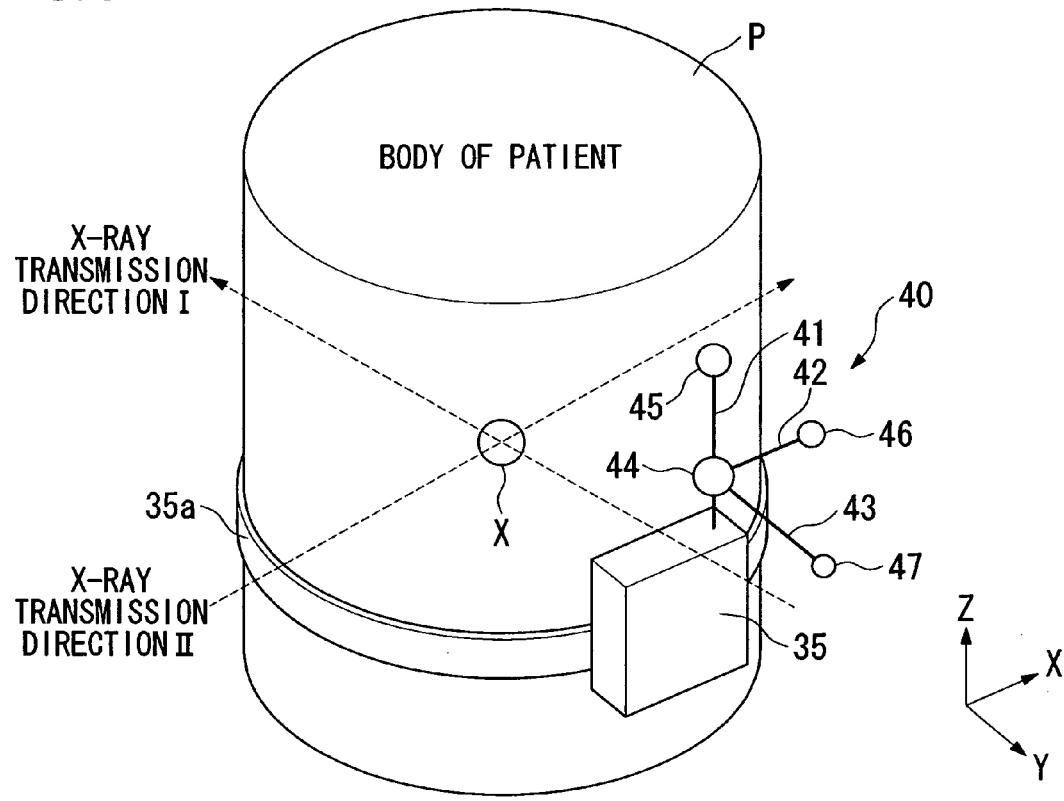
FIG. 3 is a perspective view showing a situation in which a three dimensional marker has been attached to a device external to the living body which is used in the capsule medication administration system shown in FIG. 1, and it has been put on by the patient.

As shown in FIG. 1 and FIG. 3, the unit 30 external to the living body includes a device external to the living body (an external device) 35 which is put onto the exterior of the living body P. This external device 35 is attached to a belt 35a or the like, and is put onto the exterior of the living body P by this belt 35a being put on by the patient P. A three dimensional marker 40, which is attachable and detachable, is attached to the exterior of this external device 35 (it should be understood that this three dimensional marker 40 may also be disposed in the interior of the external device 35). This three dimensional marker 40 includes three axis members, in other words a Z-axis member 41, an X-axis member 42, and a Y-axis member 43, and four ball shaped bodies 44, 45, 46, and 47. These four ball shaped bodies 44, 45, 46, and 47 are made from a substance which has non-radioparency, and the size of the diameter of each of them is different.

The Z-axis member 41 is provided in the direction along the patient P. The ball shaped body 44 is provided at the approximate center of the Z-axis member 41, and at the tip end of the Z-axis member 41, there is provided the ball shaped body 45, whose diameter is smaller than that of the ball shaped body 44. The X-axis member 42 is connected to the ball shaped body 44, and is oriented in a direction which is orthogonal to the Z-axis member 41. At the tip end of the X-axis member 42, there is provided the ball shaped body 46, whose diameter is smaller than that of the ball shaped body 45. Moreover, the Y-axis member 43 is connected to the ball shaped body 44, and is oriented in a direction which is orthogonal to both the Z-axis member 41 and the X-axis member 42. At the tip end of the Y-axis member 43, there is provided the ball shaped body 47, whose diameter is smaller than that of the ball shaped body 46.

When the diseased part X is being specified using the specification device 31, this three dimensional marker 40 is attached to the external device 35. After a physician or the like has specified the diseased part X by using the specification device 31, he is able to specify the position of this diseased part X, based upon position correlation of the diseased part X and the ball shaped bodies 44, 45, and 46 of the three dimensional marker 40.

Furthermore, the three dimensional marker 40 is equipped with the function of acting as a condition input section for inputting conditions for operation of the release section 14 of the capsule for medication 10 to the external device 35. The operation of specifying the position of the diseased part X will be explained in detail hereinafter.

Figure 4:
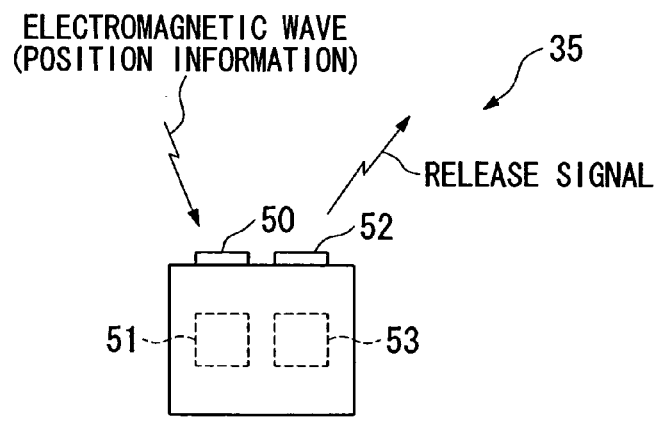
FIG. 4 is a structural view of the device external to the living body shown in FIG. 3.

As shown in FIG. 4, the external device 35 is provided with a reception section 50 external to the living body, a decision section 51, and a transmission section 52 external to the living body. The reception section 50 external to the living body receives electromagnetic waves which include positional information which has been transmitted from the information transmission section 12 of the capsule for medication 10. The decision section 51 decides whether or not the capsule for medication 10 has arrived at the position of the diseased part X, based upon the direction of reception of the electromagnetic waves which have been received by the reception section 50 external to the living body and the level of these electromagnetic waves, and upon the positional information for the diseased part X which has been specified by the specification device 31. The transmission section 52 external to the living body transmits a release signal towards the capsule for medication 10, when it has been decided that the capsule for medication 10 has arrived at the position of the diseased part X.

The reception section 50 external to the living body and the transmission section 52 external to the living body together constitute an external communication section which performs transmission and receipt of various signals to and from the capsule for medication 10. The decision section 51, along with functioning as an information acquisition section which acquires information for comparison of conditions inputted from the condition input section, also functions as a comparison section which compares the information which has been acquired with the conditions which have been inputted by the condition input section.

Moreover, the external device 35 includes a memory 53 which records the positional information for the diseased part X which has been specified by the specification device 31. It is possible to input the positional information for the diseased part X with the PC 34 into this memory 53. Therefore, it is possible for the decision section 51 to make the above described decision, based upon the positional information for the diseased part X which is stored in the memory 53.

Figure 5:
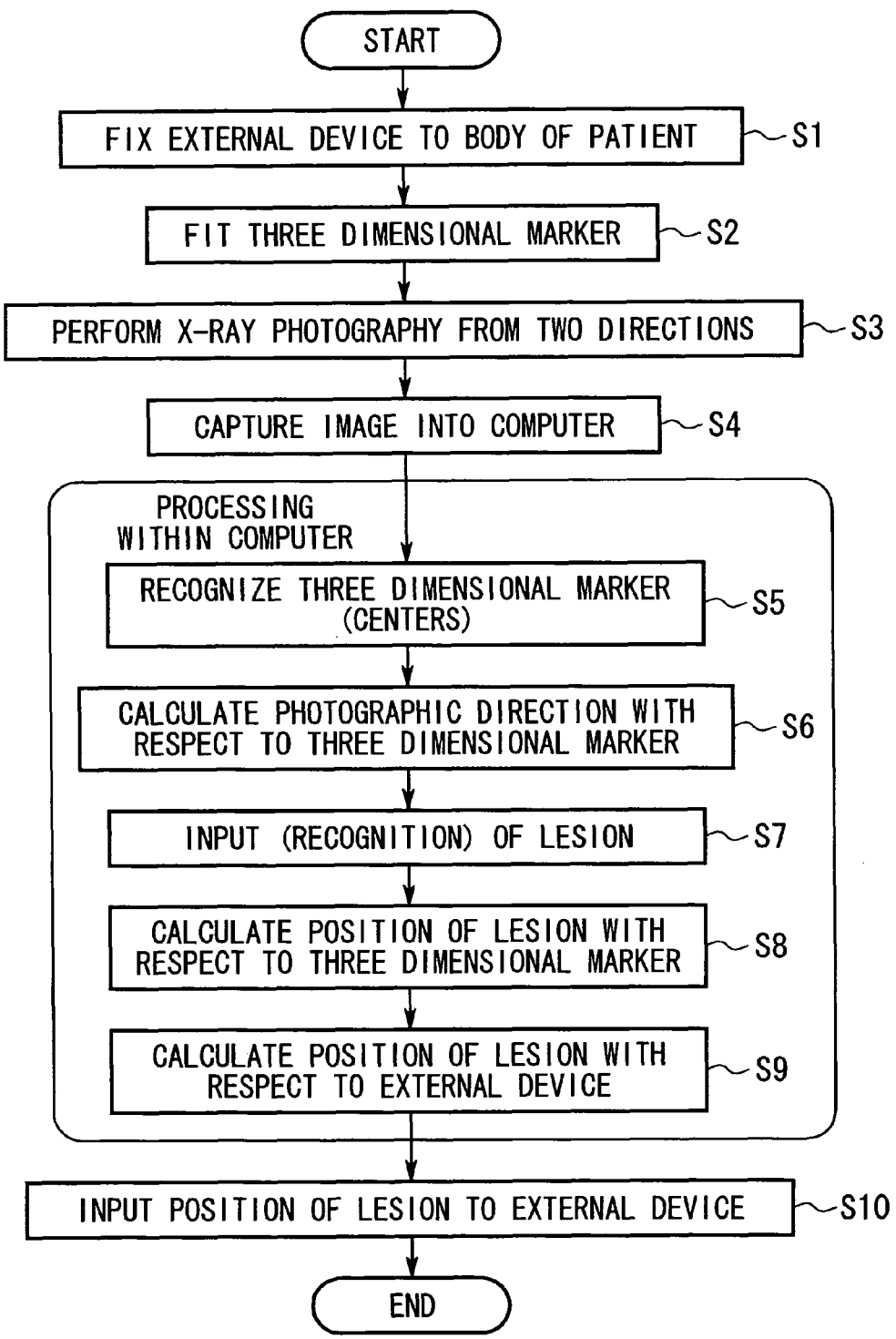
FIG. 5 is a flow chart for the case of specification of a diseased part by a specification device of the capsule medication administration system, and for specification of the position of the diseased part.
Figure 6:
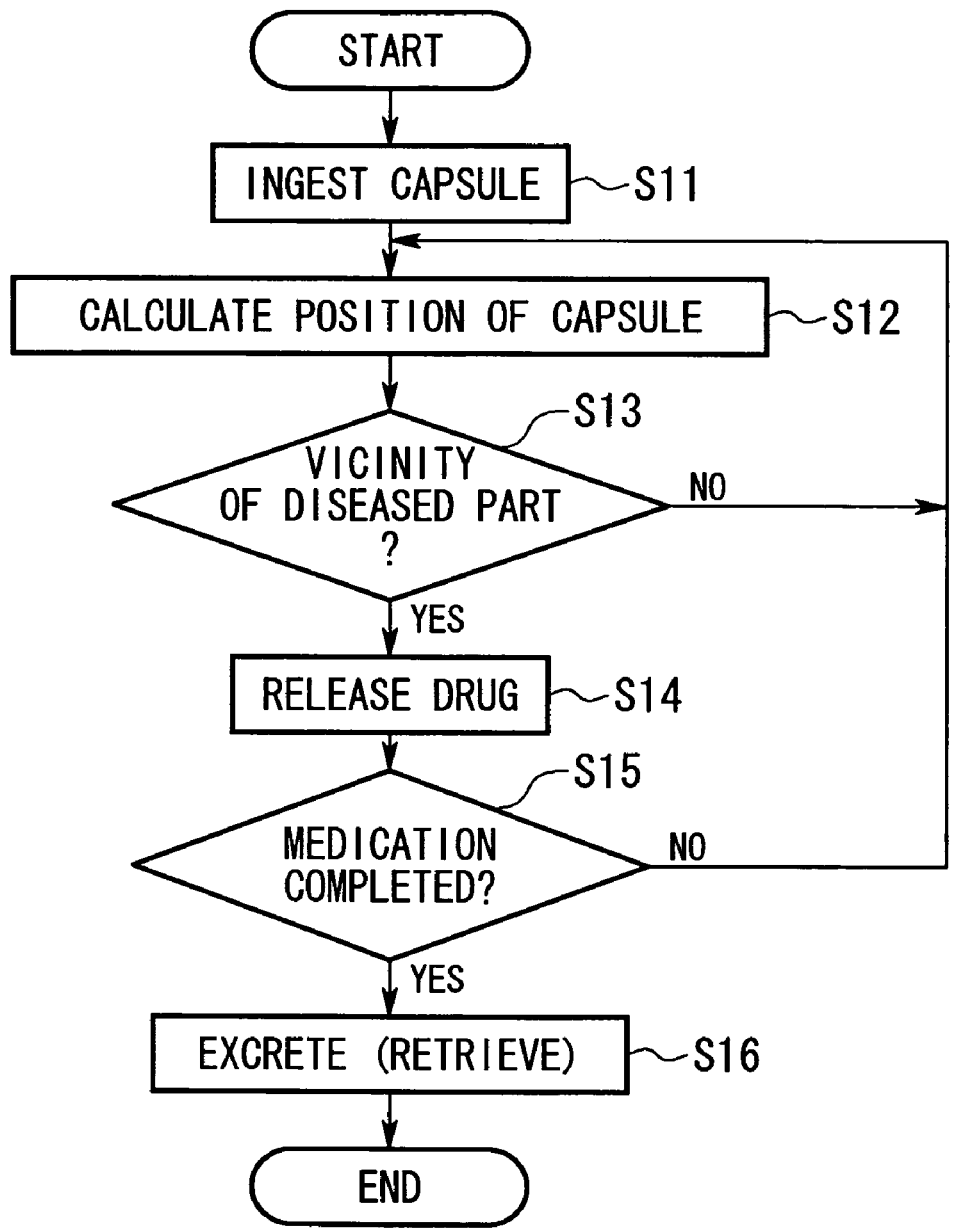
FIG. 6 is a flow chart for the case of orally ingesting the capsule for medication and performing medication for a diseased part.

The task of administering the drug A to the diseased part X within the living body P by using the capsule medication administration system which has a structure as described above will now be explained with reference to FIG. 5 and FIG. 6.

First, as shown in FIG. 1 and FIG. 3, in a medical facility or the like, the patient P puts on the external device 35 (S1). Next, the three dimensional marker 40 is attached to the external device 35 (S2), and he lies down upon the cot 32. The physician or the like, along with shifting the cot 32 by using the PC 34 so as to pass the patient into the detector 33, also causes the detector 33 to operate and performs X-ray photography of the patient P. At this time, the X-ray photography is performed from, at least, two different directions (S3). Desirably, CT scanning is performed, and photography is performed so as to obtain a three dimensional image. Furthermore, it would also be acceptable to arrange to extract, from this three dimensional image, the same images as the X-ray transmission images from the two directions. After this photography, the physician or the like takes in the image information which has been photographed by the detector into the PC 34 (S4), and, after predetermined processing such as image processing and the like has been performed, causes this image to be displayed upon the display monitor 34a.

At this time, the ball shaped bodies 44, 45, 46, and 47 of the three dimensional marker 40 are displayed simultaneously in the image which has been displayed upon the display monitor 34a, and it is possible to distinguish these ball shaped bodies 44, 45, 46, and 47 from one another (S5), since their diameters are mutually different. After having recognized these ball shaped bodies 44, 45, 46, and 47, then it is calculated from which direction the patient P has been photographed (S6), based upon the position of, and the distance to, the center of each of the ball shaped bodies 44, 45, 46, and 47. The physician or the like performs internal diagnosis based upon the image which has been displayed upon the display monitor 34, and specifies the diseased part X for which medication is required (S7).

After having specified the diseased part X, then the physician or the like specifies the position of this diseased part X. In other words, as shown in FIG. 3, since photography has been performed from at least two directions, the position of the diseased part X is specified by taking as a standard the three dimensional marker 40 according to the mutual relation of each of the ball shaped bodies 44, 45, 46, and 47 and the above body part X (S8). Furthermore, the position of the diseased part X with respect to the external device 35 is specified (S9), based upon the relative positional relationship between the three dimensional marker 40 and the external device 35.

After the physician or the like has specified the diseased part X and the position of the diseased body art X as described above, then the positional information for this diseased part X is inputted into the memory 53 of the external device 35 using the PC 34, and is recorded (S10). In other words, input of the conditions for causing the release section 14 to operate is performed to the external device 35. On the other hand, after the X-ray photography by the specification device 31 has been completed, along with the patient P taking off the three dimensional marker 40 from the external device 35, also he receives the capsule for medication 10 from the physician or the like and orally ingests it (S11). It should be understood that, after having received the capsule for medication 10, the patient P may leave the medical facility.

When the patient P orally ingests the capsule for medication 10, a switch not shown in the figures of the capsule for medication P is turned on, and the capsule for medication goes into the operational state. When the capsule for medication goes into the operational state, electrical power is supplied from its battery 17 to its various structural components. The capsule for medication 10 shifts within the living body while transmitting electromagnetic waves from the information transmission section 12. These electromagnetic waves which have been transmitted from the information transmission section 12 are received by the reception section 50 of the device external to the living body, and are sent to the decision section 51. The decision section 51 calculates the position of the capsule for medication 10 with respect to the external device 35 from the reception direction and the reception level of these electromagnetic waves which have been transmitted (S12). Furthermore, from the position information for the capsule for medication 10 which has thus been calculated and the position information for the diseased part X which is recorded in the memory 53, the decision section 51 decides whether or not the capsule for medication 10 has arrived at the position of the diseased part X (S13). When the position information for the capsule for medication 10 and the position information for the diseased part X agree with one another, the decision section 51 transmits a release signal towards the interior of the living body from the transmission section 52 external to the living body. In other words, the decision section 51 performs control of the release section 14 via a release signal.

The release signal which has been transmitted from the transmission section 52 external to the living body is received by the reception section 15 of the capsule for medication 10, and is sent to the control section 16. Upon receipt of this release signal, the control section 16 operates the opening and closing valves 24 and 25, and opens the body fluid intake conduit 21 and the drug release conduit 23. When the body fluid intake conduit 21 and the drug release conduit 23 are opened, body fluid F flows into the interior of the reservoir 13 via the body fluid intake conduit 21 from the body fluid intake aperture 20, and soaks into the expandable chemical B. The expandable chemical B expands upon the body fluid F thus soaking into it, and, due to the pressure of this expansion, the drug A is pushed out from the reservoir 13, and the drug A is released to the exterior of the casing 11 from the drug release aperture 22 via the drug release conduit 23 (S14). Therefore, since the drug A is released at the position of the diseased part X which has been specified by the specification device 31, accordingly it is possible to apply medication directly to the diseased part X.

If the specification device 31 has specified a plurality of diseased parts X, then the position of each of these diseased parts X is stored in the memory 53, and the drug A is administered to all of the diseased parts X. In this case, the decision section 51 decides whether or not the capsule for medication 10 has arrived at the positions of all of the diseased parts X. When it has been decided that medication has been completed at the positions of all of the diseased parts X, the operation is terminated (S15). After this, the capsule for medication 10 is excreted and is retrieved (S16).

According to the capsule medication administration system 1 described above, the unit 30 external to the living body specifies the diseased part X and the position of this diseased part X by the X-ray CT device which is utilized as the specification device 31. After having specified the diseased part X and the position of this diseased part X, the decision section 51 decides whether or not the capsule for medication 10 has arrived at the position of the diseased part X, based upon the position information for the capsule for medication 10 which has been received by the reception section 50 external to the living body and the position information for the diseased part which has been specified by the specification device 31. The capsule for medication 10 releases the drug A at the position of the diseased part X based upon the result of decision by the decision section 51. In other words, it is possible to perform medication accurately and moreover directly to the diseased part X, since it is possible to cause the position information of the diseased part X which has been specified by the X-ray CT device which has been utilized as the specification device 31 to be reflected in the capsule for medication 10, and it is thereby possible to release the drug A at the position of the diseased part X.

Next, the second embodiment of the capsule medication administration system according to the present invention will be explained with reference to FIG. 7 through FIG. 10. It should be understood that, to structural elements which are the same as the first embodiment, the same reference symbols are appended, and the explanation thereof is curtailed.

In the first embodiment, when the decision section 51 decides that the capsule for medication 10 has arrived at the position of the diseased part X, the release signal is transmitted to the capsule for medication 10, and medication is caused to be performed. In the second embodiment, when the decision section 51 decides that the capsule for medication (a capsule type medical device) 110 has arrived at the position of the diseased part X, an in-vivo information acquisition signal is transmitted from the external device 35 to the capsule for medication 110, and thereby the capsule for medication 110 is caused to acquire in-vivo information, and when it has been decided that medication is required based upon this in-vivo information, a release signal is transmitted to the capsule for medication 110, and medication is performed.

Figure 7:
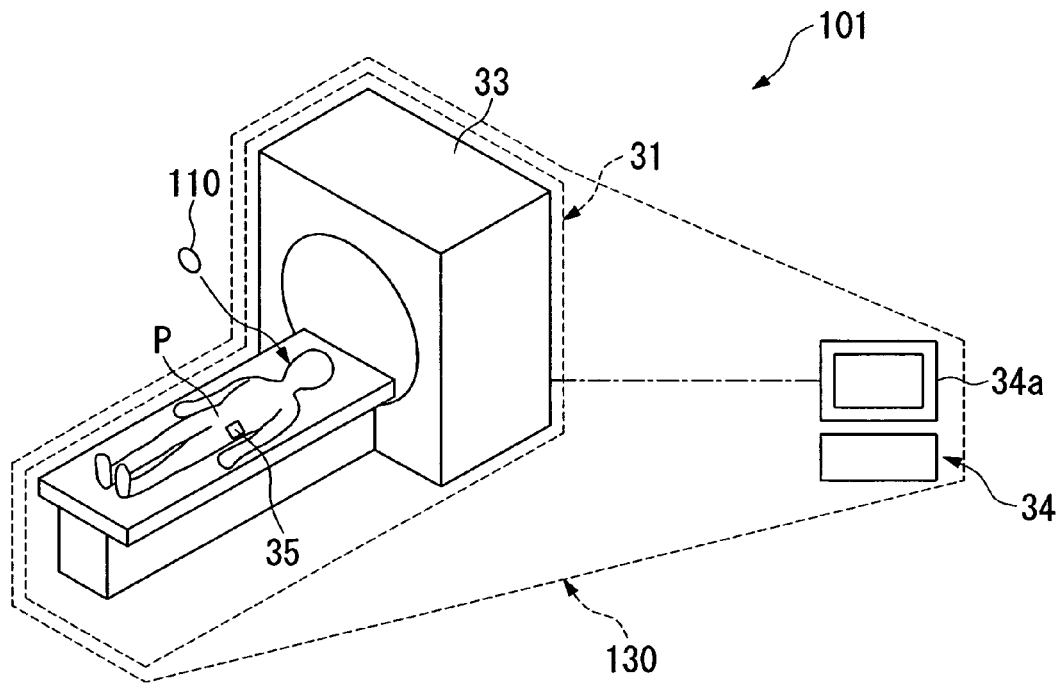
FIG. 7 is a schematic figure showing a second embodiment of the capsule medication administration system according to the present invention.

As shown in FIG. 7, the capsule medication administration system 101 of this embodiment includes the capsule for medication 110, and a unit 130 external to the living body.

Figure 8:
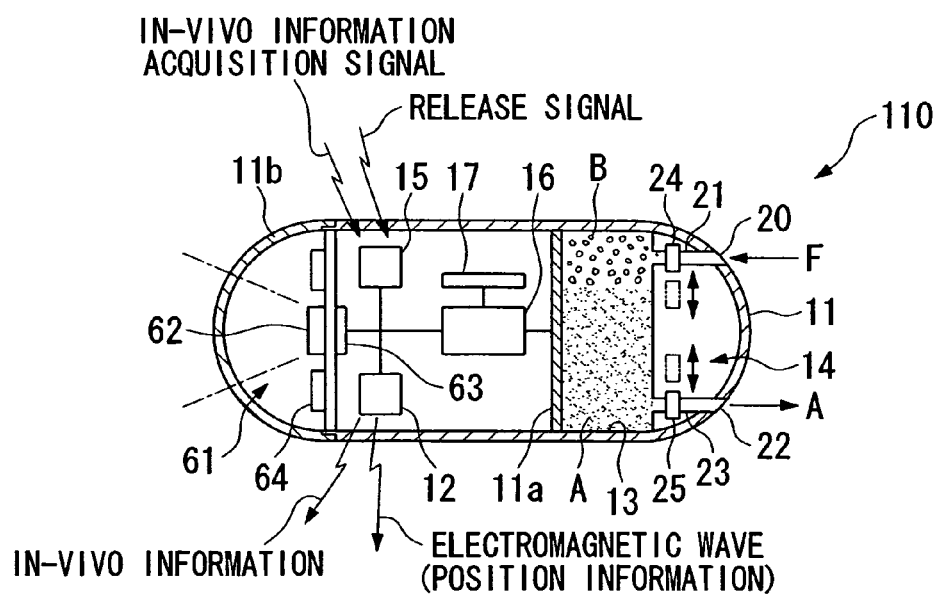
FIG. 8 is a sectional view showing a capsule for medication which is used in the capsule medication administration system shown in FIG. 7.

As shown in FIG. 8, the capsule for medication 110 includes, within the casing 11, an observation device (an observation section) 61 which acquires an image, which is in-vivo information. This observation device 61 includes an objective lens 62, an image formation element 63 such as a CMOS imager or the like, and LEDs 64. The objective lens 62 is disposed on the inside of a transparent cover 11b which is provided at one end of the casing 11. The image formation element 63 is provided at the focal position of the objective lens 62. The LEDs 64 are provided at the perimeter of the objective lens 62, and emit light for illumination so as to illuminate the visual field range of the objective lens 62.

The reception section 15 which is provided in the capsule for medication 110 is equipped with the function of receiving, in addition to the release signal, the in-vivo information acquisition signal. In the same way, the control section 16 which is provided to the capsule for medication 110 is equipped with the function of causing the observation device 61 to operated, when the reception section 15 has received the in-vivo information acquisition signal. In the same way, the information transmission section 12 which is provided to the capsule for medication 110 is equipped with the function of transmitting the in-vivo information which has been acquired by the observation device 61 (the photographic image) to outside the living body (to the external device 35).

Figure 9:
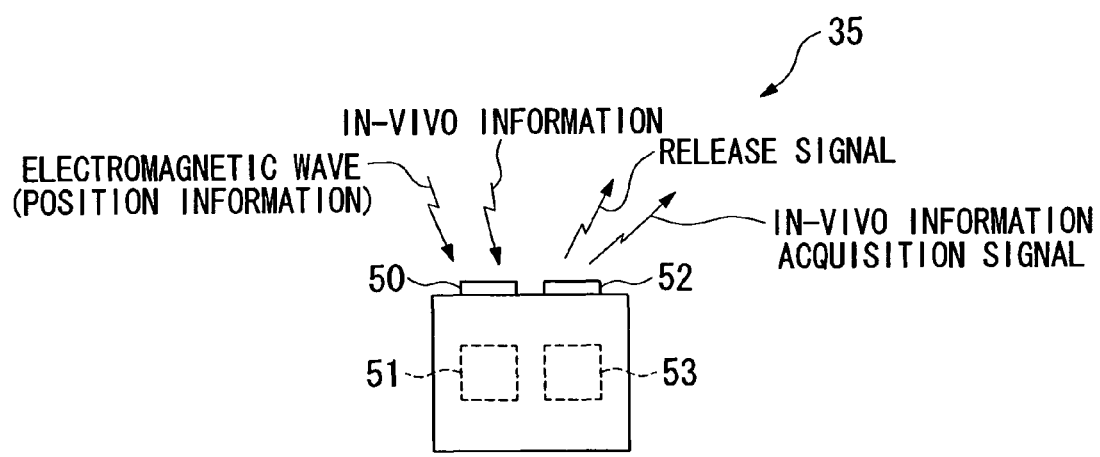
FIG. 9 is a structural view showing a device external to the living body which is used in the capsule medication administration system shown in FIG. 7.

As shown in FIG. 9, the transmission section 52 external to the living body which is provided to the external device 35 of the unit 130 external to the living body is equipped with the function of transmitting the in-vivo information acquisition signal, when the decision result of the decision section 51 is that the capsule for medication 110 has decided that has arrived at the position of the diseased part X. In the same manner, the reception section 50 external to the living body which is provided to the external device 35 is equipped with the function of receiving the in-vivo information in addition to the position information. In the same manner, the decision section 51 which is provided to the external device 35, along with deciding whether or not to perform medication based upon the in-vivo information which the reception section 50 external to the living body has received, is equipped with the function of controlling the transmission section 52 external to the living body so as to transmit a release section towards the capsule for medication 110, when it has been decided to perform medication. Furthermore, when it has been decided to perform medication, the decision section 51 evaluates the in-vivo information, which is the photographic image which is sent, and along with detecting, for example, red color, compares the amount thereof which has been detected with a threshold value which is set in advance, and, if it is greater than the threshold value, makes the decision that this location is a hemorrhagic site (a diseased part X) for which medication is required.

Figure 10:
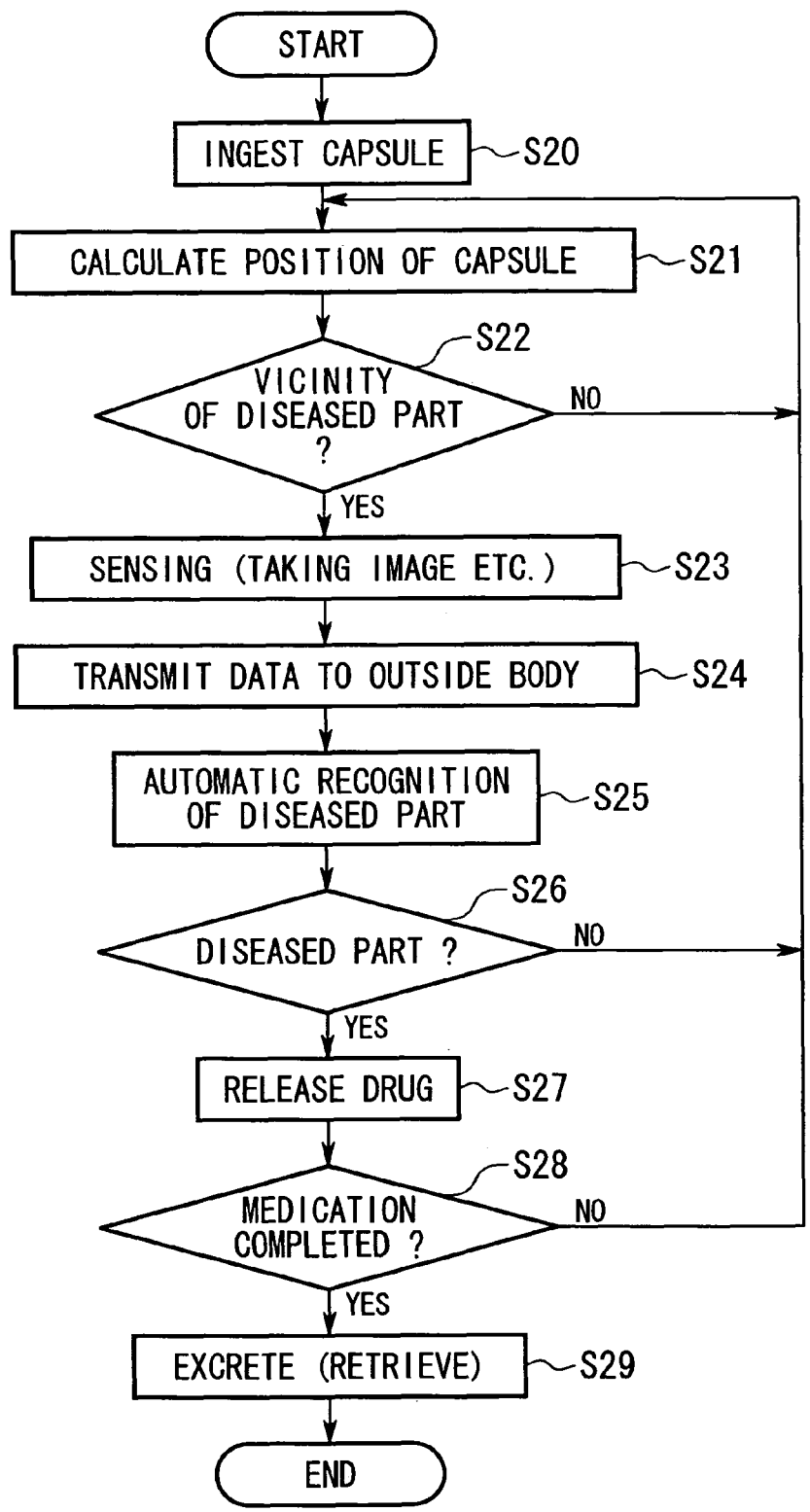
FIG. 10 is a flow chart for the case of orally ingesting the capsule for medication and performing medication for a diseased part.

The task of administration of the drug A to the diseased part X within the living body P using the capsule medication administration system 101 which has the above described structure will now be explained with reference to FIG. 10.

First, a physician or the like has specified the diseased part X for which medication is required and the position of that diseased part X by using the specification device 31, then the positional information for this diseased part X is inputted into the memory 53 of the external device 35 using the PC 34, and is recorded. After this, the patient P orally ingests the capsule for medication 110 (S20).

The capsule for medication 110 which has been orally ingested shifts within the living body while transmitting electronic waves to the outside from the information transmission section 12. These electromagnetic waves which have been transmitted from the information transmission section 12 are received by the reception section 50 of the external device 35, and are sent to the decision section 51. The decision section 51 calculates the position of the capsule for medication 110 with respect to the external device 35 based upon the reception direction and the reception level of these electromagnetic waves which have been transmitted from the information transmission section 12 (S21). Next, the decision section 51 decides whether or not the capsule for medication 110 has arrived at the position of the diseased part X from the positional information of the capsule for medication 110 which has been calculated and the positional information for the diseased part X which is recorded in the memory 53 (S22). When the positional information for the capsule for medication 110 and the positional information for the diseased part X agree with one another, the decision section 51 transmits the in-vivo information acquisition signal from the transmission section 52 external to the living body towards the interior of the living body.

The in-vivo information acquisition signal which has been transmitted from the transmission section 52 external to the living body is received by the reception section 15 of the capsule for medication 110, and is sent to the control section 16. The control section 16 receives this, and causes the observation device 71 to operate, thus acquiring in-vivo information (S23). The observation device 61 emits light for illumination to the visual field range of the objective lens 62 from the LED 64, and forms an image of the vicinity of the diseased part X with the objective lens 62 and the image formation element 63. Furthermore, the in-vivo information which has been acquired by the observation device 61 is transmitted to outside the living body by the information transmission section 12 (S24).

The in-vivo information which has been transmitted is received by the reception section 50 of the external device 35, and is sent to the decision section 51. The decision section 51 recognizes the diseased part X based upon this in-vivo information, which is the photographic image which has been transmitted (S25). The decision section 51 detects, for example, detecting red color which is included in the photographic image, it compares together this detected amount and a threshold value which has been set in advance, and if the detected amount is greater than or equal to the threshold value, it decides (S26) that this location is a diseased part X for which medication is required.

When the decision section 51 decides that there is a diseased part X for which medication is required, it transmits a release signal towards the interior of the living body from the transmission section 52 external to the living body. This release signal which has been transmitted from the transmission section 52 external to the living body is received by the reception section 15 of the capsule for medication 110, and is sent to the control section 16. The control section 16 receives this release signal and causes the opening and closing valves 24 and 25 to operate, and releases the drug A (S27).

If a plurality of diseased part X have been specified, the specification device 31 records the positions of each of these diseased parts X in the memory 53, and administers the drug A at the positions of all of these diseased parts X. In this case, the decision section 51 decides whether or not the capsule for medication 10 has arrived at the positions of all of the diseased parts X. When it is decided that medication has been completed at the positions of all the diseased parts X, the operation is terminated (S28). After this, the capsule for medication 110 is excreted and is retrieved (S29).

According to the above described capsule medication administration system 101, after the capsule for medication 110 has arrived at the position of the diseased part X, the decision section 51 performs a decision as to whether or not to administer medication, based upon the in-vivo information, which is the photographic image that has been acquired by the observation device 61 for the position of the diseased part X, accordingly it is possible to administer medication to the diseased part X in a more accurate manner.

Furthermore, since the observation device 61 is not always in operation, but rather only operates when it arrives at the position of the diseased part X and has received the in-vivo information acquisition signal from the external device 35, accordingly it is possible to anticipate an improvement in electrical power economy. Furthermore, since the acquisition of the in-vivo information is performed by the observation device 61, accordingly it is also possible to perform interim observation due to the medication.

It should be understood that although, in this embodiment, the observation device 61 which forms an image of the interior of the living body is utilized as the observation section, the observation section is not limited to this; it would also be acceptable to utilize a sensor which detects in-vivo information such as pH or blood or the like. In this case, the decision section would make a decision as to whether or not this is the diseased part, based upon the pH value which has been acquired or a component within the blood, or the like.

Next, the third embodiment of the capsule medication administration system according to the present invention will be explained with reference to FIG. 11 through FIG. 14. It should be understood that, to structural elements which are the same as the first embodiment, the same reference symbols are appended, and the explanation thereof is curtailed.

In the first embodiment, an X-ray CT device is employed as the specification device 31 of the unit 30 external to the living body. In the third embodiment, an endoscope device is employed as the specification device (the medication position specification device) 231 of the unit 230 external to the living body.

Figure 11:
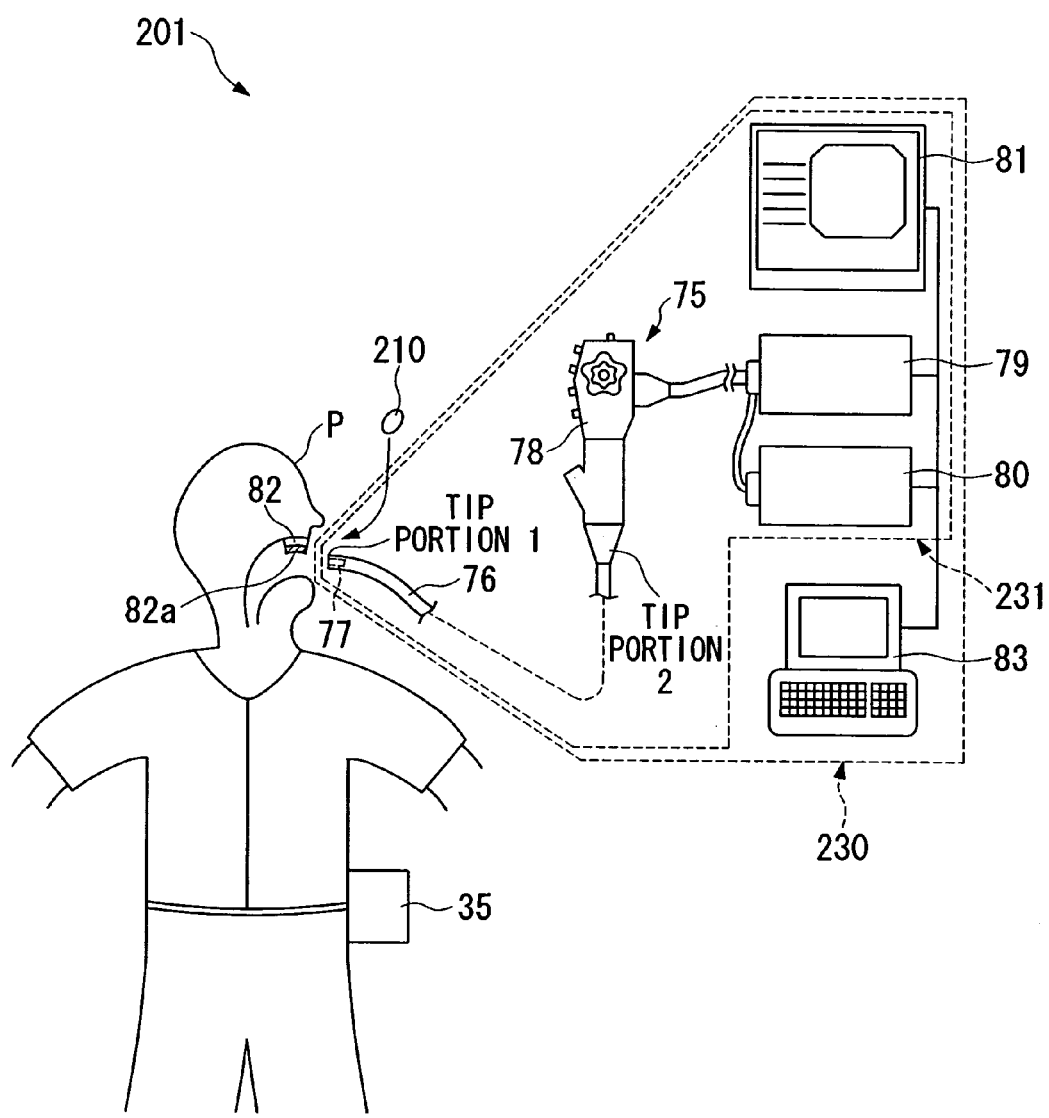
FIG. 11 is a schematic figure showing a third embodiment of the capsule medication administration system according to the present invention.

As shown in FIG. 11, the capsule medication administration system 201 of this embodiment includes a capsule for medication (a capsule type medical device) 210, and a unit 230 external to the living body which includes an endoscope device as the specification device 231.

Figure 12:
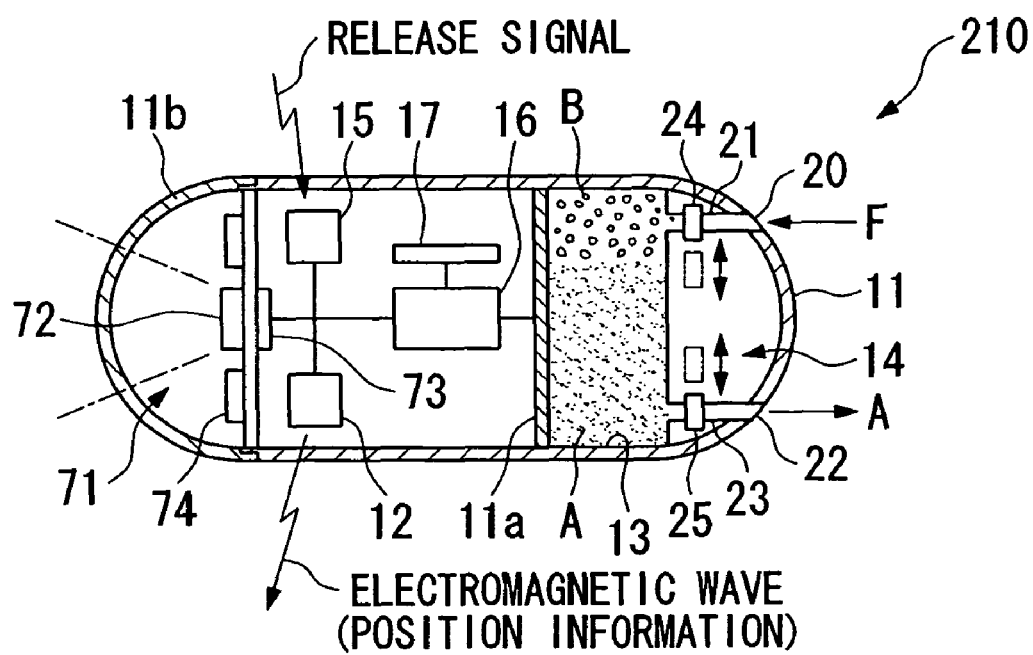
FIG. 12 is a sectional view showing a capsule for medication which is used in the capsule medication administration system shown in FIG. 11.

As shown in FIG. 12, the capsule for medication 210 includes an image formation device (an image formation section) 71 which forms an image of the interior of the living body. This image formation device 71 includes an objective lens 72, an image formation element 73 such as a CMOS imager or the like, and LEDs 74. The objective lens 72 is disposed at the inside of a transparent cover 11b which is provided at one end of the casing 11. The image formation element 73 is provided at the focal position of the objective lens 72. The LEDs 74 are provided at the perimeter of the objective lens 72, and emit light for illumination so as to illuminate the visual field range of the objective lens 72. Furthermore, the image formation device 71 sends image information about the images which have been formed to the image transmission section 12.

The information transmission section 12 which is equipped to the capsule for medication 210 is provided with a timer function, and, along with specifying positional information for itself by establishing a correspondence with the time interval which elapsed from the oral ingestion to within the living body until the time point of photographing the image information for the images formed by the image formation device 71, also transmits the image information of the images which have been formed to outside the living body.

As described above, an endoscope device is employed as the specification device 231. As shown in FIG. 11, within an endoscope device main body 75, there are provided an insertion section 76 which is inserted within the coelom, an image acquisition device 77, and an actuation section 78. The image acquisition device 77 is provided at the one tip portion (the tip portion 1) of the endoscope device main body 75 which is inserted within the coelom. The actuation section 78 is provided at the other tip portion (the tip portion 2) of the endoscope device main body 75, at the opposite end to this one tip portion (the tip portion 1) at which the image acquisition device 77 is provided.

The endoscope device main body 75 is connected to a light source device 79 and an image processor device 80. The light which has been generated by the light source device 79 is transmitted via an optical fiber which is not shown in the figures which passes through the interior of the endoscope device main body 75 to the one tip portion of the endoscope device main body 75, and is emitted within the coelom as illumination. At the one tip portion of the endoscope device main body 75 there is provided an image formation element (a CCD) which is not shown in the figures. The signal which has been acquired by this CCD is propagated along wiring material which is provided in the interior of the endoscope device main body 75, and is transmitted to the image processor device 80. The signal from the image formation element is received by the image processor device 80, which creates an image of the interior of the coelom. This image which has been created is displayed upon the display monitor 81.

A mouthpiece 82 is put on to the mouth of the patient P. This mouthpiece 82 is attached an insertion amount detection device 82a which detects the insertion amount of the insertion section 76 to within the coelom. The output of this insertion amount detection device 82a is also transmitted to a personal computer 83 (hereafter termed a PC).

The image data which have been generated are also transmitted to the PC 83. PC 83 records in correspondence with the image data which have been generated and the data of the insertion amount detection device 82a, and performs image processing and the like as represented by the categories shown in FIG. 13, as will be described hereinafter.

The task of administration of the drug A to the diseased part X within the living body P using the capsule medication administration system 201 which has the above described structure will now be explained with reference to FIG. 11, FIG. 13, and FIG. 14.

First, as shown in FIG. 11, in a medical facility or the like, the patient P undergoes an endoscope examination (S30). A physician or the like performs the original diagnosis of the images which have been obtained by using the specification device 231, and specifies the diseased part X for which medication is required (S31). For this task of specifying the diseased part X, he performs checking of the images using the PC 83, and leaves a record by appending a flag to the image data which indicates the diseased part X.

Figure 13:
FIG. 13 is a figure showing examples of position information for a diseased part, and data after conversion, according to a specification device of the capsule medication administration system shown in FIG. 11.
Figure 14:
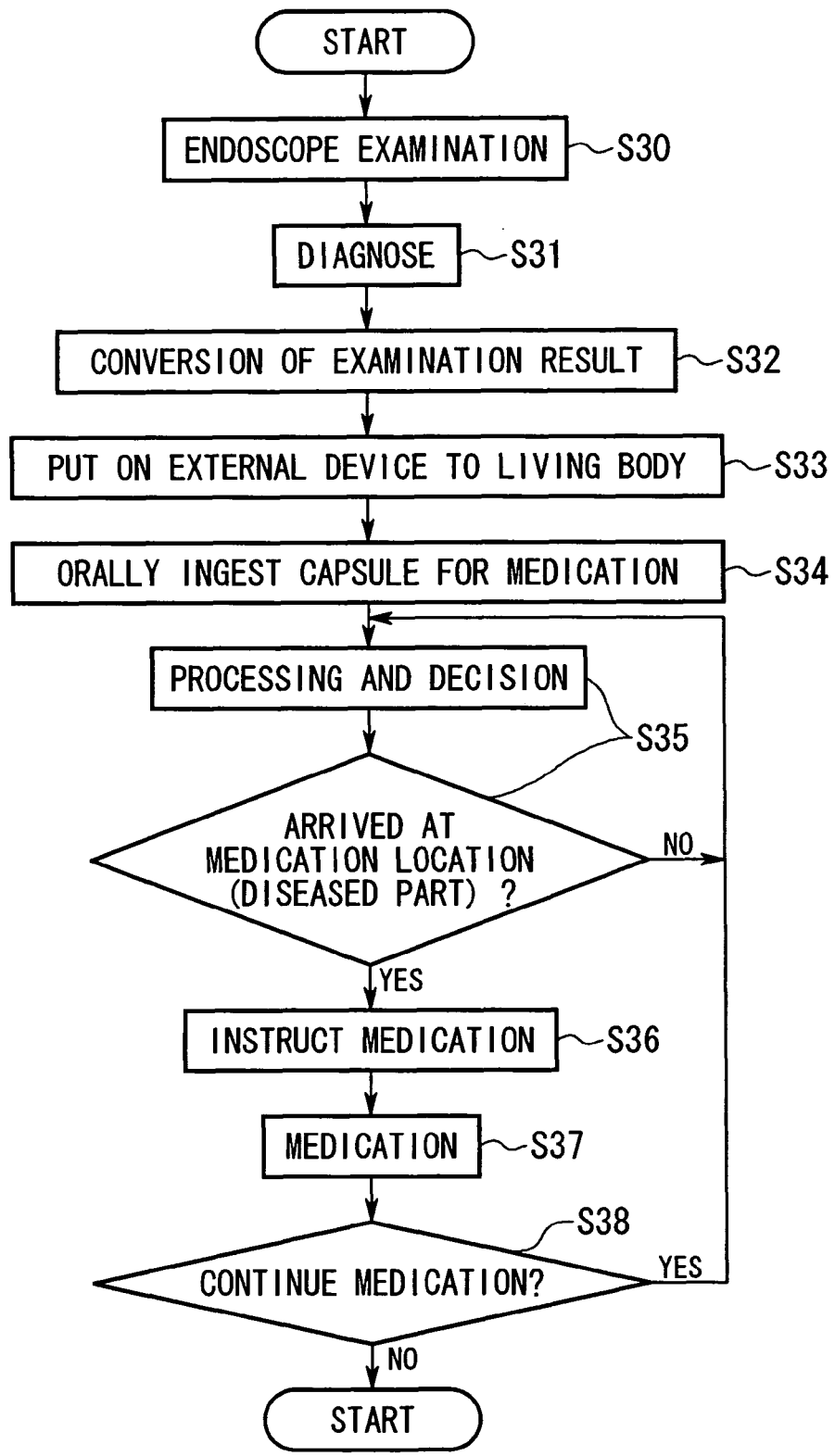
FIG. 14 is a flow chart for the case of performing medication for a diseased part X with the capsule medication administration system shown in FIG. 11.

After having specified the diseased part X in the above described manner, as shown in FIG. 13, the physician or the like converts the image data for the diseased part X by using the PC 83 (S32). The details of this conversion will be described in detail hereinafter. Furthermore, the physician or the like inputs the data which have been converted into the memory 53 of the external device 35 using the PC 83, and records them there.

Next, along with putting on the external device 35 (S33), the patient P orally ingests the capsule for medication 210 (S34). When the capsule for medication 210 is thus orally ingested, electrical power is supplied from the battery 17 to the various structural components thereof due to the turning on of a switch which is not shown in the figures, and, along with the timer function of the information transmission section 12 operating, the image formation device 17 operates.

The capsule for medication 210 which has been orally ingested shifts while forming images of the interior of the living body with the image formation device 71. The images which have been photographed by the image formation device 71 are sent to the information transmission section 12. The information transmission section 12 transmits the elapsed time from when the capsule 210 is orally ingested and the image which has been photographed at that time point as a group of information to the external device 35.

The reception section 50 external to the living body of the external device 35 receives the information which has been transmitted from the information transmission section 12, and transmits it to the decision section 51. The decision section 51 performs the same processing as the processing which is performed by the PC 83 in the step S32, and compares together the image data which are stored in the memory 53 and the data after conversion by the PC 83 (S35).

If the result of this comparison is that it is decided that the data are the same or are extremely close to one another, then the decision section 51 decides that the portion which has been photographed is the medication site (the diseased part X), and transmits a release signal from the transmission section 52 external to the living body towards the interior of the living body (S36).

This release signal which has been transmitted from the transmission section 52 external to the living body is received by the reception section 15 of the capsule for medication 210, and is sent to the control section 16. The control section 16, upon receipt of this release signal, operates the opening and closing valves 24 and 25, and releases the drug A (S37).

If the specification device (endoscope device) 231 has specified a plurality of diseased part X, then the decision section 51 decides whether or not medication has been performed by the capsule for medication 210 for all of the diseased parts X (S38). If it decides that medication has been completed for all of the diseased parts X, then the operation terminates. After this, the capsule for medication 210 is excreted and is retrieved.

According to the capsule medication administration system described above, since the information about the diseased part X is obtained accurately with the endoscope device which has been employed as the specification device 231, and the diseased part X is specified by comparing together this information and the information which has been obtained by the capsule for medication 210, accordingly it is possible to perform the medication in a certain manner.

Furthermore, since the images which have been obtained by the specification device 231 are not utilized for comparison just as they are, but rather by comparing together the data after conversion, in other words by using the data which has been simplified, therefore the gross amount of calculation for the comparison is kept small, and accordingly it is possible to perform the comparison of the data easily.

Now, the details of the conversion of the data shown in FIG. 13 will be described.

Figure 31:
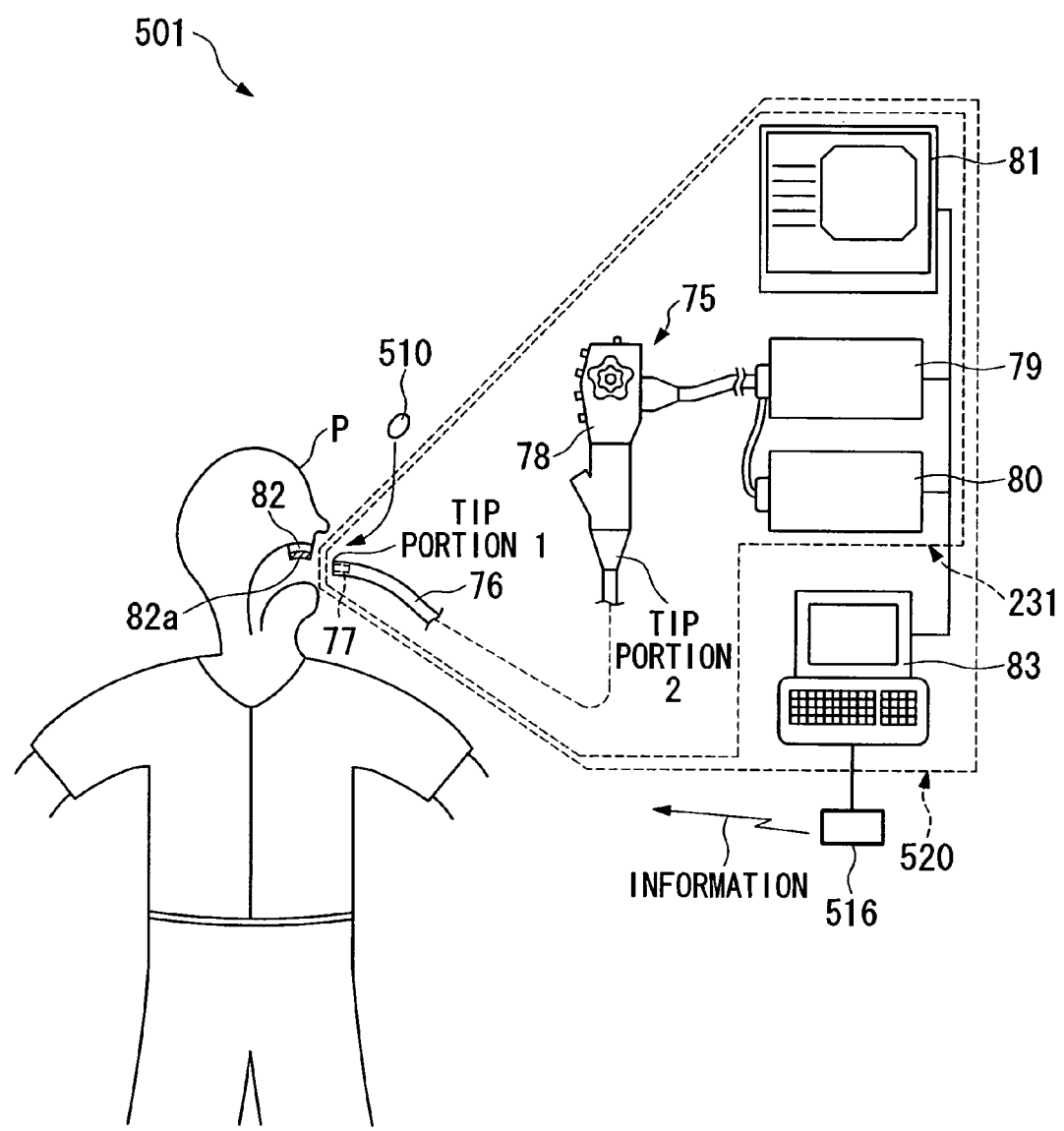
FIG. 31 is a schematic figure showing a sixth embodiment of the capsule medication administration system according to the present invention.

In FIG. 31, the left side is the image which is obtained by the endoscope device which is used as the specification device 231, and the insertion distance information of the insertion section 76 which is obtained at the same time. In the insertion distance information there is shown, for example, the insertion distance data of the insertion section 76 to within the coelom. The right side of the table shows the data after conversion.

First, as a first example, (1) and (2) in the Table will be explained.

In (1) and (2), a correspondence is established for the image which has been obtained by the endoscope device and the insertion distance of the insertion section 76 of the endoscope device to within the coelom, and conversion is performed, and the data after conversion is recorded in the memory 53. The data after conversion which is recorded in the memory 53 is the position and the image data of the diseased part X which has been selected based upon the insertion amount of the endoscope to within the coelom. (The case of (2) is a pattern of an image which has been simplified.)

The information which specifies the position may also be information about the supposed time period, from after the capsule for medication 210 has been orally ingested, until it arrives at the diseased part X. Furthermore, it would also be acceptable just to record the insertion amount of the insertion section 76 of the endoscope device, without performing any conversion thereof.

Photography within the coelom alimentary canal of the patient P is performed at fixed time intervals by the capsule for medication 210, according to the timer function which is provided in the information transmission section 12. The image data which has been photographed is converted to a data format which is suitable for wireless transmission by data compression conversion, analog-digital conversion and the like, and is transmitted from the information transmission section 12 to the exterior of the living body. The data which has been thus transmitted is received by the reception section 50 external to the living body of the external device 35.

The data which has been received by the reception section 50 external to the living body is sent to the decision section 51. The decision section 51 converts the images that have been photographed by the capsule for medication 210 to the same format as the data which has been recorded in the memory 53 (in case (2), to the image pattern which has been simplified).

Furthermore, the present position of the capsule for medication 210 is estimated based upon the history of the images which have been photographed (the site which currently is being photographed (the small intestine, the large intestine, or the like), and the time period that the capsule for medication 210 has been present at this site). This conversion may be done by the method of comparing together the arrival time and the supposed arrival time, or may be done by the method of comparing together the insertion amount of the insertion section 76 and the insertion distance of the capsule for medication 210.

If the positional information for the diseased part X which is recorded in the memory 53 and the positional information which is estimated by the decision section 51 are close to one another, then comparison together of the image of the diseased part X which is recorded in the memory 53 (in case (2), the image pattern) and the image which has been created by the decision section 51 from the image data from the capsule for medication 210 (in case (2), the image pattern) is performed. In this comparison, the procedure is performed by obtaining the correlation function. For this procedure of obtaining the correlation function, various different image processing techniques may be utilized.

If the correlation function which has been obtained is greater than some threshold value which has been set, then the decision section 51 decides that the present position is the vicinity of the diseased part X, and outputs an instruction to transmit the release signal from the transmission section 52 external to the living body.

Next, in case (3), the insertion distance when observing with the endoscope device, the variation of the average brightness of the image which has been photographed, and the image data are recorded in the memory 53 as the data after conversion. If the endoscope has a light adjustment function, it will also be acceptable to record, not the average brightness of the image, but the variation in the amount of light adjustment.

For an image which has been photographed by the capsule for medication 210, by the decision section 51 obtaining the average brightness of the image in the same manner as described above, and by writing this average brightness into the working memory 53, it is possible to obtain the change of the average brightness along with the progress of the capsule for medication 210. The variation curve of the average brightness until the capsule arrives at the diseased part X which is recorded in the memory 53 and the average brightness variation from the image which has been obtained by the capsule for medication 210 are compared together, and if the result of this comparison is that they are close, then the current position of the capsule for medication is evaluated as being the vicinity of the diseased part X. The subsequent processing is the same as in the above described cases (1) and (2). It should be understood that the curve of variation of the average brightness and so on may be approximated and simplified by a B-spline curve or a N-Bezier curve or the like.

Furthermore, in case (4), instead of the variation of the average brightness in case (3), change of the color balance is exploited. With regard to the other portions, they are the same as for case (3).

It should be understood that although, in this embodiment, an endoscope device is employed as the specification device 231, it would also be acceptable to utilize, in this method of detecting the medication position based upon the insertion distance, not just a method of using an endoscope, but also a method of obtaining the lumen distance by using an X-ray observation device, a CT scanner, an MRI scanner, an ultrasonic wave observation device, or the like.

Next, the fourth embodiment of the capsule medication administration system according to the present invention will be explained with reference to FIG. 15 through FIG. 24. It should be understood that, to structural elements which are the same as those included in the various embodiments described above, the same reference symbols are appended, and the explanation thereof is curtailed.

Figure 15:
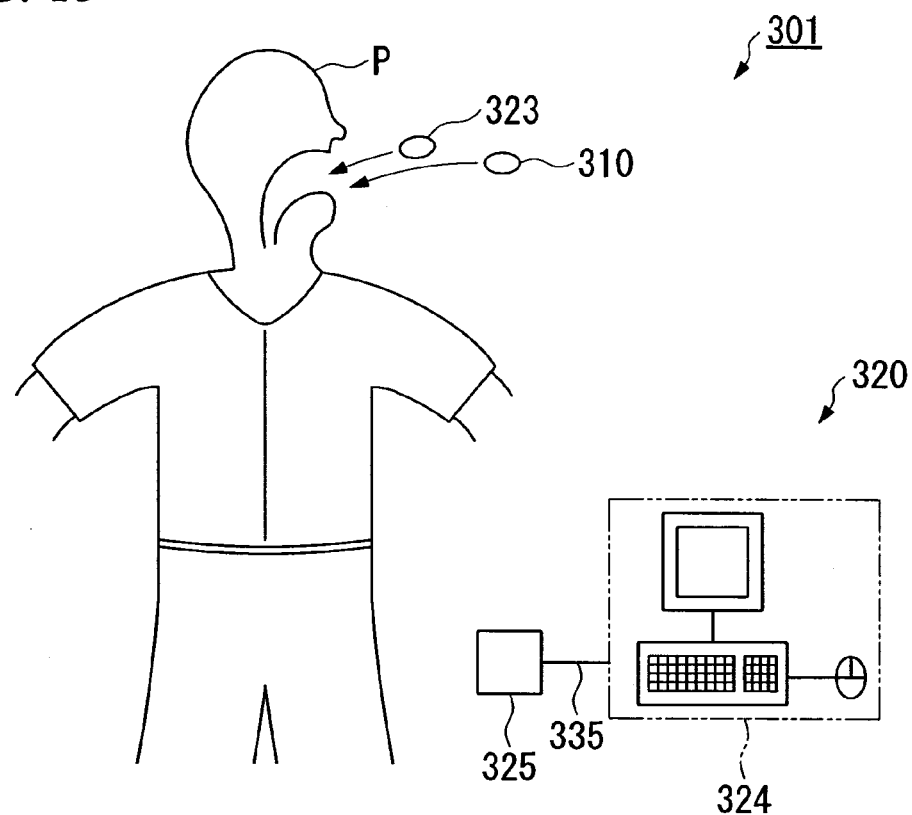
FIG. 15 is a schematic figure showing a fourth embodiment of the capsule medication administration system according to the present invention.

As shown in FIG. 15, the capsule medication administration system 301 of this embodiment includes a capsule for medication (a capsule type medical device) 310 which is orally ingested to within the living body P, and a medical device 320. The medical device 320 includes an observation system 321 (a device for acquiring in-vivo information) which obtains photographic images, which are in-vivo information, within his coelom, and a discharge mechanism (a marking device) 322 which leaves a marking M (an indicator) within his coelom.

Figure 16:
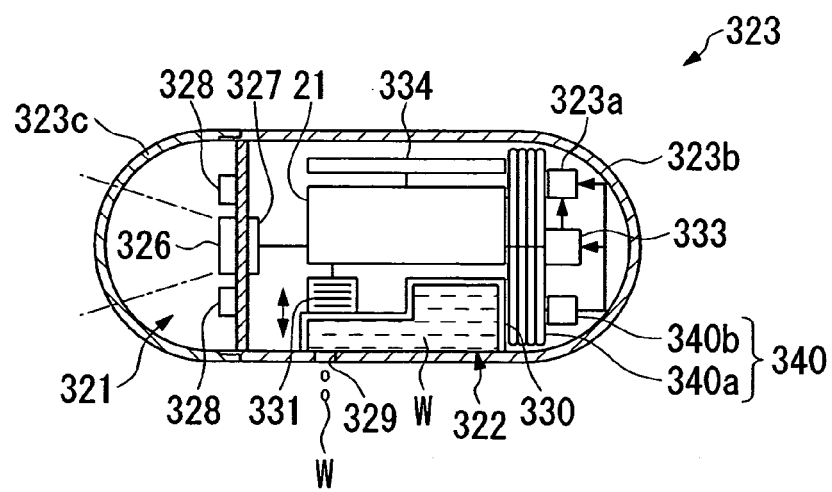
FIG. 16 is a sectional view showing a capsule medical device according to the present invention which is used in the capsule medication administration system shown in FIG. 15.

As shown in FIG. 15 and FIG. 16, the medical device 320 includes a capsule type medical device 323 (the second capsule type medical device), and a personal computer 324 (a reception device; hereinafter termed a PC). The capsule type medical device 323 includes, within a casing 11 (a covering section) which is formed in the shape of a capsule, an observation system 321, a discharge mechanism 322, and a wireless transmission device 323a (a transmission device or information transmission section). The wireless transmission device 323a transmits in-vivo information which has been acquired by the observation system 321 and operational information about the discharge mechanism 322 to the exterior of the casing 323b. The PC 324 includes an observational information receiver 325 which receives the information which has been transmitted to the exterior of the casing 323 by the wireless transmission device 323a.

The casing 323b of the capsule type medical device 323 is formed from plastic or the like so as to closely seal its interior, and a transparent cover 323c is provided at the one end thereof. An objective lens 326 which forms images of various portions within the living body is provided at the interior of this transparent cover 323c. An image formation element 327 such as, for example, a CMOS imager or a CCD or the like is provided at the focal position of the objective lens 326. LEDs 328 which emit light for illumination in order to illuminate the visual field range of the objective lens 326 are provided at the perimeter of the objective lens 326. In other words, this objective lens 326, this image formation element 327, and these LEDs 328 constitute the observation system 321.

A minute discharge aperture 329 is formed at one portion of the casing 323b. A reservoir 330 in which a marking material W such as a dye, a magnetic substance, a radioactive substance or the like is provided at the inside of this discharge aperture 329. A portion of this reservoir 330 is elastically deformable, and a piezo element 331 is provided in this elastically deformable portion. When an operating signal or the like is sent to this piezo element 331, the piezo element 331 expands and presses upon the reservoir 330, and the marking material W is discharged towards the exterior of the casing 323b from the discharge aperture 329. Therefore, a marking M such as a spot of black ink is made within the living body. This discharge aperture 329, reservoir 330, and piezo element 331 constitute the discharge mechanism 322. It should be understood that the marking material W disappears naturally when a predetermined time period has elapsed from when the marking M has been made within the living body. For example, if the marking M is made within the small intestine, due to the metabolism of tissue, this marking M disappears from the tube wall along with the intestinal tissue.

Furthermore, within the interior of the casing 323b, there are housed a control processing section 332, a memory 333 which stores in-vivo information which has been processed by this control processing section 332, and a battery 334 which supplies powers to the various structural components described above. The control processing section 332, along with controlling the observation system 321 and the discharge mechanism 322, also performs predetermined processing upon the in-vivo information which has been acquired by the observation system 321.

The control processing section 332 is equipped with the function of, after the capsule has been ingested into the living body, sending an operating signal to the piezo element 331, and, while the capsule shifts within the living body, periodically causing the discharge mechanism 322 to operate so as to make a marking M within the living body, for example once every five minutes. Furthermore it is equipped with the function of, at the same time, controlling the observation system 321 so as to cause it to acquire in-vivo information by forming images randomly, for example twice every second, of the interior of the living body. Moreover the control processing section 332 is equipped with the function of, along with performing predetermined processing upon the in-vivo information which has been sent from the observation system 321, also successively storing this in-vivo information in succession in the memory 333 in correspondence with the timing of operation of the piezo element 331. In other words, it is equipped with the function of establishing a correspondence between the position of the marking M which has been made within the living body, and the in-vivo information, and causing it to be stored in the memory 333.

Furthermore, after the capsule type medical device 323 has been excreted from the living body P and has been retrieved, it outputs in-vivo information which is stored in the memory 333 to the PC 324. Therefore, the physician can perform diagnosis based upon the in-vivo information which has been inputted to the PC 324.

Figure 17:
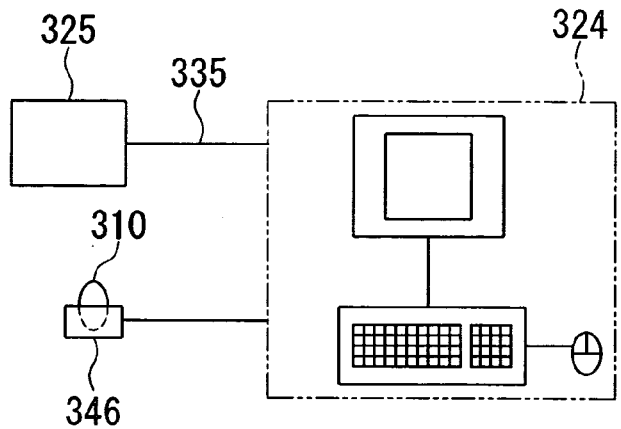
FIG. 17 is a structural view showing a personal computer which is a structural component of a medical device according to the present invention which is used in the capsule medication administration system shown in FIG. 15.
Figure 18:
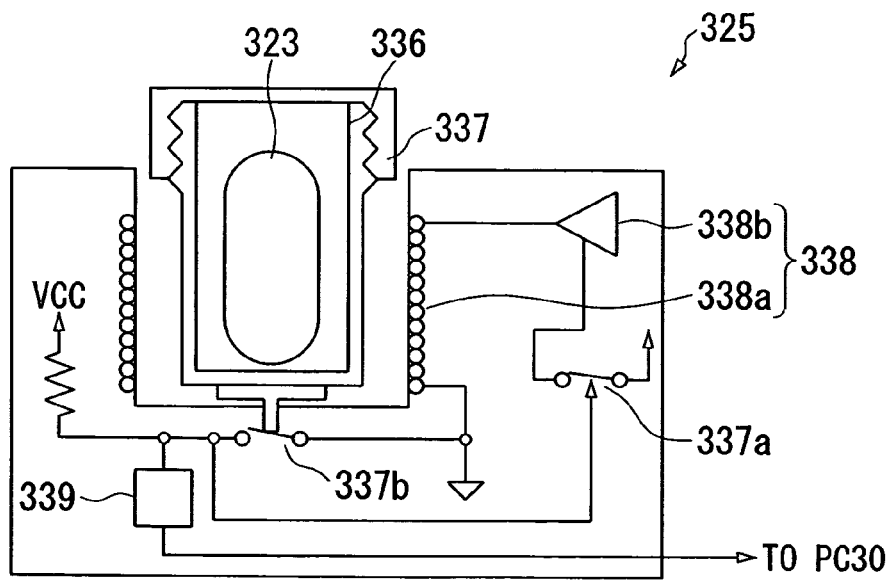
FIG. 18 is a structural view showing an observational information receiver of the personal computer shown in FIG. 17.

In other words, as shown in FIG. 17 and FIG. 18, the PC 324 includes the observational information receiver 325 which performs wireless communication with the capsule type medical device 323, and obtains the in-vivo information. This observational information receiver 325 is connected to the PC 324 via a cable 335, and includes a vessel installation section 337 in which there is installed a vessel 336 in the interior of which the capsule type medical device 323 is stored, an electrical power supply device 338 which supplies electrical power to the capsule type medical device 323 which has been stored in this vessel 336, and a wireless reception device 339.

The electrical power supply device 338, for example, may include a coil 338a which is arranged so as to surround the vessel installation section 337, a driver 338b which causes AC electrical current to flow in the coil 338a, and a switch 337a which turns a power supply to the driver 338b ON and OFF. This switch 337a is connected to a placement detection switch 337b which is disposed at the bottom surface of the vessel installation section 337, and operates when this placement detection switch 337b has detected that the vessel 336 has been placed in the vessel installation section 337. In other words, when the vessel 336 has been placed in the vessel installation section 337, supply of AC power from the driver 338b is caused to flow in the coil 338a.

Furthermore, the wireless reception device 339, along with receiving the signals which have been transmitted from the capsule type medical device 323, also transmits them to the PC 324 via the cable 335.

Moreover, as shown in FIG. 16, the capsule type medical device 323 includes, within the casing 323b, a wireless transmission device 322a which transmits a signal to the wireless reception device 339 of the observational information receiver 325, and an electrical power reception device 340 which receives electrical power from the electrical power supply device 338.

The electrical power reception device 340 includes a coil 340a for reception and an AC-DC converter 340b. When the electrical power reception device 340 is supplied the electrical power from the electrical power supply device 338, it distributes electrical power to the wireless transmission device 313 and the memory 333, and the in-vivo information which has been stored in the memory 333 is sent from the wireless transmission device 313 to the wireless reception device 339. This in-vivo information which has been sent to the wireless reception device 339 is sent to the PC 324.

Due to this, as described above, it is possible to output the in-vivo information which is stored in the memory 333 to the PC 324.

Figure 19:
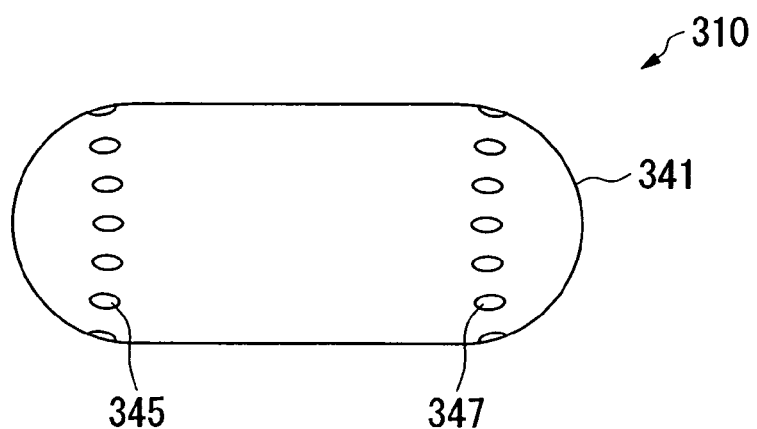
FIG. 19 is an external view showing a capsule for medication according to the present invention which is used in the capsule medication administration system shown in FIG. 15.
Figure 20:
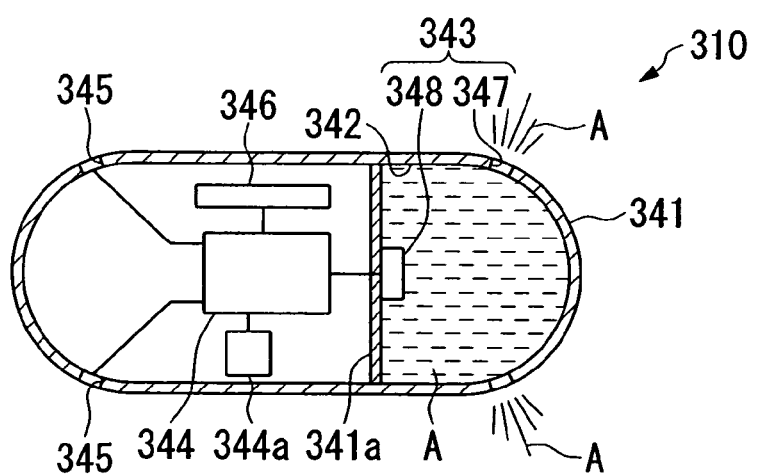
FIG. 20 is a sectional view showing the capsule for medication shown in FIG. 19.

Next, the capsule for medication 310 is shown in FIG. 19 and FIG. 20. FIG. 19 shows an exterior view of the capsule for medication 310, while FIG. 20 shows a sectional view thereof. The capsule for medication 310 includes, within a capsule shaped casing (an exterior housing portion) which is orally ingested into the living body P, a reservoir 342 (a drug retention section) which retains a drug A, a release device 343 (a drug release section) which releases the drug A which is retained in the reservoir 342, a control section 344 (a release control device) which causes the release device 342 to operate, a sensor 345 (a detection device or indicator detection device) which detects a marking M made within the living body which indicates the drug release position, and a battery 346 which supplies electrical power to these various structural components.

The casing 341 is formed from plastic or the like so as tightly to enclose its interior, and a reservoir 342 is provided at one end of its interior, surrounded by a wall portion 341a and the inner peripheral surface of the casing 341. On the outer surface of the casing 341 which is the perimeter of the reservoir 342, there are formed a plurality of drug apertures 347 around the perimeter of the casing 341. A thin membrane not shown in the figures is formed over these drug apertures 347, and thereby the drug A which is retained in the reservoir 342 is prevented from leaking out from the drug apertures 347. Furthermore, a heater 348 is provided in the reservoir 342. This heater 348 is equipped with the function of causing the generation of gas bubbles by momentary application of heat, so that the pressure thereof breaks the thin membrane over the drug apertures 347, thereby releasing the drug A from the drug apertures 347. In other words, this drug aperture 347 and heater 348 constitute the release device 342.

Figure 21A:
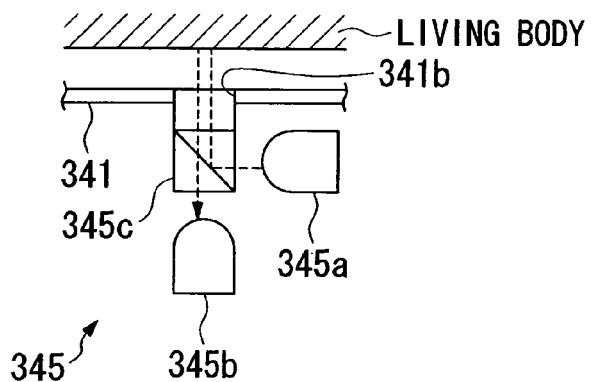
FIG. 21A and FIG. 21B are structural views showing the sensor of the capsule for medication shown in FIG. 19.
Figure 21B:
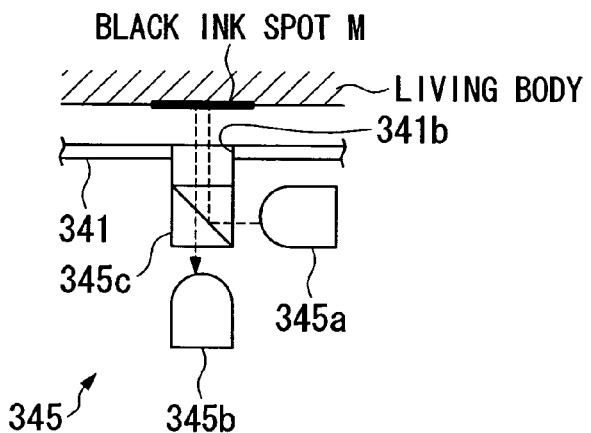

The sensors 345 are provided in plurality around the axis of the casing 341, i.e. around the outer surface of the other end of the casing 341, and are equipped with the function of detecting the marking M while the capsule is shifting within the living body and sending it to the control section 344. In other words, as shown in FIG. 21A and FIG. 21B, the sensor 345 includes a light emitting element 345a which includes an LED or the like, an optical detector 345b, and a prism 345c. It should be understood that the sensor 345 will be explained with the marking M taken as being a spot of black ink. The light which has been emitted by the light emitting element 345a is reflected by the prism 345c, and is emitted within the living body through a window 341b which is formed in the casing 341. This light which has been emitted is reflected by the living body, and is incident upon the optical detector 345b after having passed through the window 341b and the prism 345c. Furthermore, the optical detector 345b detects the level of this incident light.

If the sensor is being operated at the position of tissue which has not been spotted with black ink, then the light which has been emitted is reflected by the living tissue, and this reflected light is detected by the optical detector 345c.

On the other hand, if the sensor is operated at the position of tissue which has been spotted with black ink, since the living tissue is spotted with black ink, the light is absorbed by this living tissue (or, its coefficient of reflectivity is much lower as compared to tissue which is not spotted by black ink), so that a weaker level of light than the previously reflected light is detected by the optical detector 345c.

Furthermore, the optical detector 345c transmits a voltage output which corresponds to the level of the light which is incident upon it to the control section 344. The control section 344 decides whether the voltage output is a signal from tissue upon which a spot of black ink has been made, or whether it is a signal from tissue upon which a spot of black ink has not been made. If the control section 344 has decided that it is a signal from tissue upon which a spot of black ink has been made, then a counter not shown in the figures which is provided internally to the control section 344 is incremented by 1. Therefore, it is possible to count the markings M.

Furthermore although, in this embodiment, spots of black ink are used, the same beneficial results can also be obtained by using a element of any color, provided that it can be detected. As one example, methylene blue or the like is a dye which may be used for endoscope examination. Even further, it will be acceptable to select the detection wavelength region of the optical detector 345c when doing this to be the most suitable one. Yet further, it would also be acceptable to utilize a drug which includes a material which generates fluorescence for the marking M. In this case, it would be acceptable to use a light emitting element 345a which is made to generate light of a wavelength which excites this fluorescence, and to utilize an optical detector 345c which detects light of the wavelength of the fluorescence which is generated.

Furthermore, it would be acceptable to utilize a drug which contained a radioactive isotope for the marking M. In this case, it would be acceptable to utilize a scintillator or the like as the sensor 345.

Yet further, it would also be acceptable to utilize a drug which contained a magnetic material for the marking M. Moreover, it would be acceptable to utilize a magnetic substance itself, instead of such a drug. In this case, it would be acceptable to utilize a magnetic sensor as the sensor 345.

Even further, it would also be acceptable to utilize a metallic material for the marking M. As for the operation in this case, it will be explained in an embodiment to be described hereinafter.

Still further, the control section 344 includes a memory 344a which stores in advance a specified marking M which is an indicator which shows the position of the diseased part X as the number of the marking M, and the control section 344 is equipped with the function of counting the markings M which have been detected by the sensor 345, and causing the heater 348 to operate to apply heat when this count agrees with the number which is stored in the memory 344a. In other words, the control section 344 decides whether or not the marking M which has been detected by the sensor 345 is the specified marking.

The application of medication with the drug A to a diseased part X within the living body P with the capsule medication administration system 301, the capsule for medication 310, and the capsule type medical device 323 will now be explained in the following.

Figure 22:
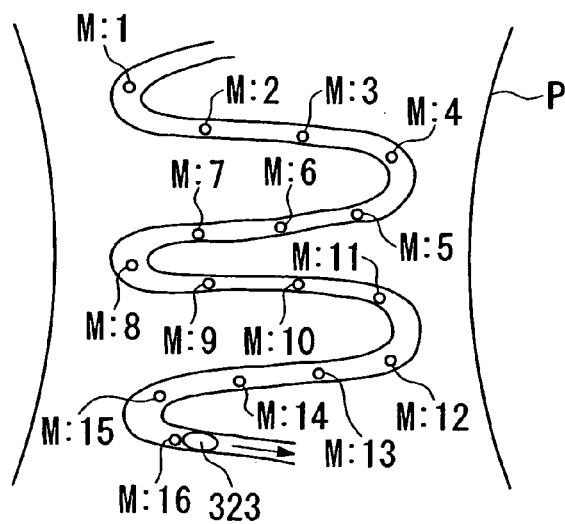
FIG. 22 is a view showing a situation in which a marking is made internally to the patient by a capsule type medical device.

First, at a medical facility such as a hospital or the like, the patient P swallows and orally ingests the capsule type medical device 323 upon the instructions of a physician. At this time, a switch of the capsule type medical device 323 which is not shown in the figures is turned on upon this ingestion, and the control processing section 332, to which electrical power is now supplied from the battery 334, starts to operate. While the capsule type medical device 323 which has been orally ingested shifts within the living body P as shown in FIG. 22, the control processing section 332 operates the discharge mechanism 322, and markings M are made within the digestive organs of the patient, for example at the rate of one every five seconds. In other words, the control processing section 332 sends an operating signal or the like to the piezo element 331, which expands. Due to this, the reservoir 330 is pressed upon, and the marking material W is discharged from the discharge aperture 329, thus making a marking M within the digestive organs. Furthermore, at the same time, the control processing section 332 causes the observation system 321 to operate, and acquires in-vivo information as images of the various internal parts of his body which are formed, for example, twice every second. Moreover, the control processing section 332 establishes a correspondence between the information which it has acquired about the living body with the observation system 321 and the positions of the markings M, and stores this successively in the memory 333.

The observation of the interior of the living body has been completed by excretion of the capsule type medical device 323, then the capsule type medical device 323 is retrieved. After this retrieval, the in-vivo information which has been stored in the memory 333 in correspondence with the positions of the markings M is inputted to the PC 324 shown in FIG. 17.

In other words, after having retrieved the capsule for observation 10 which has been excreted from the living body P, it is stored in the vessel 336. By storing it in the vessel 336, it is possible to perform the subsequent operations without the person who is performing the operations experiencing any feeling of uncleanliness. When the vessel 336 is placed in the vessel installation section 337, the placement detection switch 337b goes to ON. Due to this, the switch 337a goes to ON, and the electrical power supply device 338 and the wireless reception device 339 are driven. When the electrical power supply device 338 is driven, electrical power is supplied towards the capsule type medical device 323. The electrical power reception device 340 of the capsule type medical device 323 receives this electrical power which has been supplied, and supplies it by distributing it to the wireless transmission device 313 and the memory 333. When the wireless transmission device 313 receives the electrical power, it transmits the in-vivo information which it has accumulated towards the observational information receiver 325. The wireless transmission device 36, along with receiving the in-vivo information which has been transmitted, also transmits it via the cable 335 to the PC 324.

The operator checks the in-vivo information which has been received by the PC 324 and determines the position for medication. Furthermore, since this in-vivo information is stored in correspondence with the positions (the numbers) of the markings M, accordingly, when determining the position for medication, it is possible directly to decide from which numbered marking M it is appropriate to start medication. This decision as to the number of the marking M may be made by the operator, or the PC 324 may be so constituted as automatically to recognize the numbers of the markings M, as described hereinafter, to set it into the capsule for medication 310.

It should be understood that although, in this embodiment, the wireless transmission device 313 utilizes a transmission method which employs electromagnetic waves, the transmission method may be implemented with a method other than one which employs electromagnetic waves. For example, it would also be possible to transmit the in-vivo information via infrared communication by, along with making the capsule type medical device 323 and the vessel 336 from a material which is transparent to infrared radiation, also providing an infrared sensor to the observational information receiver 325 in such a manner that it is oriented towards an infrared light emitting element which is provided in the capsule type medical device 323, when the vessel 336 is put into the vessel installation section 337.

Furthermore, the operator such as a physician or the like performs diagnosis as to whether any abnormality is present in the living body, based upon the photographic images which have been inputted to the PC 324, which are the in-vivo information. If the result is that he has detected a lesion or the like upon the photographic images, then he specifies from the lesion or the like the diseased part X such as a superficial disorder or the like for which medication is required. After having specified the diseased part X, the physician specifies the marking M which indicates the position of the diseased part X. In other words, since the in-vivo information and the positions of the markings M are sent with a correspondence having been established between them, the specification of the marking M which is correlated with the in-vivo information may be performed from the in-vivo information in which the diseased part X is specified. In other words, the specified marking M is specified by the number of the marking M, i.e. which of the markings M in series it is.

Figure 23:
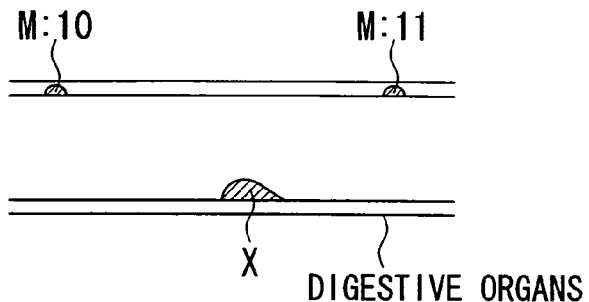
FIG. 23 is a view showing a situation in which a diseased part is positioned between a tenth marking and an eleventh marking.

It should be understood that, in the explanation of this embodiment, as shown in FIG. 23, it has been supposed that the position of the diseased part is between the tenth marking M and the eleventh marking M, and thus the specified marking M which indicates the position of the diseased part X is supposed to be the tenth marking.

Next, as shown in FIG. 17, the physician loads the capsule for medication 310 into the communicator 346 which is connected to the PC 324, and inputs the information for the specified marking M from the PC 324 to the memory 344a as a set value. In other words, data which specifies that the tenth marking M is the specified marking M is transmitted via the communicator 346 from the PC 324 to the capsule for medication 310 which has been loaded into the communicator 346. After this input, the patient P receives the capsule for medication 310 from the physician or the like. It should be understood that, after having received the capsule for medication 310, the patient P may leave the medical facility.

After this, the patient P swallows and orally ingests the capsule for medication 310 according to his medication schedule which has been prescribed. While shifting through the living body, the sensor 345 of the capsule for medication 310 which has thus been orally ingested detects the markings M which have been made by the capsule type medical device 323. The sensor 345 acquires information about the lumen, and decisions as to the presence or absence of markings M are made by the control section 344.

The control section 344 compares together the information for the markings M and the information for the specified marking M which is set in advance in the memory 344a, and makes decisions based thereupon. In other words, the control section 344 decides whether or not this marking M is the specified one, by counting the number of markings M which have been sent and have arrived. Since it has been set in advance that the specified marking is the tenth marking M, it decides, for example, that the initially detected marking M is not the specified marking M. Furthermore, since according to the count the next marking M which is sent and arrives is the second marking M, it similarly decides that this is not the specified marking M.

In this manner, the capsule for medication 310 shifts within the living body while detecting the various markings M.

Thus, when the capsule for medication 310 has detected the tenth marking M, the control section 344 decides according to the count that this marking M which has been sent is the tenth marking M, in other words that this is the specified marking M, and causes the heater 348 to operate. Upon receipt of a signal from the control section 344, the heater 348 applies heat momentarily so as to cause gas bubbles to be generated, and the thin membrane over the drug aperture 347 is ruptured by the pressure of these gas bubbles.

Figure 24:
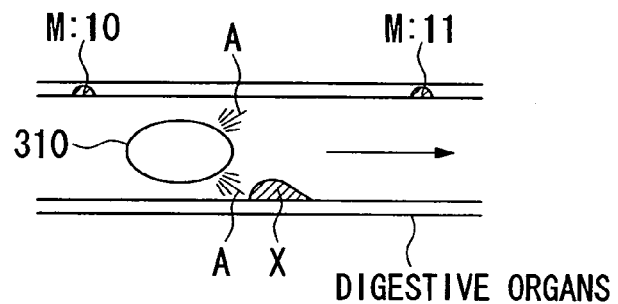
FIG. 24 is a view showing a situation in which the capsule for medication detects a tenth marking (a specified marking) and releases a drug.

As shown in FIG. 24, when the thin membrane over the drug aperture 347 is broken, the drug A within the reservoir 342 is released to the exterior of the casing 341 from the drug aperture 347. In other words, since the specified marking M indicates the position of the diseased part X, it is possible to apply the medication directly to the diseased part X.

According to the capsule medication administration system 301, the capsule for medication 310, and the capsule type medical device 323 described above, by orally ingesting the capsule type medical device 323, the acquisition of the in-vivo information is performed while leaving the markings M within the coelom, and reception of the in-vivo information and the information about the markings M is performed by the PC 324 via the wireless transmission device 313. Based upon these items of information, it is easily possible to detect the diseased part X within the living body from the markings M. Furthermore, by subsequently orally ingesting the capsule for medication 310, release of the drug A is performed at the position of the specified marking M at which medication is to be administered. In this manner, along with it being possible to approach the desired site (the diseased part) within the coelom easily and moreover directly, it is also possible to administer the medication there. Furthermore, since the medication is not performed upon detection of the diseased part X, but rather is performed upon detection of the specified marking M, accordingly it does not happen that the diseased part X is passed by before the medication has been administered; rather, it is possible to apply the medication efficiently to the diseased part X.

Furthermore, since the indicator which indicates the position of the diseased part is not some shape or color or the like which is a characteristic sign within the living body, but rather is made by the capsule type medical device 323 as a marking, therefore it is possible to make this indicator more precisely and distinctly. Accordingly it is possible to enhance the reliability of the medication, since the sensor 345 performs the detection of the marking (the specified marking) certainly and moreover at high accuracy.

Yet further, since the medical device 320 is constituted by the capsule type medical device 323, accordingly it is possible for the patient P simply and conveniently to orally ingest it.

Even further, the control section 344 counts the number of the markings which have been detected by the sensor 345, and, when this agrees with the number which is stored in advance in the memory 344a, decides that this marking M which has now been detected is the specified marking, and performs release of the drug A. Since the control section 344 decides upon the specified marking M simply according to the count of the markings M in this manner, accordingly there is no requirement to incorporate any complicated decision circuit, and, along with making it possible to build the structure easily, it is also possible to enhance the reliability, since the number of detection errors is reduced.

Furthermore although, in this embodiment, the in-vivo information which is accumulated in the memory 333 is extracted by retrieving the capsule type medical device 323 after it has been excreted from the living body, it would also be acceptable to arrange the construction so that this information is transmitted using a wireless communication device to the exterior of the capsule upon demand, while observing the living body.

Figure 25:
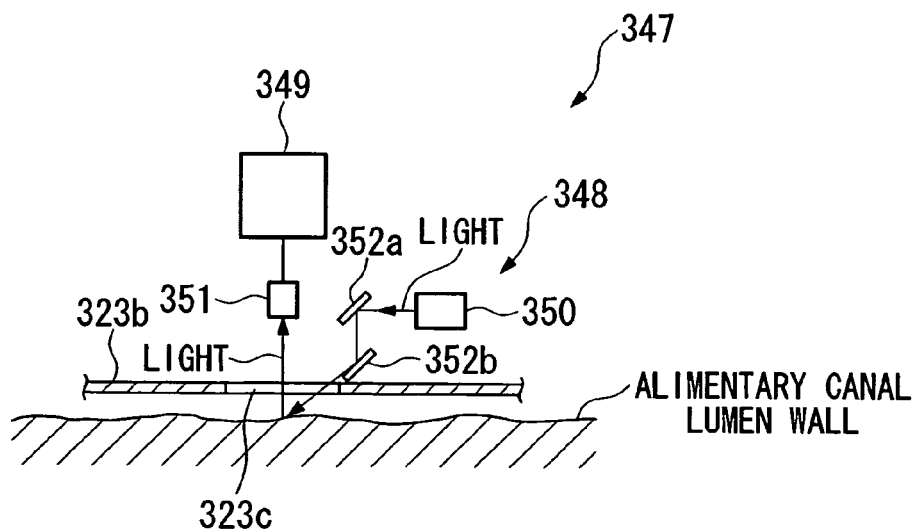
FIG. 25 is one structural view of a measurement device for observation, which is a device which is attached when making markings at a predetermined moving distance interval, and which is attached within a casing of the capsule type medical device shown in FIG. 16.

Furthermore although, in this embodiment, it is arranged to make the markings M intermittently at fixed intervals, they may be made at intervals which are not fixed. For example, it would be acceptable to provide the markings M within the living body at intervals of constant shifting distance. In this case, for example, it would be proper to provide a measurement device for observation 347 (a shift amount detection device) within the casing 323b, as shown in FIG. 25. This measurement device for observation 347 includes an information acquisition device 348 which acquires surface images, which are surface information about the alimentary canal lumen wall within the living body, and an image processing section 349 which calculates the moving distance based upon the change with the passage of time of the surface information which has been acquired by this information acquisition device 348. Furthermore, the information acquisition device 348 includes LEDs 350 which emit light L against the surface of the alimentary canal lumen wall, and an optical sensor 351 which captures images of the light L which has been reflected back from the surface of the alimentary canal lumen wall, in other words surface images. The LEDs 350 are arranged, for example, horizontally, so as to emit the light L along the axial direction of the casing 323b. Furthermore, the direction of the light L which has been emitted is changed by reflecting mirrors 352a and 352b, and is emitted at a slanting angle against the surface of the alimentary canal lumen wall.

Yet further, the optical sensor 351 is arranged in such a position as to be able to received the light L which has been reflected. It should be understood that it would also be acceptable to provide a transparent cover 323c to the casing 323b near the information acquisition device 348, so that the light L is able to pass through it optically.

The image processing section 349, along with photographing (scanning) the surface images of the alimentary canal lumen wall which have been captured by the optical sensor 351 at a high speed of, for example, 1500 to 6000 times in each second, also notices the characteristics of the images which have been photographed, such as their color or shape or the like, and to calculate the moving distance from the changes over the passage of time of these parameters. It will be acceptable for it to be so constructed as to inform the control processing section 332 of the moving distance which it has thus calculated. Therefore, the control processing section 332, as described above, is able to make the markings M by operating the discharge mechanism 322 at successive constant moving distances within the living body.

By making the markings M at a fixed moving distance in this manner, it is possible to make the markings M within the coelom without any of the markings M coming too close to one another.

Moreover, it would also be acceptable to provide a position sensor within the casing 323b, and to make the markings M at fixed intervals based upon the output of this position sensor. In this case, it would be possible to utilize for this position sensor, for example, an AURORA from the NDI company or the like.

Next, the fifth embodiment of the capsule medication administration system according to the present invention will be explained with reference to FIG. 26 and FIG. 27. It should be understood that, to structural elements which are the same as those in the various embodiments described above, the same reference symbols are appended, and the explanation thereof is curtailed.

Figure 26:
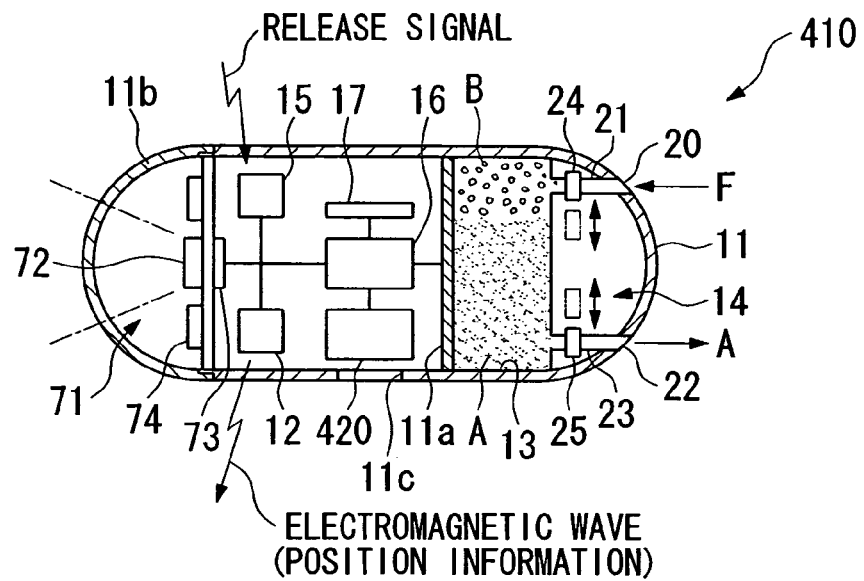
FIG. 26 is a sectional view showing a capsule for medication which is used in a fifth embodiment of the capsule medication administration system according to the present invention.

As shown in FIG. 26, the capsule for medication 410 (the capsule type medical device) of this embodiment includes, within its casing 11, in addition to an image formation device 71, a measurement section 420 which measures its moving distance within the living body.

Figure 27:
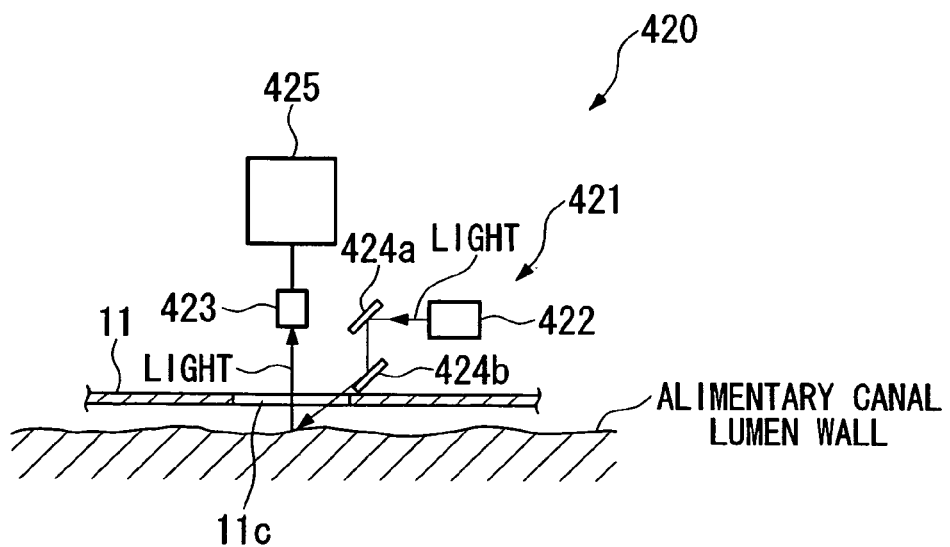
FIG. 27 is a structural view showing a measurement section of the capsule for medication shown in FIG. 26.

As shown in FIG. 27, the measurement section 420 includes an image acquisition section 421 which acquires surface images of the alimentary canal lumen wall within the living body, and an image processing section 425 (a traversed distance calculation device) for the surface information which has been acquired by the image acquisition section 421.

The image acquisition section 421 includes the image processing section 425, LEDs 422 which emit light against the surface of the alimentary canal lumen wall, and an optical sensor 423 which captures an image of the light which is reflected back from the surface of the alimentary canal lumen wall, in other words a surface image. The LEDs 422 are arranged horizontally so as to emit their light in the axial direction of the casing 11. Furthermore, the direction of emission of the light which has been emitted in the axial direction of the casing 11 is changed by reflective mirrors 424a and 424b, and thus this light is emitted at a slanting angle towards the surface of the alimentary canal lumen wall. Yet further, the optical sensor 423 is positioned so as to be able to receive the light which is reflected. It should be understood that a transparent cover 11c is provided to the casing 11 near the image acquisition section 421, so as to allow light to pass optically.

The image processing section 425, along with photographing the surface images of the alimentary canal lumen wall which have been captured by the optical sensor 423 at a high speed of, for example, 1500 to 6000 times in each second, also calculates the shift amount from the changes over the passage of time of the patterns of these images which have been photographed. Furthermore, the image processing section 425 sends the shift amount which has been calculated to the information transmission section 12. Yet further, the information transmission section 12 of this embodiment transmits the shift amount which has been measured by the measurement section 420 and the photographic images which have been formed by the image formation device 71 to the exterior of the living body while establishing a correspondence between them. This data which is transmitted is received by the reception section 50 external to the living body of the external device 35, and is sent to the decision section 51. In the decision section 51, the moving distance of the capsule for medication 410 after orally ingesting is obtained by integrating the shift amounts which are sent moment by moment.

By orally ingesting the capsule for medication 410 which has the above type of structure, the decision section 51 of the external device 35 compares together the position information for the diseased part X, in other words the variation of the image information in correspondence to the insertion distance of the insertion section 76, and the position information for the capsule for medication 410, in other words the variation of the image information from the image formation device in correspondence to the moving distance which has been obtained by the decision section 51 from the shift amount which has been measured by the measurement section 420, and, when it has been decided that these two items of information are highly alike, the decision section 51 decides that the capsule for medication 410 has arrived near the position of the diseased part X. The subsequent operation is the same as that described above.

By recording in correspondence with one another the image information and the positional information for the diseased part X which have been accurately specified by the endoscope device which is utilized as the specification device 231, and by recording the moving distance of the capsule for medication 410 and the image information in correspondence with one another, it is made possible to compare together these two types of information easily.

Therefore, it is possible easily to cause the information about the diseased part X to be reflected in the medication position of the capsule for medication 410, and it is possible to administer the medication to the diseased part X which has been accurately specified by the endoscope device.

Furthermore, in this embodiment, since the measurement section 420 is provided, it is possible to obtain the moving distance of the capsule for medication 410 more accurately. Therefore, it is possible to perform the release of the drug A in a more effective manner.

Next, a variant example of this embodiment will be explained with reference to FIG. 28 through FIG. 30. In this variant embodiment, as shown in FIG. 28, in addition to the capsule for observation 430 and the capsule for medication 440 which are orally ingested, there is also provided a unit 450 external to the living body, which is disposed externally to the living body.

Figure 29:
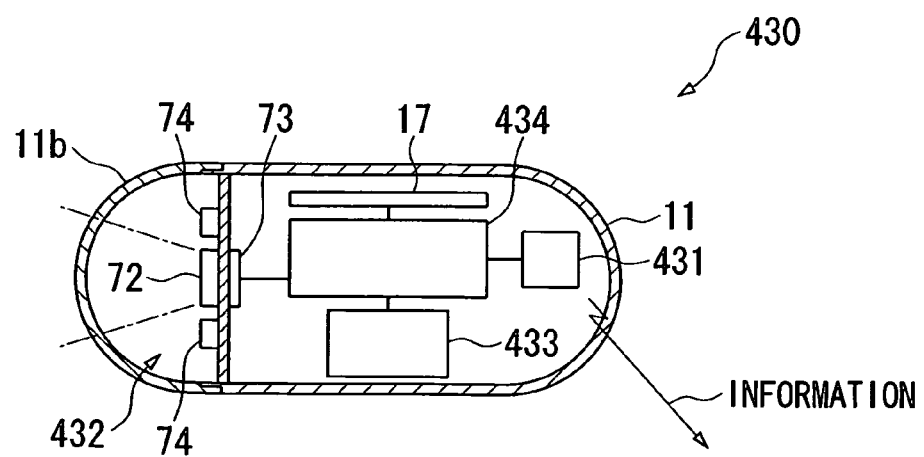
FIG. 29 is a sectional view showing a capsule for observation which is used by the capsule medication administration system shown in FIG. 28.

As shown in FIG. 29, the capsule for observation 430 includes a transmission antenna 431 (a transmission device). This transmission antenna 431 transmits the in-vivo information which has been acquired by the observation device 432 and the moving distance which has been measured by a measurement device 433 for observation to the unit 450 external to the living body with a correspondence being established between them. In other words, the control section 434, along with performing predetermined processing upon the in-vivo information which has been sent from the observation device 43, also transmits this in-vivo information and the moving distance which has been sent from the image processing section from the transmission antenna 431 with a correspondence being established between them.

Figure 28:
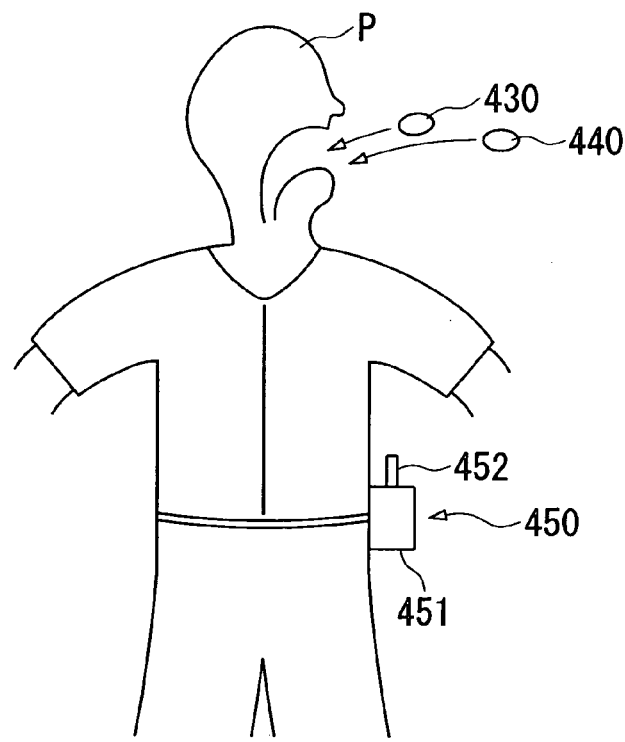
FIG. 28 is a schematic figure showing a variant example of the fifth embodiment of the capsule medication administration system according to the present invention.
Figure 30:
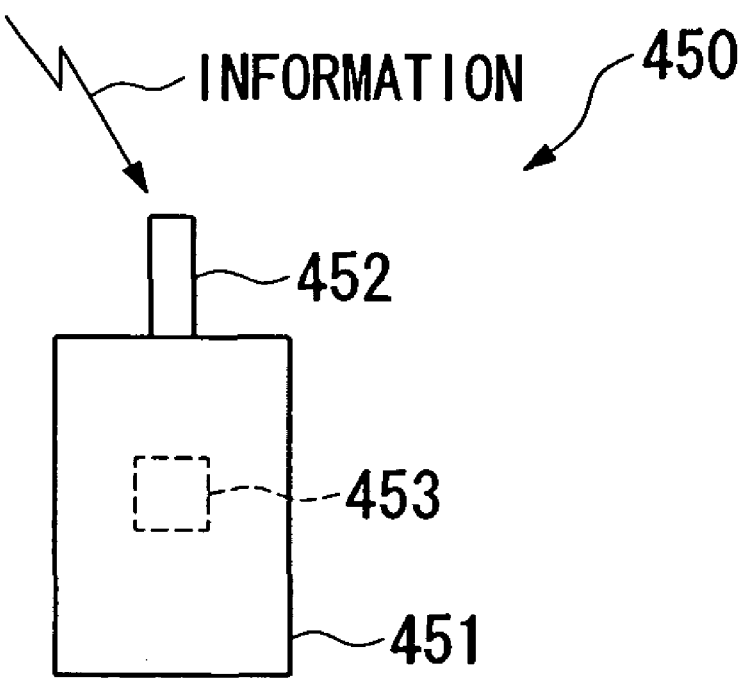
FIG. 30 is a structural view showing a unit external to the living body which is used by the capsule medication administration system shown in FIG. 28.

As shown in FIG. 28 and FIG. 30, the unit 450 external to the living body includes, in a main body 451 which can be put on to the living body P, a reception antenna (a reception device) 452 which receives the information which has been transmitted from the transmission antenna 431 of the capsule for medication 70, and a specification section 453 (a specification mean) which specifies the diseased part X for which medication is required and the moving distance to the diseased part X, based upon the information which has been received by the reception antenna 452.

The main body 451 is capable of being put on to the exterior of the living body P by his fitting a belt or the like. The reception antenna 452, for example, is provided so as to project from the main body 451, and is equipped with the function of sending the information which it has received to the specification section 453. Furthermore the specification section 453 detects, for example, red color from among the photographic image which has been sent and has arrived, which is in-vivo information, and compares this detected amount with a threshold value which is set in advance. If the detected amount is greater than or equal to the threshold value, the specification section 453 specifies that as being a hemorrhagic site (a diseased part X) for which medication is required. Yet further, the specification section 453 specifies the moving distance from the mouth of the patient P to the diseased part X, based upon the in-vivo information which specifies the diseased part X and the moving distance which has been established in correspondence with the in-vivo information which has been sent via the reception antenna 452.

It should be understood that, in this embodiment, it is arranged for the moving distance which is specified by the specification section 453 of the unit external to the living body 450 is recorded in the memory of the capsule for medication 440.

The case of administration of medication with a drug A to a diseased part X within the living body P with the capsule medication administration system of this type of structure will now be explained in the following.

When the capsule for observation 430 which has been orally ingested by the patient P is shifting around within his body, it acquires in-vivo information, i.e. photographic images, with the observation device 432, and it measures the moving distance within the living body with the measurement device for observation 433. Furthermore, the control section 434 establishes a correspondence between the in-vivo information and the moving distance, and transmits it towards the unit 450 external to the living body from the transmission antenna 431.

The reception antenna 452 of the unit 450 external to the living body, receives the information which has been transmitted from the transmission antenna 431, and sends it to the specification section 453. The specification section 453 detects only the red color from among the photographic image which has been sent by comparing this detected amount with a threshold value which has been set in advance, and specifies the diseased part X for which medication is required. After having specified the diseased part X, the specification section 453 specifies the moving distance from the mouth of the patient P to the position of this diseased part X.

Next, the moving distance which has been specified by the specification section 453 is stored in the memory of the capsule for medication 440. After this input, and after the observation by the capsule for observation 430 has been terminated by a predetermined time period elapsing from the oral ingestion of the capsule for observation 430, or by the patient excreting the capsule for observation 430 or the like, then the patient P orally ingests the capsule for medication 440 according to a medication schedule which has been determined. Due to this oral ingestion of the capsule for medication 440, the drug A is released at the moving distance which has been specified, in other words at the position of the diseased part X, it is possible to administer the medication to the diseased part X in an assured manner. In particular, since the unit 450 external to the living body specifies the diseased part X and the moving distance to the diseased part X, accordingly it is possible to make the capsule for observation 430 of a simple structure, so that it is possible to anticipate an improvement in its compactness.

Next, the sixth embodiment of the capsule medication administration system according to the present invention will be explained with reference to FIG. 31 through FIG. 33. It should be understood that, to structural elements which are the same as those in the various embodiments described above, the same reference symbols are appended, and the explanation thereof is curtailed.

As shown in FIG. 31, the capsule medication administration system 501 of this embodiment includes a capsule for medication 510, and a unit 520 external to the living body which includes an endoscope device as a specification device 231.

Figure 32:
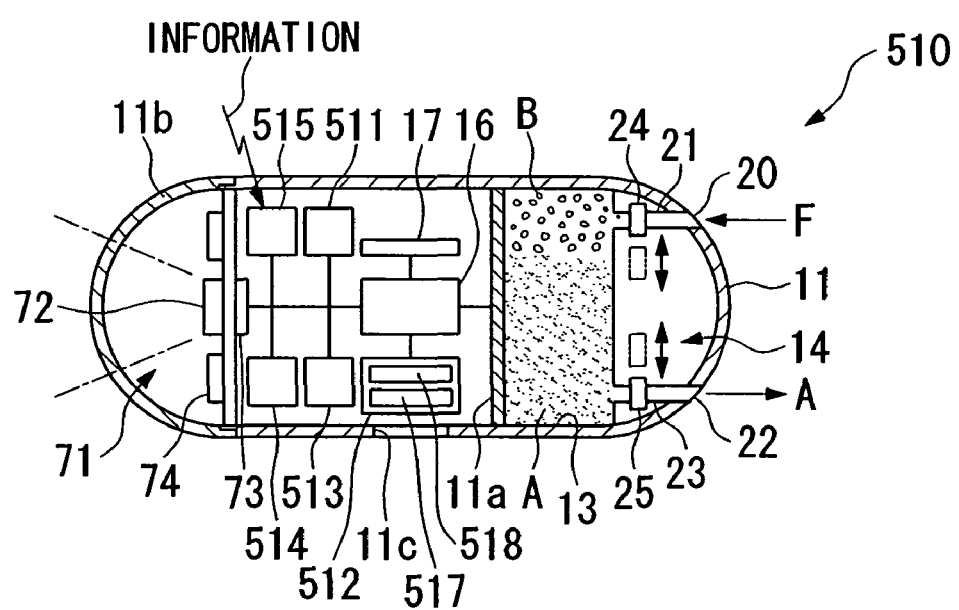
FIG. 32 is a sectional view showing a capsule for medication which is used by the capsule medication administration system shown in FIG. 31.
Figure 33:
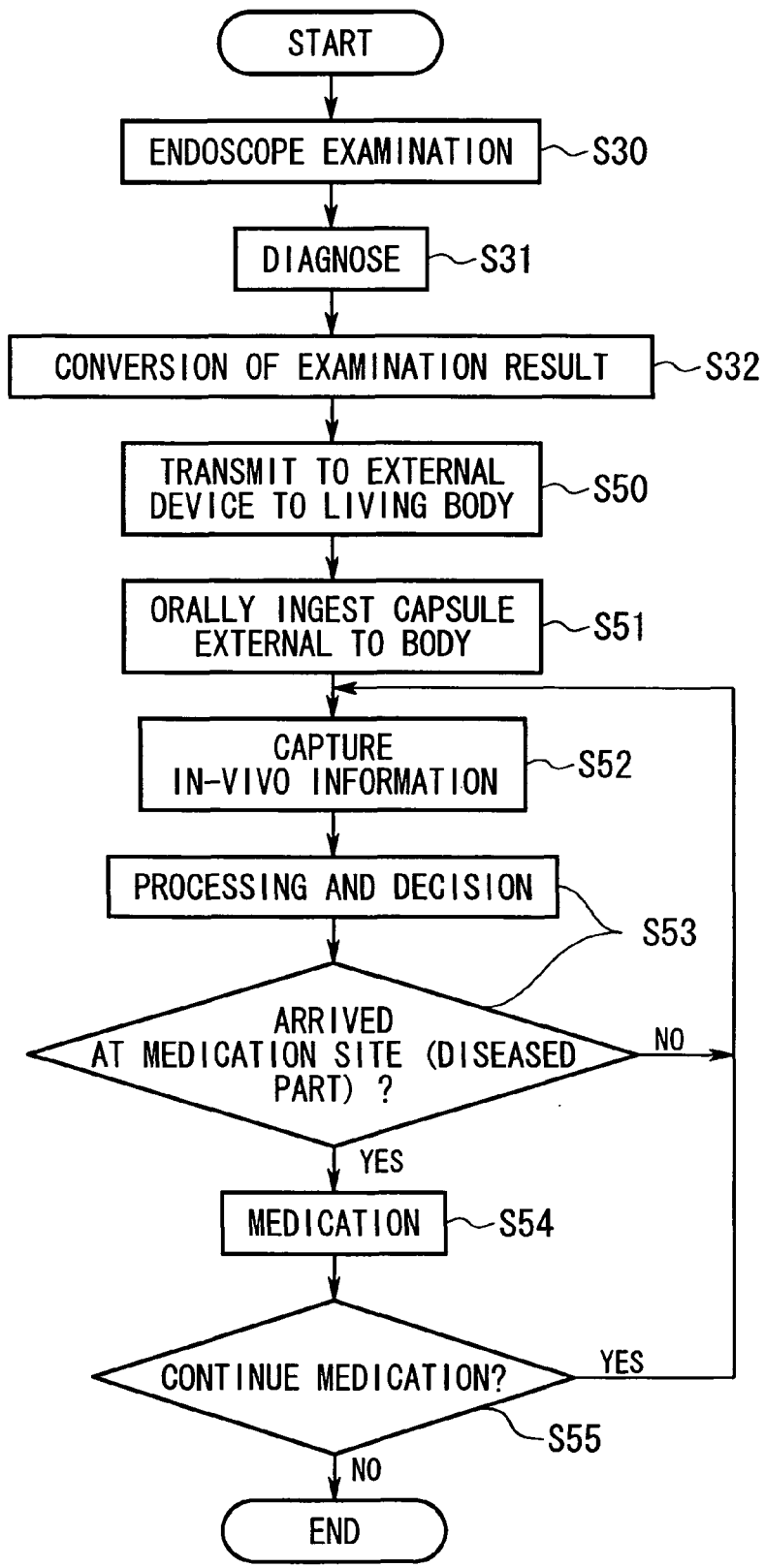
FIG. 33 is a flow chart for the case of performing medication for a diseased part X with the capsule medication administration system shown in FIG. 31.

As shown in FIG. 32, the capsule for medication 510 includes a memory 511 within its capsule which is recorded information about a diseased part X that has been specified by the specification device 231, a shift amount detection section 512 (a detection section) which detects its own position by detecting the shift amount of the capsule for medication 510 itself within the living body, an image formation device 71 which forms images of the interior of the living body, a decision section 513 (a decision section) within the capsule which decides whether or not to administer medication, a timer circuit 514, and an in-capsule reception section 515 which performs communication with the exterior of the living body and receives information to be written into a memory 511 in the capsule.

Furthermore, as shown in FIG. 31, an internal wireless transmission section 516 is provided with a PC 83 which is connected to the endoscope device which serves as the specification device 231, and it is possible to transmit data to the in-capsule reception section 515.

The image formation device 71 and the shift amount detection section 512 operate at fixed intervals upon a clock signal of a timer circuit 514. The image information which is obtained by the image formation device 71 and the shift amount information which is obtained by the shift amount detection section 512 are sent to the in-capsule decision section 513. The information relating to the diseased part X which has been obtained by the endoscope device is subjected to conversion processing as shown in FIG. 13 by the PC 83. Then the information is transmitted to the in-capsule reception section 515 and is recorded in the in-capsule memory 511.

As shown in FIG. 18, the shift amount detection section 512 includes a measurement section 517 and a multiplication section 518, and it is made so that the shift amount in a short interval of time is obtained by the measurement section 517, while it is possible to detect the total shift amount of the capsule for medication 510 within the coelom by integrating these shift amounts with the integration section 518.

The operation of medication with the drug A for the diseased part X within the living body P with the capsule medication administration system 501 of this type of structure will now be explained with reference to FIG. 33.

The diseased part X for which medication is required is specified by the specification device 231, and the data of the information relating the diseased body X, then this data is recorded in the in-capsule memory 511 of the capsule for medication 510 by data transmission and the like between the wireless transmission section 516 within the PC and the in-capsule reception section 515 (S50).

After this, the patient P orally ingests the capsule for medication 510 (S51). Furthermore, when the capsule for medication 510 is orally ingested, by a switch which is not shown in the figures being turned on, electrical power is supplied to the various structural components from the battery 17, and the operation of the capsule for medication 510 is started based upon the operational timing of the timer circuit 514.

The capsule for medication 510 which has been thus orally ingested shifts while forming images of the inside of the living body with the image formation device 71 (S52). The photographic images which have been formed by this image formation device 71 are sent to the in-capsule decision section 513. The shift amount detection section 512 sends the shift amount information to the in-capsule decision section 513. The in-capsule decision section 513 performs predetermined processing upon the shift amount information for itself (for the capsule for medication 510 itself) which has been sent, compares this shift amount information with the photographic image information for the diseased part X which has been converted and is recorded in the in-capsule memory 511, and makes a decision as to whether or not the capsule for medication 510 has arrived at the vicinity of the diseased part X (S53). For example, the decision section 133 may decide that the capsule for medication 510 has arrived at the vicinity of the diseased part X, and may inform the control section to that effect, if the images which have been formed by the image acquisition device 77 of the specification device 231 and by the image formation device 71 are alike, and the shift amount of the capsule for medication 510 is close to the insertion amount of the endoscope device 100, or if the variation over time of the brightness or the variation over time of the color balance of the photographic images which have been formed by the image acquisition device 77 and by the image formation device 71 are alike. Upon receipt of this information, the control section 16 causes both the opening and closing valves 24 and 25 to operate, thus performing release of the drug A (S54).

It should be understood that, if the specification device 231 has specified a plurality of diseased parts X, then the in-capsule decision section 513 decides whether or not medication has been applied to all of the diseased parts X (S55). If the result of this decision is that medication for all of the diseased parts X has been completed, then the operation is terminated. After this, the capsule for medication 510 is excreted and is retrieved.

As described above, since the control of the release of the drug A is performed in the interior of the capsule for medication 510, therefore there is no requirement for the patient P to put on any device external to his body. Accordingly, in addition to the benefits obtained by the various embodiments described above, there is the benefit that the freedom for the patient P is enhanced.

It should be understood that, in this embodiment, it would also be acceptable, instead of using the shift amount detection section 512, to obtain the total shift amount of the capsule for medication 510 by comparing together a plurality of images which have been acquired by the image formation device 71, by calculating the shift amount of the capsule for medication 510 between frames, and by integrating these.

A variant example of this embodiment will now be explained with reference to FIG. 34 through FIG. 40.

Figure 34:
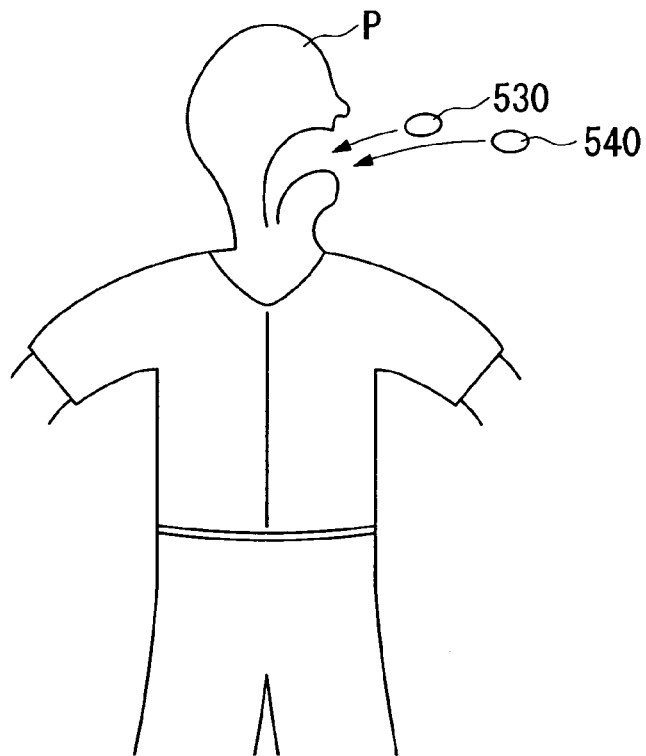
FIG. 34 is a schematic figure showing a variant example of the sixth embodiment of the capsule medication administration system according to the present invention.

As shown in FIG. 34, the capsule medication administration system of this variant example includes a capsule for observation 530 (a first capsule) for being orally ingested to within the living body P and acquiring in-vivo information, and a capsule for medication 540 (a second capsule) for administering medication.

Figure 35:
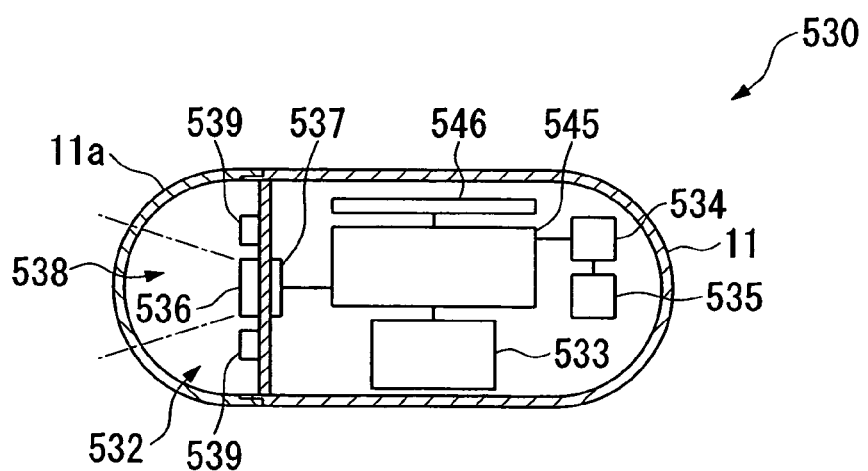
FIG. 35 is a sectional view showing a capsule for observation which is used in the capsule medication administration system shown in FIG. 34.

As shown in FIG. 35, the capsule for observation 530 includes, within a capsule shaped casing 11: an observation device 532 (acquisition device) which acquires photographic images, which are in-vivo information, by forming images of various internal portions of the living body; a measurement device for observation 533 which measures the moving distance within the living body; a memory 534 which records the moving distance which has been measured by the measurement device for observation 533 and the in-vivo information which has been acquired by the observation device 532 with a correspondence established between them; and a specification section 535 which specifies a diseased part X for which medication is required and the moving distance to that diseased part X, based upon the in-vivo information which has been recorded in the memory 534.

The casing 11 is formed from a plastic material or the like so as to closely enclose its interior, and at one of its ends there is provided a transparent cover 11a. An objective lens 536 is disposed at the inside of this transparent cover 11a, and, at the focal position of this objective lens 536, there is provided an image formation element 537 which may be a CMOS imager or the like. This objective lens 536 and image formation element 537 constitute an image formation device 538 which forms images of the interior of the living body. Furthermore, around the perimeter of the objective lens 536, there are provided LEDs 539 (illumination device) which emit light for illumination, thus illuminating the visual field range of the objective lens 536. In other words, this image formation device 538 and these LEDs 539 constitute an observation device 532.

Figure 36:
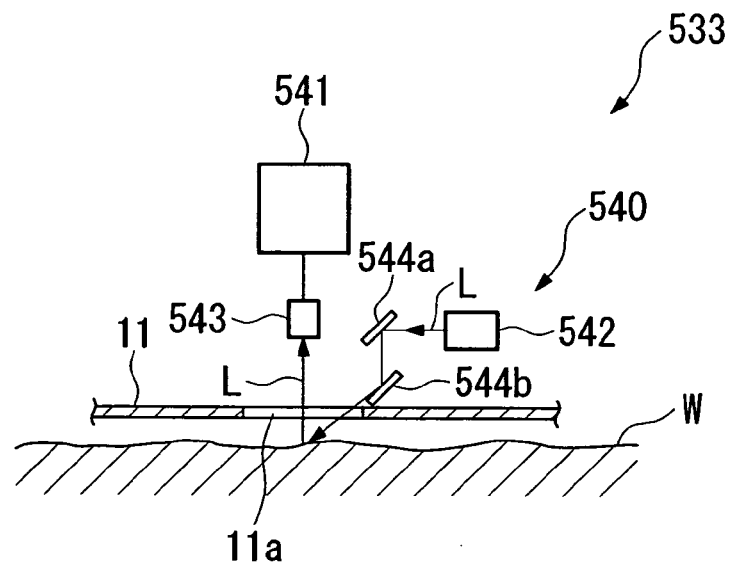
FIG. 36 is a structural view showing a measurement device for observation of the capsule for observation shown in FIG. 35.

As shown in FIG. 36, the measurement device for observation 533 includes an information acquisition device 540 which acquires surface images, which are surface information about the alimentary canal lumen wall W within the living body, and an image processing section 541 (a calculation device) which calculates the moving distance, based upon the variation along with the passage of time of the surface information which has been acquired by the information acquisition device 540.

The information acquisition device 540 includes LEDs 542 which emit light L against the surface of the alimentary canal lumen wall W, and an optical sensor 543 which captures an image of the light L which has been reflected back from the surface of the alimentary canal lumen wall W, in other words a surface image.

The LEDs 542 are provided horizontally so as to emit the light L along the axial direction of the casing 11. Furthermore, the direction of emission of this light L which has been emitted along the axial direction of the casing 11 is changed by reflective mirrors 544a and 544b, so that it comes to be emitted at a slanting angle against the surface of the alimentary canal lumen wall W. Yet further, the optical sensor 543 is disposed at a position for it to be able to receive the light L which has thus been reflected. It should be understood that the transparent cover 11a is provided to the surface casing 11 at the vicinity of the information acquisition device 540, so that the light L can pass through it optically.

The image processing section 541, along with photographing (scanning) the surface images of the alimentary canal lumen wall W which have been captured by the optical sensor 543 at a high speed of, for example, 1500 to 6000 times in each second, also pays attention to the specific characteristics of the images which have been photographed, such as their color or shape or the like, and to be able to calculate the shift amount from their variation over the passage of time. Furthermore, the image processing section 541 sends the moving distance which has been calculated to the control section 545.

The control section 545 is equipped with the function of, after the capsule has been ingested into the living body, along with causing the LEDs 542 to operate by sending a signal to them, also controlling the observation device 532 so that it forms images of the interior of the living body, for example twice per second randomly, thus taking in in-vivo information. Furthermore, the control section 545, along with performing predetermined processing upon the in-vivo information which has been sent from the observation device 532, also records this in-vivo information and the moving distance which has been sent from the image processing section 541 in the memory 534 with a correspondence being established between them.

The specification section 535 detects, for example, red color from among the in-vivo information which is stored in the memory 534, and compares the detected amount thereof with a threshold value which is determined in advance. Then if it is greater than that threshold value, it specifies that this is a hemorrhagic site (a diseased part X) for which medication is required. Furthermore, the specification section 535 specifies the moving distance to the position of this diseased part X, based upon the in-vivo information which indicates the diseased part X that has been specified, and the moving distance which is established in correspondence with the in-vivo information which is recorded in the memory 534.

Moreover, a battery 546 is housed within the casing 11 for supplying electrical power to these various structural components.

Figure 37:
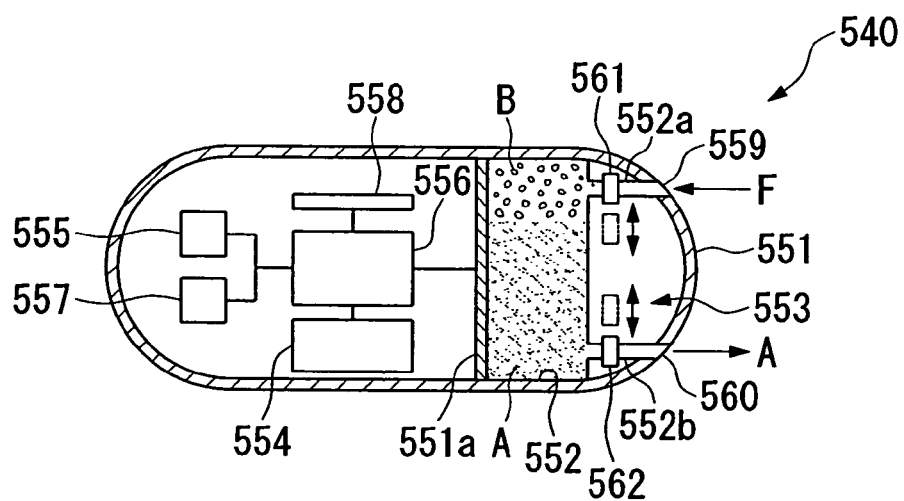
FIG. 37 is a sectional view showing a capsule for medication which is used in the capsule medication administration system shown in FIG. 34.

As shown in FIG. 37, the capsule for medication 550 includes, within a capsule shaped casing 551, a reservoir 552 (a drug retention section) which retains a drug A, a release device 553 which releases the drug A which is retained in the reservoir 552, a measurement device for medication 554 which measures the moving distance within the living body, a decision section 555 which decides whether or not the moving distance which has been measured by the measurement device for medication 554 is the moving distance which has been specified by the specification section 535 of the capsule for observation 530, a control section 556 (a control device) which causes the release device 553 to operate when the decision section 555 has decided that it is the moving distance which has been specified, a memory 557 which stores the moving distances which have been specified by the specification section 535 of the capsule for observation 530, and a battery 558 which supplies electrical power to these various structural components.

The casing 551 is formed from plastic or the like so as tightly to enclose its interior, and a reservoir 552 is provided at one end of its interior, surrounded by a wall portion 551a and the inner peripheral surface of the casing 551. A body fluid intake conduit 552a which includes a body fluid intake aperture 559 which opens to the outer surface of the casing 551, and a drug supply conduit 552b which includes a drug release aperture 560 which opens to the outer surface of the casing 551, are connected to the reservoir 552. It should be understood that the body fluid intake aperture 559 and the drug release aperture 560 are formed in plurality around the axis of the one end of the casing 551. Furthermore, to both of these conduits 552a and 552b, there are provided opening and closing valves 561 and 562, which can be shifted so as to open or close their respective ones of these conduits 552a and 552b.

Yet further, Into the interior of the reservoir 552, in addition to the drug A, there is charged an expandable chemical B, such as a foaming agent or the like, which has the characteristic of reacting and expanding when it comes into contact with a water component; and this chemical B is stored on the side of the body fluid intake conduit 552a. Moreover, the drug A is stored on the side of the drug supply conduit 552b, adjacent to the expandable chemical B. Thus, in more detail, it is possible, by operating the opening and closing valves 561 and 562, to take in body fluid F from the exterior of the casing 551 into the interior of the reservoir 552, thus causing the expandable chemical B to expand, so that the drug A is released to the exterior of the casing 551 due to the elevation of the pressure thereupon.

In other words, this body fluid intake conduit 552, a body fluid intake aperture 559, drug supply conduit 552b, drug release aperture 560, and the two opening and closing valves 561 and 562 constitute a release device 553.

It should be understood that, when storing the drug A within the reservoir 552, initially the expandable chemical B is loaded, and then, after this, by feeding in the drug A from the drug release aperture 560 so that the expandable chemical B overflows out from the body fluid intake aperture 559, it is possible to store the drug A within the reservoir 552 at high density.

Furthermore, the measurement device for medication 554, just like the measurement device for observation 533 shown in FIG. 36, includes an information acquisition device 540 and an image processing section 541. Yet further, the image processing section 541 sends the calculated moving distance to a decision section 555. This decision section 555 compares the moving distance which has been sent and which it has received with the specified moving distance which is recorded in the memory 557, and when it agrees with this specified moving distance, to send a message to this effect to the control section 556. Upon receipt thereof, the control section 556 causes both of the opening and closing valves 561 and 562 to operate. It should be understood that, in the initial state, both of the opening and closing valves 561 and 562 are set to their positions where they close off the conduits 552a and 552b.

Figure 38:
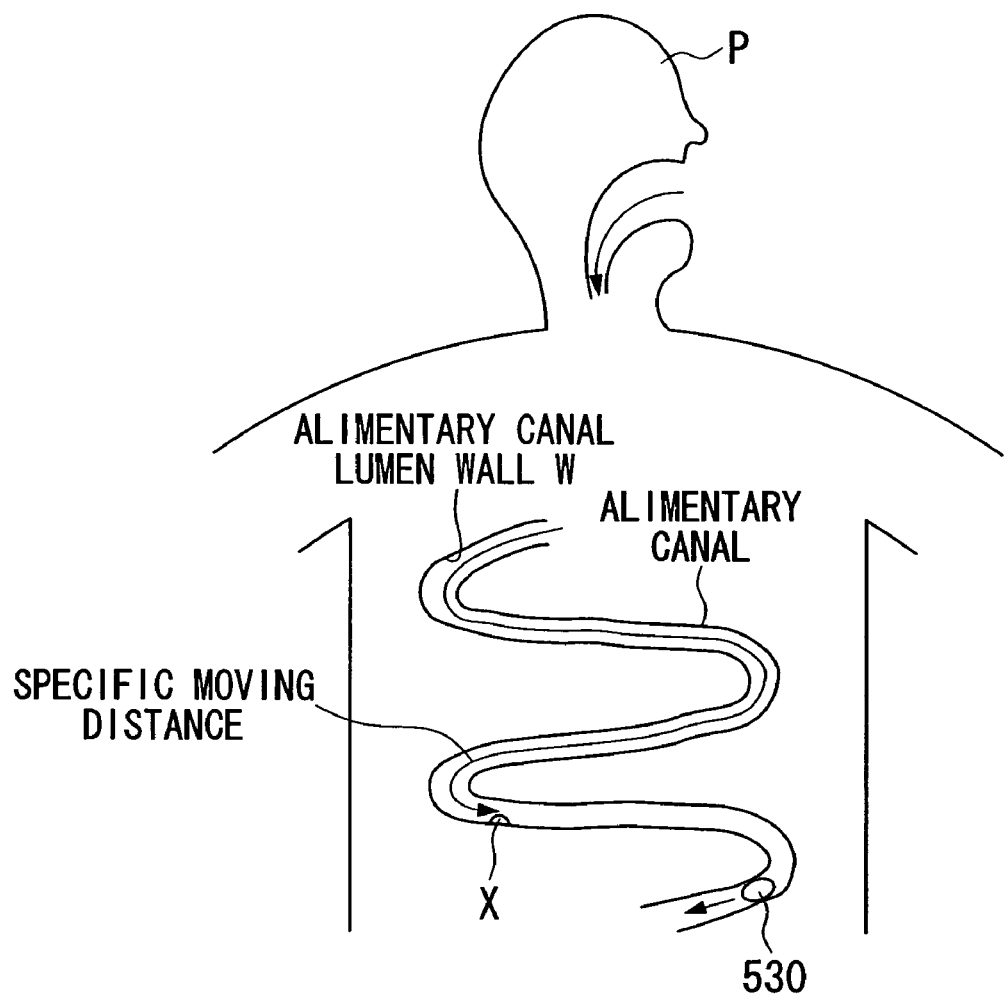
FIG. 38 is a view showing a situation in which a capsule for observation is orally ingested, and has specified a moving distance which indicates the position of a diseased part.
Figure 39:
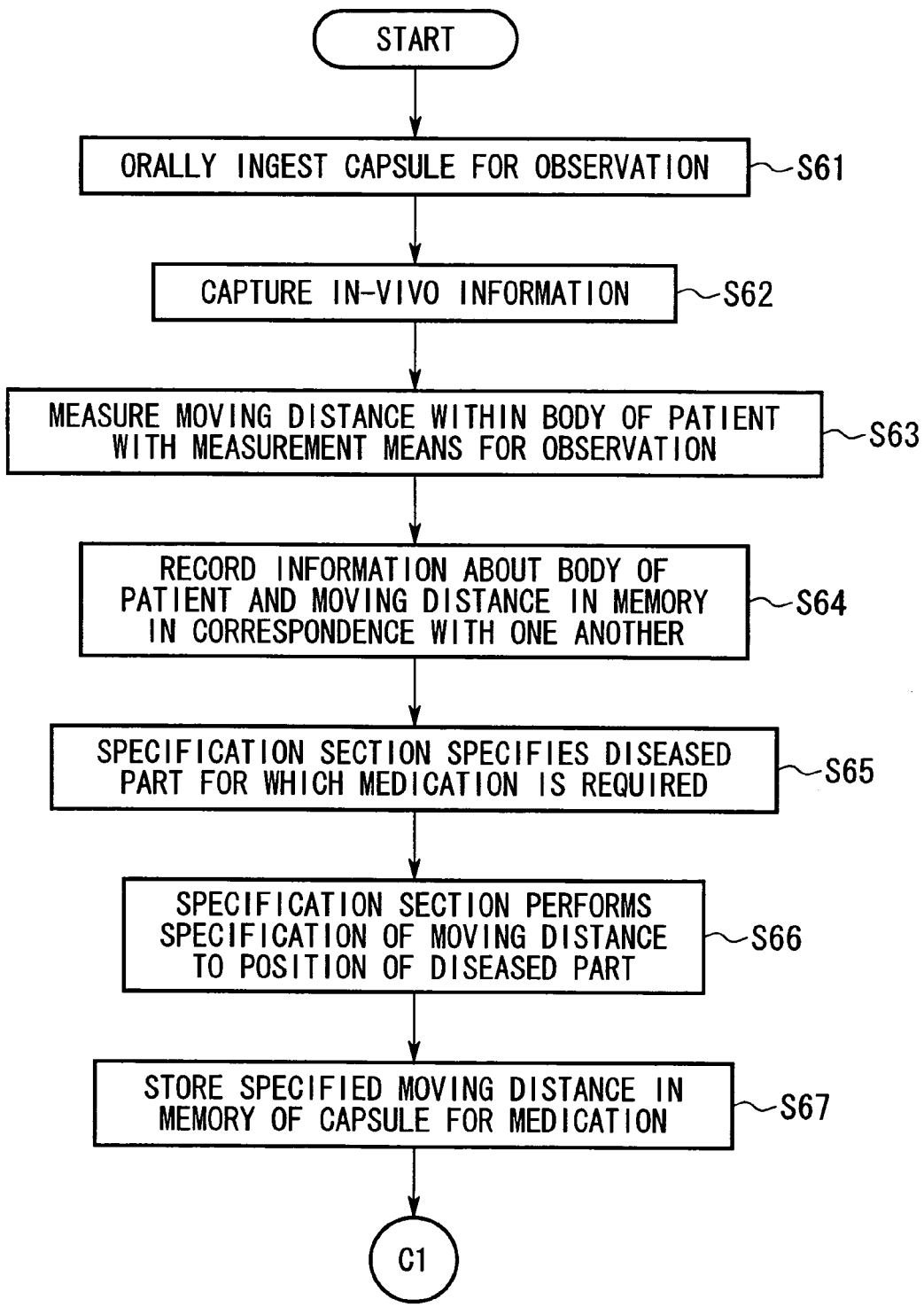
FIG. 39 is a flow chart for the case of performing medication for a diseased part with a capsule medication administration system.
Figure 40:
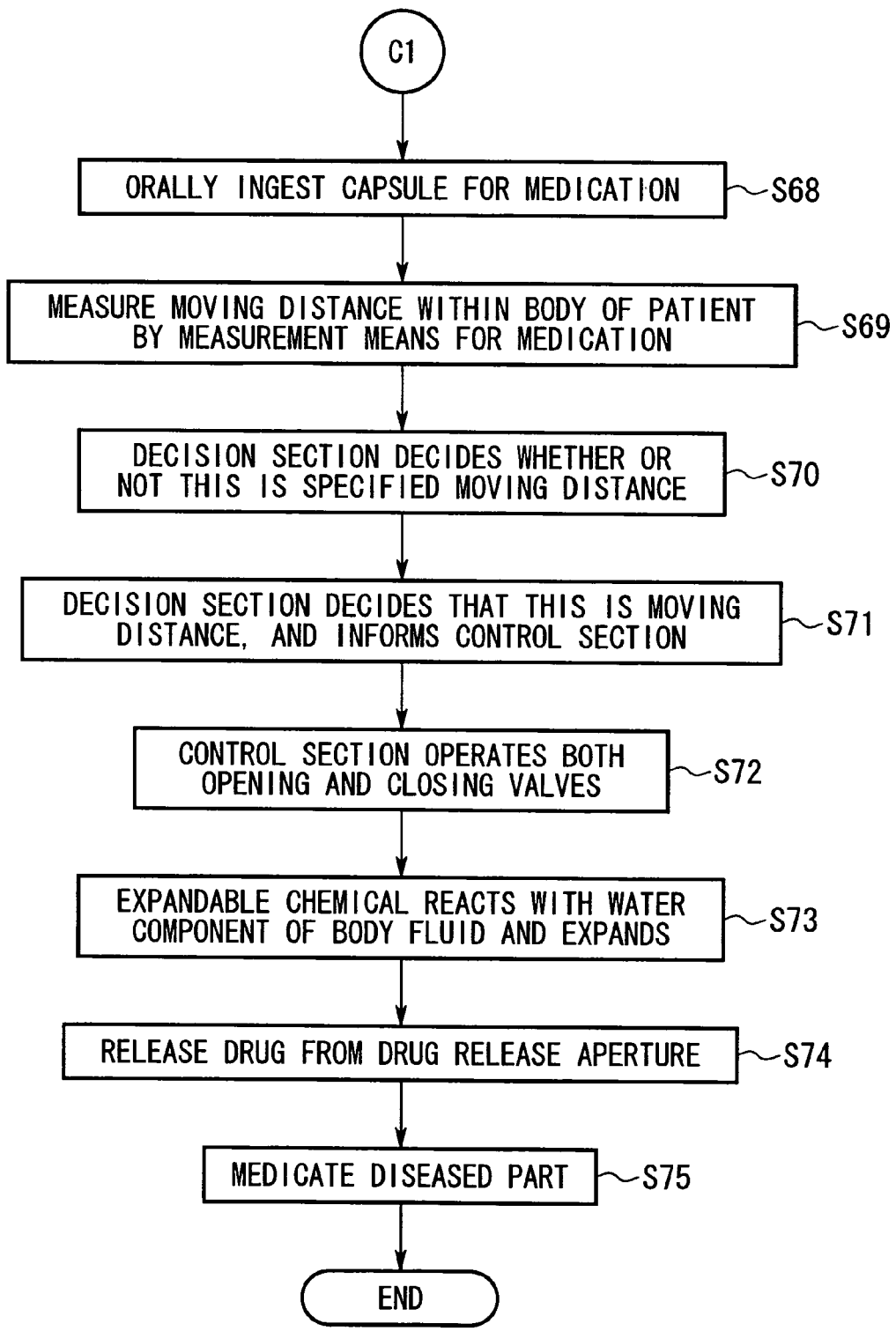
FIG. 40 is a flow chart which continues on from the flow chart of FIG. 39.

The case of performing medication with a drug A for a diseased part X inside the living body P with a capsule medication administration system of the above described structure will now be explained with reference to FIG. 38 through FIG. 40.

First, the patient P receives the capsule for observation 530 in a medical facility such as a hospital or the like, and orally ingests this capsule for observation 530 (S61). At this time, a switch which is not shown in the figures in this capsule for observation 530 is turned on when it is ingested, and electrical power is supplied to the various structural components from the battery 31. The capsule for observation 530 which has thus been orally ingested, while shifting within the living body P, causes the observation device 532 to operate so as to acquire in-vivo information by forming images of various internal portions of the living body, for example at the rate of twice in each second (S62).

Furthermore, the control section 545 causes the measurement device for observation 533 to operate, and to measure the moving distance from the point of oral ingestion. In other words, as shown in FIG. 36, the control section 545 sends a signal to the LEDs 542, and causes them to emit light L. This light L which has been emitted is reflected by the reflective mirrors 544a and 544b, and is emitted at a slanting angle against the surface of the alimentary canal lumen wall W. The light L which has been reflected back by the surface of the alimentary canal lumen wall W is incident upon the optical sensor 543. This optical sensor 543 captures the light L which has been incident, in other words of surface images of the alimentary canal lumen wall W. The image processing section 541, along with performing photography of these surface images at a high speed of, for example, 1500 to 6000 times in each second, also performs predetermined processing such as analysis of the images and the like, and performs comparison together of the various images over time by taking notice of characteristic features from among the surface images such as, for example, concave and convex shapes and the like of the tissue (in the small intestine, villus tissue). The image processing section 541, along with calculating the shift direction and the moving distance according to the variation along with the passage of time of these images, also informs the control section 545 thereof. Thus, the measurement device for observation 533 performs measures the moving distance within the living body based upon the variation along with the passage of time of the surface images of the alimentary canal lumen wall W (S63).

The control section 13 records the moving distances which are sent from the image processing section 541 and the in-vivo information which is acquired by the observation device 532 in sequence with a correspondence being established between them. (S64). Then the specification section 535, detects only the red color from among the photographic images, which are in-vivo information, which have been recorded in the memory 534, and compares this detected amount with a threshold value which has been set in advance. If the detected amount is greater than or equal to the threshold value, then it specifies that this is a hemorrhagic site (a diseased part X) for which medication is required (S65). Furthermore, after having specified the diseased part X, the specification section 535 also, as shown in FIG. 38, specifies the moving distance from the mouth of the patient P to the position of the diseased part X, from the in-vivo information which indicates the diseased part X and the moving distances with a correspondence being established with the in-vivo information recorded in the memory 534 (S66).

Next, the capsule for observation 530 which has been excreted from the patient P is retrieved, and the moving distances which have been specified by the specification section 535 are extracted and stored in the memory 557 of the capsule for medication 550 (S67). After this, the patient P orally ingests the capsule for medication 550 according to a medication time schedule which has been determined (S68). It should be understood that, for the capsule for medication 550 just as for the capsule for observation 530, a switch which is not shown in the drawings is turned on when it is ingested, and thereby electrical power is supplied from a battery 558 to its various structural components. Furthermore, after the patient P has received the capsule for medication from the physician or the like, he may leave the medical facility or the like.

On the other hand, the capsule for medication 550 which has been orally ingested performs shifting within the living body while performing measurement of its moving distance with the measurement device for medication 554 (S69). At this time, the image processing section 541 sends the moving distances which have been measured to the decision section 555. Then the decision section 555 decides whether or not the moving distance which is sent from the image processing section 541 is the specified moving distance which is stored in the memory 557 (S70). If the distance which has been sent from the measurement device for medication 554 agrees with the specified distance, then the decision section 555, along with deciding that the capsule has arrived at the position of the diseased part X, also notifies the control section 556 to this effect (S71).

The control section 556, upon receipt of this notification, causes the opening and closing valves 561 and 562 to operate, and puts the body fluid intake conduit 552*a* and the drug supply conduit 552*b* into the open state (S72). Then the body fluid F enters into the reservoir 552 via the body fluid intake aperture 559 and the body fluid intake conduit 552*a*, and starts to soak into the expandable chemical B.

Due to this, the expandable chemical B starts reacting with the water component of the body fluid F and starts to expand (S73). When the expandable chemical B expands, due to the pressure thereof, the drug A is released to the exterior of the casing 551 by pushing its way out from the reservoir 552 via the drug supply conduit 552*b* and the drug release aperture 560 (S74).

Therefore, since the release of the drug A is performed at the specified moving distance which indicates the position of the diseased part X, accordingly it is possible to perform the medication directly to the diseased part X.

According to the capsule medication administration system described above, by orally ingesting the capsule for observation 530, along with acquisition of the in-vivo information being performed by the observation device 532 while the measurement of the moving distance within the living body is being performed by the measurement device for observation 533, also specification of the moving distance to the diseased part X for which medication is required is performed by the diagnostic section 15. Thus, by orally ingesting the capsule for medication 550, it is possible for the decision section 555 to decide whether or not the moving distance which has been measured by the measurement device for medication 554 is the moving distance which is specified by the specification section 535, and for the drug A to be released at this position. Thus, in more detail, since the release of the drug A is performed at the specified moving distance which indicates the position of the diseased part X, accordingly it is possible to administer the medication to the diseased part in an accurate manner. In particular, since the medication is not performed upon detection of the diseased part X, but based upon the moving distance, accordingly it is possible to administer the drug A in an appropriate manner, without passing over the diseased part X.

Furthermore, since the medication is performed by the capsule for medication 550 itself deciding whether or not it is at the moving distance which has been specified, accordingly there is no requirement for any separate external device or the like for making this decision. Therefore, since there is no loss of time due to communication or the like with an external device or the like, and thus it is possible to manage with only a short time period from measurement of the moving distance to release of the drug A, accordingly it is possible to administer the drug A to the diseased part X with high accuracy.

Furthermore, the capsule for observation 530 and the capsule for medication 550 are able to measure the moving distance within the living body easily and moreover reliably, based upon the variation along with the passage of time of the surface information of the alimentary canal lumen wall W, with the respective measurement device for observation 533 and measurement device for medication 554, and accordingly it is possible to enhance the accuracy of the application of the medication to the diseased part X.

Figure 41:
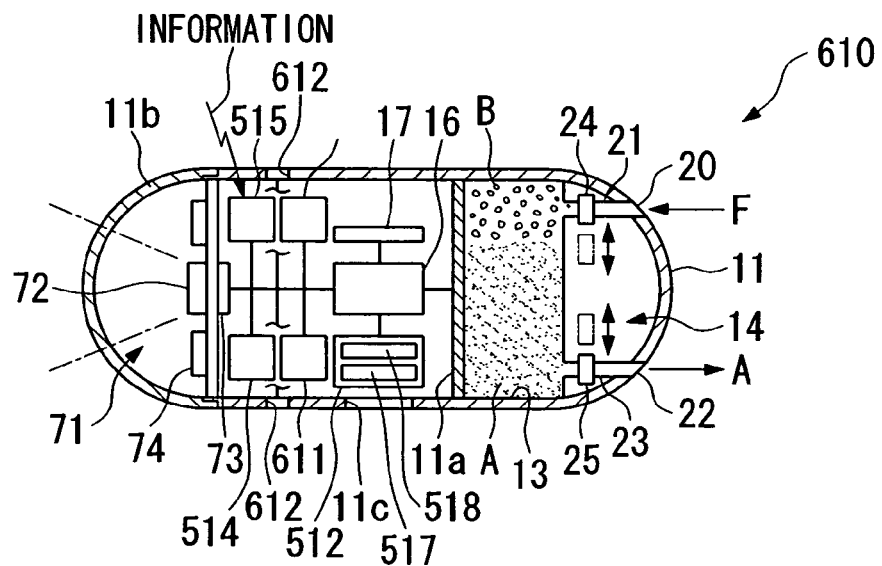
FIG. 41 is a sectional view showing a capsule for medication which is used in a seventh embodiment of the capsule medication administration system according to the present invention.

Next, the seventh embodiment of the capsule medication administration system according to the present invention will be explained with reference to FIG. 41 and FIG. 42. It should be understood that, to structural elements which are the same as those in the various embodiments described above, the same reference symbols are appended, and the explanation thereof is curtailed.

With the capsule for medication (the capsule type medical device) 610 of this embodiment, an in-capsule decision system 611 decides based upon the hardness within the living body. As shown in FIG. 41, the capsule for medication 610 includes, inside its casing 11, a hardness sensor (a sensor) 612 which measures the hardness of the living body which it has come into contact with while shifting within the living body. This hardness sensor 612, for example, may be a vibration type contact sensor, and may be provided in plurality upon the outer surface of the casing 11 around the axis of the casing 11, and, as shown in FIG. 21, along with measuring the hardness of the alimentary canal lumen wall, also sends the value which it has measured to the in-capsule decision section 611.

Figure 42:
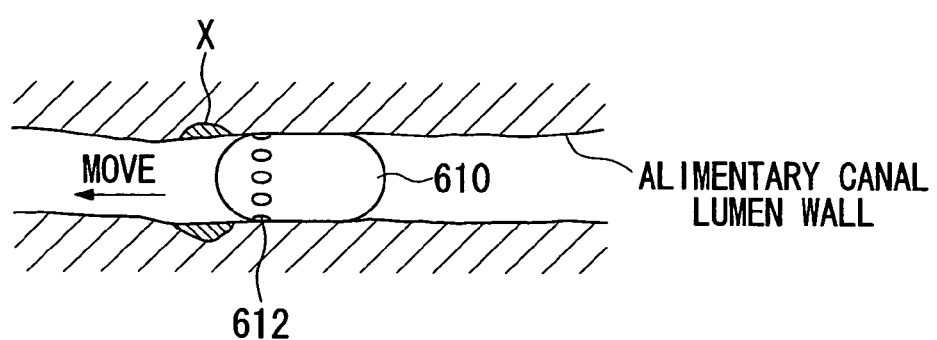
FIG. 42 is a view showing a situation in which the capsule for medication shown in FIG. 41 shifts within the alimentary canal of the patient.

As shown in FIG. 42, when the capsule for medication having this type of structure is orally ingested, the hardness sensor 612 shifts within the living body while measuring the hardness of the alimentary canal lumen. Furthermore, the in-capsule decision section 611 generates, by a data conversion process, the data for comparing together the information about the shift amount of the capsule for medication 610 itself which has been sent from the shift amount detection section 132, and the image information which has been photographed by the image formation device 71, and executes the comparison.

Therefore, the capsule for medication 610 decides whether or not it is near the diseased part X. Additionally, in this embodiment, it is possible to obtain the hardness information for the alimentary canal lumen wall. Generally, with cancerous tissue, there is a tendency for it to be harder as compared with normal tissue, so that, by detecting the hardness of a subject site, it is possible to obtain information about whether medication for a diseased part X is required or not. Whether medication is required or not is decided in an overall manner by taking all this information into account.

In this embodiment, in addition to the benefits of the various other embodiments described above, since it is possible to obtain hardness information about the tissues in the living body, accordingly it is possible to decide whether or not medication is required, not only at identified locations for the medication, but also at locations where it has not yet been decided whether the medication is required or not, so that it is possible to implement the administration of the medication effectively at higher efficiency.

Next, the eighth embodiment of the capsule medication administration system according to the present invention will be explained with reference to FIG. 43 through FIG. 47. It should be understood that, to structural elements which are the same as those in the various embodiments described above, the same reference symbols are appended, and the explanation thereof is curtailed.

The capsule medication administration system 701 of this embodiment detects a marker M due to a clip C which has been made by the specification device 231, from among the images of an image formation device 71 which is provided to the capsule for medication 710, and decides whether or not it has arrived at the medication position.

Figure 43:
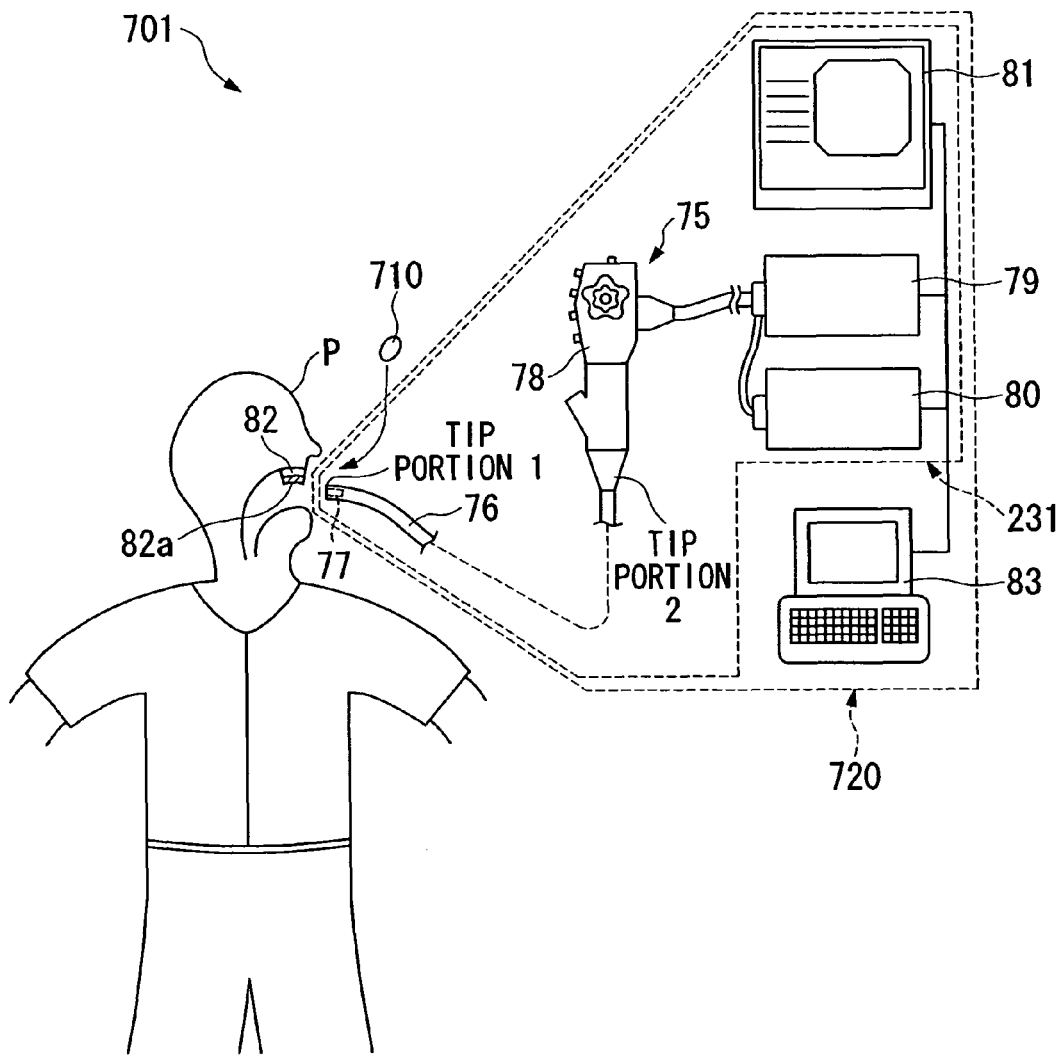
FIG. 43 is a sectional view showing a capsule for medication which is used in an eighth embodiment of the capsule medication administration system according to the present invention.

As shown in FIG. 43, the capsule medication administration system 701 includes a capsule for medication (a capsule type medical device) 710 and a unit 720 external to the living body which includes the specification device 231.

Figure 44:
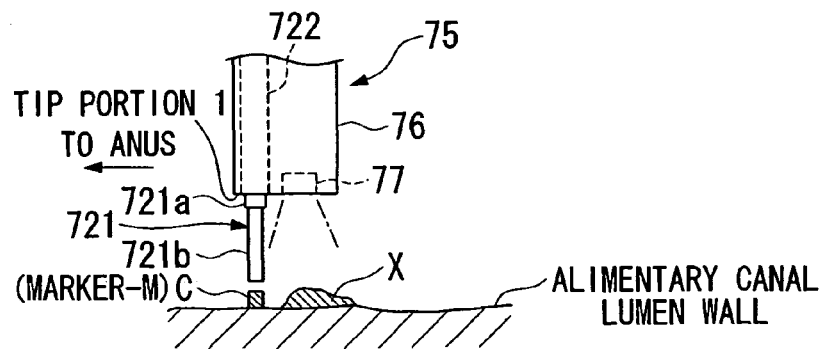
FIG. 44 is a figure showing a tip end of an insertion section 102 shown in FIG. 43, and is a view showing a situation in which a clip is made within the alimentary canal lumen wall of the patient by a marking device.

As shown in FIG. 44, the endoscope device which is employed as the specification device 231 is provided with a clipping device (a marking device) 151 which attaches a clip C which is made from metal to the vicinity of the diseased part X which has been specified. The clip C is utilized as marker M.

An insertion section 76 which is inserted within the coelom of the patient is provided to the endoscope device main body 75, and this has an opening portion at its one tip portion (its tip portion 1) which is inserted within the coelom, while, via its other opposite tip portion (its tip portion 2), there is passed an endoscopic treatment tool, which in this embodiment is taken as being a clipping device 721 which is being used for the first time; and a forceps channel 722 is provided at the one tip portion (the tip portion 1), so as to make it possible to perform endoscopic procedures.

This clipping device 721 includes an insertion section 721*a* which is inserted into the forceps channel 722, a clip retention portion 721*b* which retains a clip C, and a clip release mechanism not shown in the figures which bites into the tissue of the living body, and which releases the clip C from the clip retention portion 721*b*.

Figure 45:
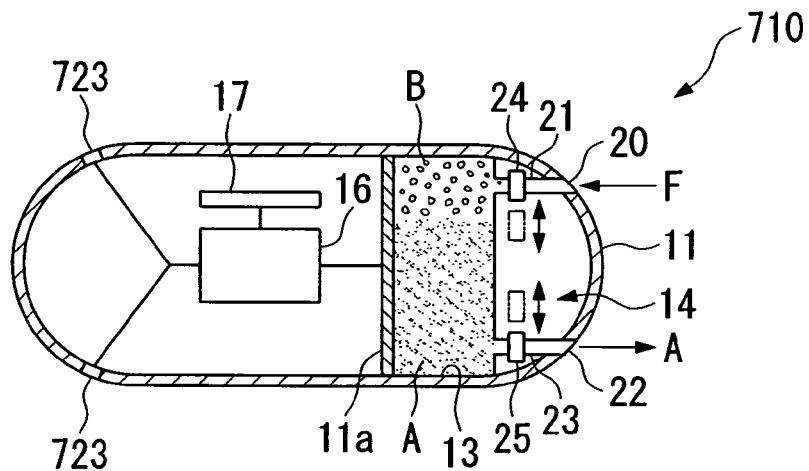
FIG. 45 is a sectional view showing a capsule for medication which is used in the capsule medication administration system shown in FIG. 43.

Furthermore, as shown in FIG. 45, the capsule for medication 710 includes, within its casing 11, a metal sensor 723 (a marking detection device or marker detection section) which detects the clip C. The metal sensor 723 is provided in a plurality upon the outer surface of the casing 11, around the axis of the outside of the casing. Furthermore, when this metal sensor 723 detects the marker M, it sends the information to the control section 16.

The case of administering medication with a drug A to a diseased part within the living body P with the capsule medication administration system 701 having the above described structure will now be explained.

After a physician or the like has performed the specification of the diseased part X for which medication is required with the specification device 231, the clipping device 721 is inserted into the forceps channel 722, and the clip C is attached at the position of the diseased part X, or, to be more exact, in its vicinity. It should be understood that this clip C is not directly attached to the diseased part X; rather, as shown in FIG. 44, it is better for it to be attached upon the side of the diseased part X towards the anus of the patient.

After this, when the capsule for medication 710 which has been orally ingested to within the living body arrives at the position of the diseased part X while shifting within the living body, the metal sensor 723 detects the clip C, and informs the control section 16 to this effect. The control section 16, upon receipt of this information, causes both of the opening and closing valves 24 and 25 to operate, thus performing release of the drug A.

Therefore, since it is possible to release the drug A at the position of the diseased part X which has been specified by the endoscope device which is being utilized as the specification device 231, accordingly it is possible to administer the medication directly to the diseased part X. Furthermore, since the detection of the position of the diseased part X is performed merely by providing the metal sensor 723, accordingly it is possible to make the structure of the capsule for medication 710 very simple. Because of this, it is possible to anticipate an enhancement in compactness. In particular, it is possible for the position of the diseased part X which has been accurately specified by the endoscope device to be easily reflected in the operation of medication by the capsule for medication 710.

It should be understood that although, in this embodiment, the clip C is employed as the marker M, this is not to be considered as being limitative; it would also be acceptable to utilize a stent which is made from metal which opened up so as to exert pressure from the interior of the alimentary canal. Furthermore, although the metal sensor 723 is employed as the marker detection section, this is not to be considered as being limitative; it would also be acceptable for it to be an image sensor which detects the metallic reflections from the clip C with images. Yet further, as the marker M, instead of the above described stent, it would also be possible to inject, for example, an isotope or a fluorescent material or a magnetic liquid or the like near the diseased part X, or to perform scattering of colored elements or the like. In these cases, for the marker detection section, it would be proper to utilize a radiation sensor which detects radiation, an image sensor which detects fluorescence in the image, a magnetic sensor which detects the magnetic liquid, an image sensor which detects the color or the brightness of a dye in the image, or the like.

Figure 46:
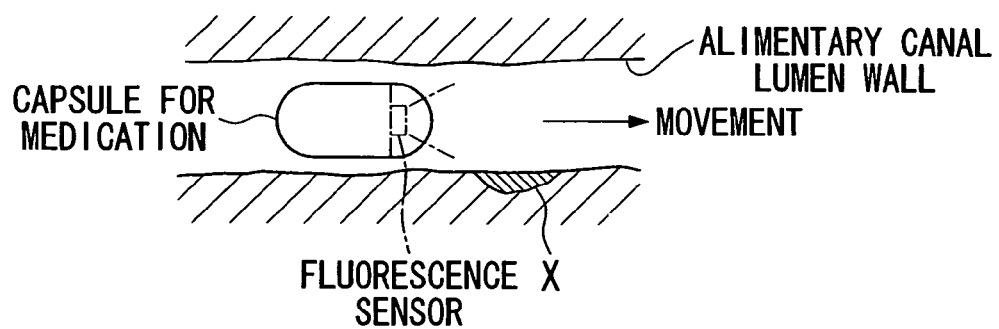
FIG. 46 is a figure showing a situation in which a capsule for medication which includes another marker detection section (a fluorescence sensor) is shifting within the alimentary canal of the patient.

Moreover although, in the above described embodiment, an endoscope device is employed as the specification device 231, this is not to be considered as being limitative; it would be acceptable to inject, from outside the living body, a fluorescent drug which has the property of accumulating in the diseased part X, and, as shown in FIG. 46, to detect the fluorescent drug with a fluorescence sensor or the like which is provided within the capsule for medication, and to administer the medication when it has been detected. In particular, this is a desirable procedure if the diseased part X is a carcinoma or the like.

Figure 47:
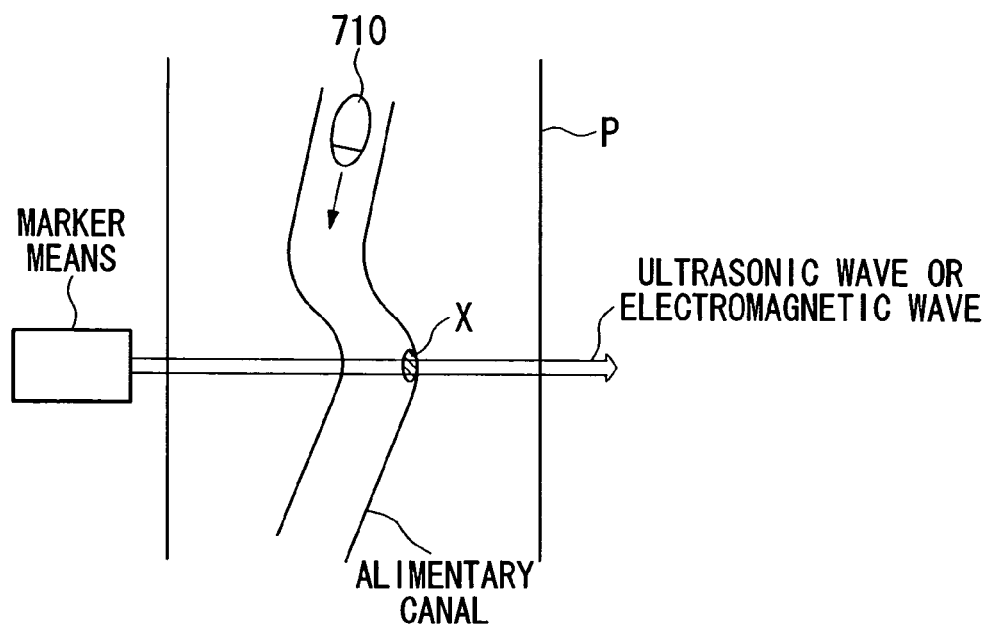
FIG. 47 is a figure showing an example of another marking device, and is a figure showing a situation in which an ultrasonic wave or an electromagnetic wave such as an infrared laser light beam or the like is being emitted from externally towards a diseased part within the living body.

Moreover, as the marking device, as shown in FIG. 47, it would also be acceptable to utilize an emission device which emits ultrasonic waves, or one such as an infrared laser or the like which emits electromagnetic waves, equipped with directivity from outside the living body towards the interior of the living body, and which can pass through the living body. In this case, it would be proper to make the marker detection section of the capsule for medication 710 so that it detects the ultrasonic waves or the electromagnetic waves. Since the above described ultrasonic waves or electromagnetic waves are equipped with directivity, it is possible to specify the position of the diseased part X accurately, and it is possible to apply the medication to the diseased part X in a reliable manner.

Next, a variant example of this embodiment will now be explained with reference to FIG. 48 and FIG. 49.

With the capsule medication administration system of this variant example, the endoscope device (the medical device) 730 specifies the diseased part X, and makes a specified marking M which indicates the position of the diseased part X. The medication is administered when this specified marking M has been detected. It should be understood that, in this variant example, the specified marking M is one which has the properties of a magnetic substance. For this marking M, apart from the possibility of it including a chemical which is a magnetic substance, it is also possible to utilize a clip or the like which is used in a procedure which is performed with an endoscope.

Figure 48:
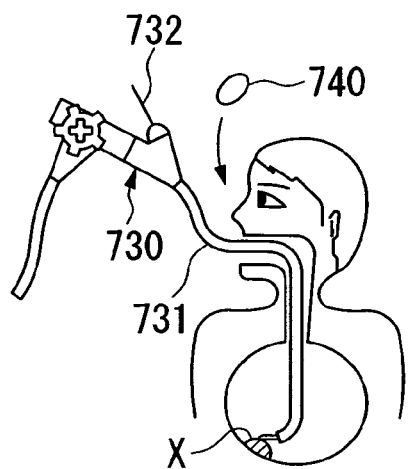
FIG. 48 is a schematic figure showing an variant example of the eighth embodiment of the capsule medication administration system according to the present invention.

As shown in FIG. 48, the capsule type medical device system of this embodiment includes an endoscope device 730 and a capsule for medication 70 which is orally ingested.

The endoscope device 730 includes an endoscope insertion section 731 which is equipped with flexibility and which can be inserted to within the living body.

This endoscope insertion section 731 includes, at its tip end, an observation device (an in-vivo information acquisition device) which is not shown in the figures, and which observes the interior of the living body. Furthermore, a treatment tool channel which is not shown in the figures is formed within this endoscope insertion section 731, and this channel is shaped so as to pass along a treatment tool insertion hole not shown in the figures which is disposed at the base end from the opening aperture in the tip end. It is possible to insert a treatment tool (a marking device) 732 which makes the marking M of the above described magnetic substance into this treatment tool channel.

Figure 49:
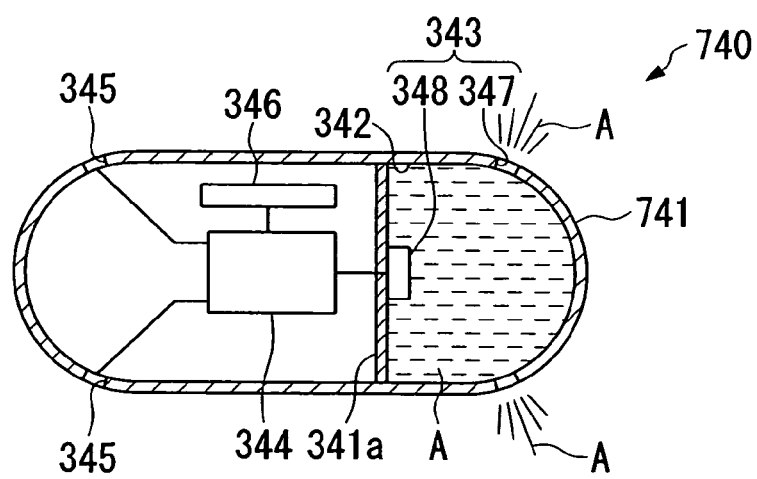
FIG. 49 is a sectional view showing a capsule for medication according to the present invention which is used in the capsule medication administration system shown in FIG. 48.

Furthermore, as shown in FIG. 49, the capsule for medication 70 includes, within its casing 341, a reservoir 342, a release device 343, a control section 344, a battery 345, and a magnetic sensor 345 (a detection device) which detects the specified marking M. Yet further, the control section 344 causes the release device 343 to operate when it detects the specified marking M.

The case of administering medication with a drug A to a diseased part X within the living body P with the capsule medication administration system of this variant example will now be explained in the following.

First, the patient P undergoes an endoscope examination at a medical facility such as a hospital or the like, and receives a diagnosis as to whether or not any thing is abnormal within his body. In other words, the endoscope insertion section 731 of the endoscope device 730 is inserted into the living body, and the inside of his body is observed with the observation system. If any diseased part X, such as a superficial disorder of the digestive organs or the like, is discovered by this endoscope examination, then the physician inserts the treatment tool 732 into the treatment tool channel, and makes a specified marking M which includes a magnetic substance within the digestive organs, in order to indicate the position of this diseased part X. After this endoscope examination, the patient P receives the capsule for medication from the physician. It should be understood that, after having received the capsule for medication 70, the patient may leave the medical facility or the like.

Next, the patient P swallows and orally ingests the capsule for medication 70. The capsule for medication 70 which has thus been orally ingested shifts while observing the digestive organs of the patient with the magnetic sensor 345. Thus, when it arrives at the specified marking M, the magnetic sensor 345 reacts to the specified marking M, which is a magnetic substance, and detects its position. When it detects the specified marking M, the magnetic sensor 345 sends a message to the control section 344 to that effect. Upon receipt of the signal from the magnetic sensor 345, the control section 344 causes the heater 348 to operate. Upon receipt of a signal from the control section 344, the heater 348 causes gas bubbles to be generated by momentarily applying heat, and the thin membrane over the drug aperture 347 is broken by the pressure of these bubbles. Due to this, the drug A within the reservoir 342 is released to the exterior of the casing 341 through the drug aperture 347. Accordingly, it is possible to administer the medication directly to the diseased part X. Furthermore, since the release of the drug A is performed at the same time as the detection of the specified marking M while shifting within the living body, therefore it is not necessary to allow any reaching time period from the detection until the release. Accordingly, it is possible to administer the medication to the diseased part with high accuracy, since the release of the drug is performed more near the specified marking A.

Figure 50A:
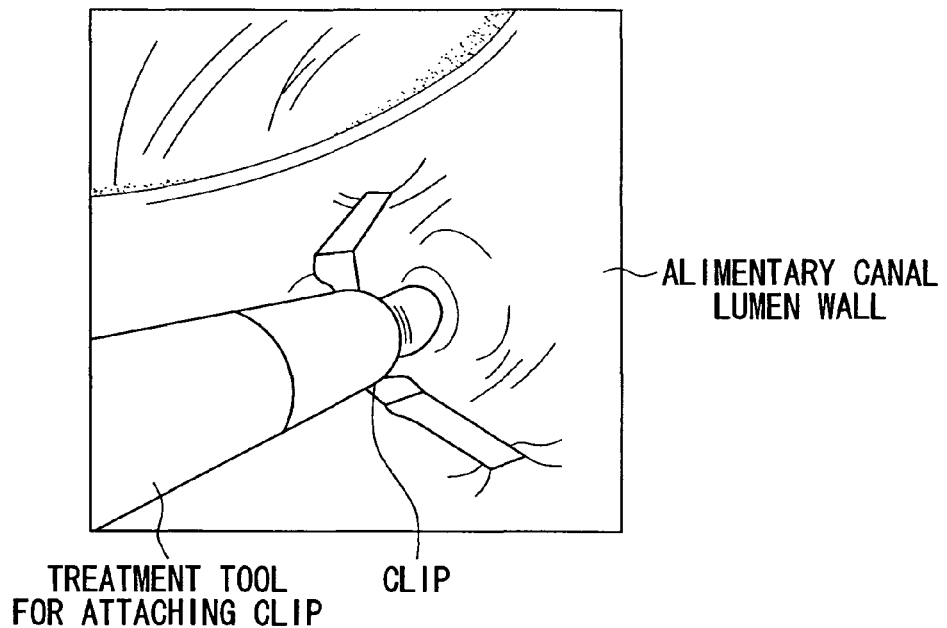
FIG. 50A and FIG. 50B are figures showing states in which a clip for endoscopy is made within the coelom of the patient by using a treatment tool which is used by the capsule type medical device shown in FIG. 48.
Figure 50B:
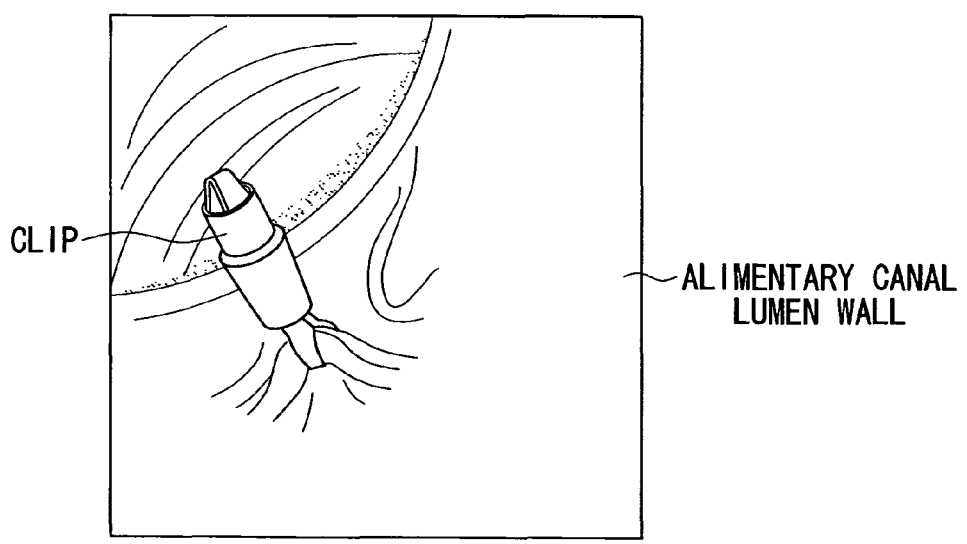

Yet further, although in this embodiment a magnetic sensor 345 is used, if the above described clip is utilized, as shown in FIG. 50A and FIG. 50B, it would also be acceptable to employ, as the treatment tool 732, a treatment tool for putting on the clip, which could put on the clip for the endoscope within the coelom. Even further, it would also be acceptable to provide a light emitting element and a light reception element to the capsule for medication 70, and to detect variation of the reflectivity ration of the light which has been emitted by the light emitting element. (Since the clip is made from metal, the amount of reflected light is increased when the clip is present.) Moreover, the light reception element might be an image sensor such as a CMOS image sensor or a CCD or the like. In this case, it would be acceptable to detect the clip by using an image processing technique.

It should be understood that the technical field of the present invention is not limited to the above described embodiments; it is possible to add various alterations, within the range in which the gist of the present invention is not departed from.

For example although, in the above described embodiments, the control section decided whether or not it is the specified marking by counting the number of the markings which are sent from the sensor, this is not to be considered as being limitative. For example, it would also be acceptable, when making the markings within the living body, to make the markings of different shapes, sizes, colors or the like, and to decide upon the specified marking by differences in its shape, size, color, or the like.

Furthermore, although the specified marking is taken as being an indicator which showed the position of the diseased part, this is not to be considered as being limitative; for example, it would also be possible to use a site within the living body which has a distinctive feature such as a shape or color or the like as an indicator.

Yet further, although in the above described embodiments the drug is released by taking advantage of a heater, this is not to be considered as being limitative; provided that the construction is one which makes it possible to control the release device by the control section, that would also be acceptable. For example, it would be acceptable to cause the drug to be released by taking advantage of a piezo element as the discharge mechanism for the capsule type medical device. Furthermore, it would also be acceptable to arrange to take osmotic pressure as the drive force to cause the drug to be released, or to arrange to cause the drug to be released by taking advantage of the swelling pressure which is generated when a hydrophilic macromolecule or the like absorbs water and swells.

Even further, although the specified marking is taken as being one in number, this is not to be considered as being limitative; if there are diseased parts at a plurality of locations, it would be acceptable to detect specified markings which indicated the positions of each of the diseased parts, so as to administer the medication. Moreover, it would also be acceptable to set up the system so as to make markings before and after the diseased part, thus sandwiching it, and to start administration of the medication at the initial specified marking, while stopping the administration of the medication at the next marking. Therefore, it is possible to administer the drug with good efficiency to the diseased part, and this is particularly effective if a plurality of diseased parts are present.

Moreover, it would also be acceptable to provide a plurality of reservoirs in the capsule for medication, and to store various different types of drug in these various reservoirs, thus performing the administration of these medications according to the nature of each diseased part.

Yet further, although, in the second embodiment, the capsule for medication detected the specified marking, which is a magnetic substance, by taking advantage of a magnetic sensor, this is not to be considered as being limitative; it would also be acceptable to make the specified marking, as specified by the endoscope examination or the like, with a shape or a color or the like, and to arrange for a construction which is able to detect that specified marking.

Still further, although, in the above described embodiments, the photographic images which are formed of the various internal organs within the living body are taken as being the in-vivo information, this is not to be considered as being limitative; it would also be acceptable to utilize pH value, or pressure, or body fluid, or the like. In this case, instead of the image formation section, it would be proper to arrange for a construction such that it is capable of acquiring these types of in-vivo information.

Still furthermore although, for the image formation section, a type is applied which took photographs within the living body intermittently at fixed intervals and moreover at random, this is not to be considered as being limitative; for example, it would also be acceptable to utilize one which took photographs of the interior of the living body continuously, such as by video or the like. In this case, the video signal would be stored.

Even furthermore, there is no limitation to a device which takes photographs of the interior of the living body with video or the like; provided that the device is one which is capable of detecting information about the interior of the living body, and of transmitting the resulting data to a device external to the living body, that will also be acceptable. For example, it would also be possible to apply a capsule for hemorrhage check which included a hemoglobin sensor, or a capsule for checking information about the interior of the living body which acquired in-vivo information intermittently over a long time period such as pH value, pressure value, temperature, microbe amount, enzyme and genetic abnormality, or the like, or an ultrasonic wave capsule which acquired ultrasonic wave images or the like intermittently.

Next, yet another variant example of this embodiment will be explained with reference to FIG. 51 and FIG. 52. With the capsule medication administration system of this variant example, the moving distance of the capsule for observation 830 is measured by a unit 820 which is external to the living body. In other words, as shown in FIG. 51, the capsule medication administration system includes the capsule for observation 830, the capsule for medication 810 which are orally ingested, and the unit 820 external to the living body, which is disposed outside the living body.

Figure 52:
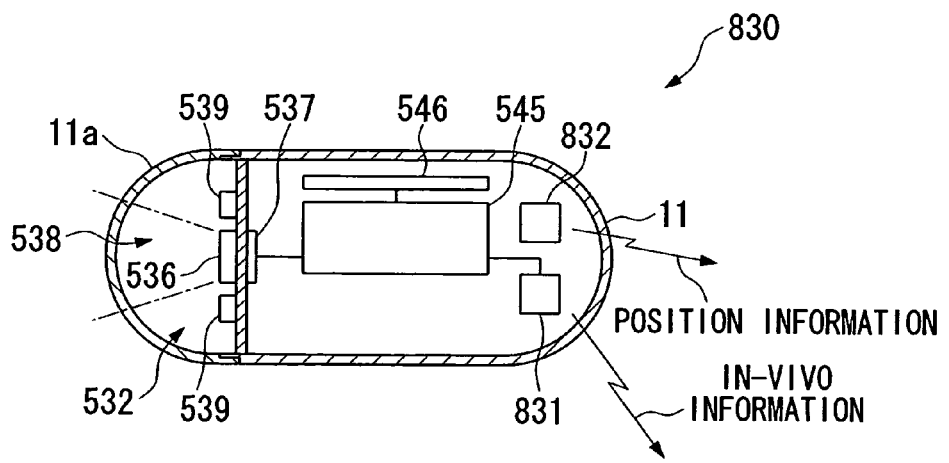
FIG. 52 is a sectional view showing a capsule for observation which is used in the capsule medication administration system shown in FIG. 51.

As shown in FIG. 52, the capsule for observation 830 includes, within its casing 11, a transmission antenna (a transmission device) 831 which transmits in-vivo information, which is photographic images which have been acquired by the observation device 12, towards the unit 820 external to the living body, and a magnet (a position transmission device) 832 which transmits information about its own position to the exterior of the living body. In other words, the control section 545 performs predetermined processing upon the in-vivo information which it has acquired from the observation device 532, and transmits from the transmission antenna 831. Furthermore, the magnet 832 notifies its own position to the exterior of the living body by generating (transmitting) magnetic force, in other words positional information, to the exterior of the living body.

Figure 51:
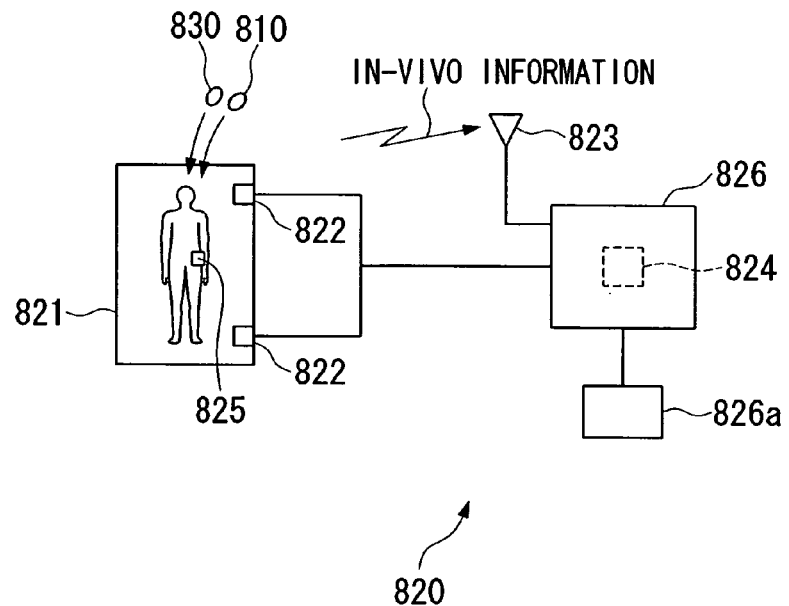
FIG. 51 is a structural view showing yet another variant example of the eighth embodiment of the capsule medication administration system according to the present invention.

As shown in FIG. 51, the unit 820 external to the living body includes: a magnetic sensor (a position detection device) 822 which is attached to an examination couch such as a bed or the like upon which the patient lies, and which detects the magnetic force which is generated by the magnet 832; a reception antenna 823 (a reception device) which receives the in-vivo information which has been transmitted from the transmission antenna 831 of the capsule for observation 830; and a specification section 824 (a specification device) which specifies a diseased part X for which medication is required, and the moving distance to this diseased part X, based upon the in-vivo information which has been received by the reception antenna 823 and the magnetic force, which is the positional information, which has been detected by the magnetic sensor 822.

Furthermore, the unit 820 external to the living body includes an external to body magnet 825, and a personal computer (hereinafter, a "PC") which includes a display monitor 826*a*. A magnetic sensor 822 and a reception antenna 823 are connected to the PC 826, the specification section 824 is also housed within the PC 826.

The external to body magnet 825 is fixedly provided at a site, with respect to the patient P who is upon the examination couch 821, at which the skeleton of the patient P such as, for example, his pelvic girdle or the like is close to the surface. Furthermore the magnetic sensor 822, along with being provided in plurality and detecting the magnetic forces of the magnet 832 of the capsule for observation 830 and of the external to body magnet 825, also calculates the three dimensional position of the capsule for observation from the difference between these two magnets 832 and 825, and sends the result to the specification section 824.

The reception antenna 823 is equipped with the function of sending the in-vivo information which it has received to the specification section 824. The specification section 824, along with detecting the red color only from the photographic image, which is the in-vivo information, which has been sent, also specifies the diseased part X for which medication is required by comparing together the detected amount and a threshold value. It should be understood that the specification section 824 is also equipped with the function of displaying this in-vivo information which has been sent upon the display monitor 826*a*. Furthermore, the specification section 824, after having specified the diseased part X, specifies the moving distance to the position of the diseased part X based upon the in-vivo information that indicates the diseased part X, and the position of the capsule for observation 830 which has been sent from the magnetic sensor 822.

It should be understood that, in this embodiment, it will be acceptable for a physician or the like to diagnose and to specify the diseased part X, based upon the in-vivo information which is displayed upon the display monitor 826*a*. Furthermore, the moving distance which has been specified by the specification section 824 is recorded in the memory of the capsule for medication 810.

The case of administering medication with a drug A to a diseased part X within the living body P with the capsule medication administration system of this type of structure will now be explained in the following.

First the patient P visits a medical facility such as a hospital or the like, and, based upon instructions from a physician, upon the examination couch 821, positions the external to body magnet 825 in a predetermined position. In this state, the patient P orally ingests the capsule for observation 830. In the capsule for observation 830 which has been orally ingested, the control section 30 transmits the in-vivo information which has been acquired by the observation device 12 from the transmission antenna 831 towards the unit 820 external to the living body.

This in-vivo information which has been transmitted is received by the reception antenna 823 of the unit 820 external to the living body, and is sent to the specification section 824. The specification section 824, along with detecting only the red color from this in-vivo information, which is the photographic image which has been sent, also compares the amount thereof which has been detected with a threshold value which is set in advance, and if it is greater than this threshold value, specifies that this is a diseased part X for which the medication is required.

On the other hand, the magnetic sensor 822 detects the magnetic force which is generated by the magnet 832 while the capsule for observation 830 is orally ingested and is shifting, and also the magnetic force of the external to body magnet 825 which is at a fixed position. The magnetic sensor 822 measures the position of the capsule for observation 830 three dimensionally by detecting the difference between these two magnets 832 and 825. This position information of the capsule for observation 830 which has been measured is sent to the specification section 824. The specification section 824 performs the specification of the moving distance to the diseased part X for which the medication is required from the positional information which has been sent from the magnetic sensor 822, and the in-vivo information which indicates the diseased part X which has been specified.

Next, the moving distance which has been specified by the specification section 824 is stored in the memory of the capsule for medication 810. After this input, the patient P orally ingests the capsule for medication 810. By orally ingesting this capsule for medication 810, it is possible to perform release of the drug A at the moving distance which has been specified, in other words at the position of the diseased part X, and it is possible to administer the medication accurately to the diseased part X. In particular, since the unit 820 external to the living body 820, along with performing the position detection of the capsule for observation 830, also performs the specification of the moving distance, accordingly it is possible to make the capsule for observation of a more simple structure, and moreover it is possible to anticipate an enhancement of the compactness thereof.

The technical field of the present invention is not limited to the above described embodiments; it will be acceptable to add various changes, within the range that the gist of the present invention is not departed from.

For example although, by way of example, in the above described first and second embodiments, the medical position specification device taken as being an X-ray CT device, this is not to be considered as being limitative; it is only required for it to be a device which can specify the diseased part and the position of the diseased part. For example, an ultrasonic wave diagnostic device, an endoscope device or the like would be acceptable; and, moreover, it would be acceptable to employ a nuclear medical diagnostic device such as the PET (Positron Emission Tomography) device 900 shown in FIG. 53, or the like.

The above described PET device 900 is a device with which a radioactive substance (a radio isotope, hereinafter termed an "RI") is injected into the blood stream of the patient P, and the radiation which is emitted from this RI is detected and is converted into an image.

Furthermore, since the above described RI is a substance which accumulates in a diseased part X such as a tumor or the like, detection of the diseased part X and of the position of the diseased part X is performed by detecting the position of the RI.

Figure 53:
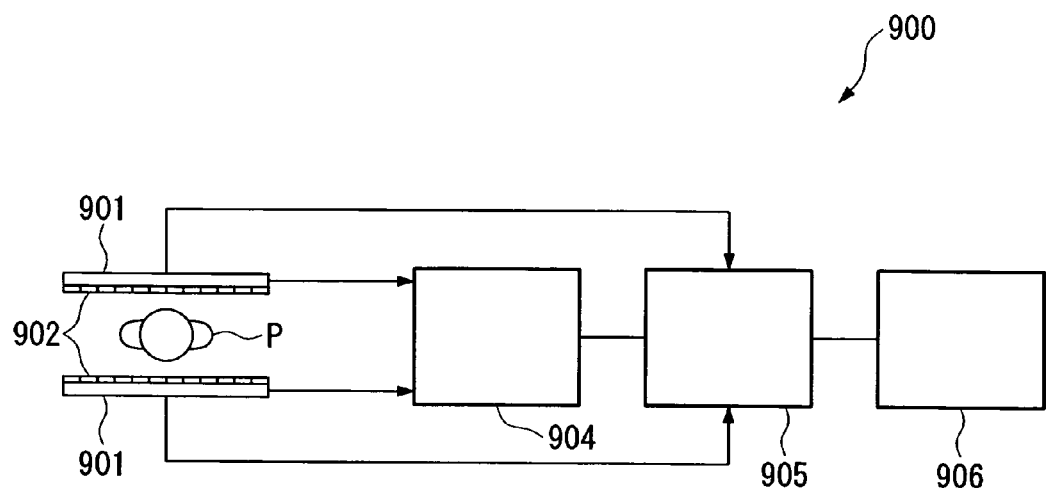
FIG. 53 is a structural view showing a PET device, which is another example of a specification device.
Figure 54:
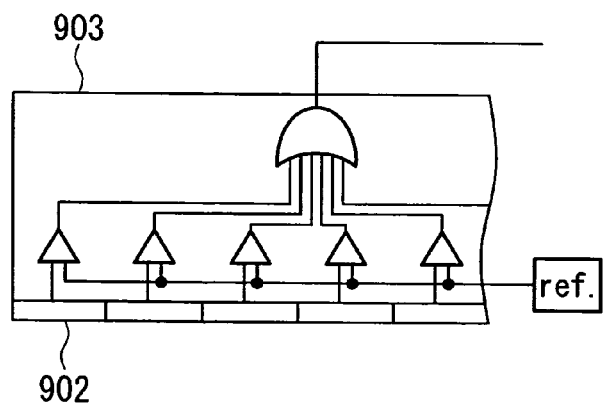
FIG. 54 is a figure showing a radiation detection circuit of the PET device shown in FIG. 53.

As shown in FIG. 53, this PET device 900 includes a pair of radiation detectors 901 which are arranged in positions which mutually oppose one another on either side of the person upon whom detection is to be performed such as a patient P or the like, and, upon their mutually confronting surfaces, each of the radiation detectors 901 includes a set of radiation detection element 902 arranged in the form of a two dimensional matrix. Furthermore, the radiation detection elements 902 are made so as to sent the radiation which they have detected via a radiation detection circuit 903 shown in FIG. 54 to a simultaneous detection circuit 904 shown in FIG. 53. For both of the radiation detectors 901, the simultaneous detection circuit 904 is made to detect the presence or absence of simultaneously incident gamma ray radiation, and, if gamma rays are incident simultaneously, along with reading out energy signals and address signals, to output them to a reconstruction device 905.

Upon receipt of the energy signals and address signals which have been sent, the above described reconstruction device 905 decides whether or not the values which indicate the energy signals which have been outputted from each of the radiation detectors 901 are near a standard value as the energy value of gamma rays, for example 511 keV, and if either of the energy signals is near the above described standard value, then it performs reconstruction of an image based upon the respective address signal. It should be understood that this image is displayed upon a monitor 906.

It should be understood that, in this PET device 900, the RI is utilized to release radiation of roughly the same intensity (about 511 keV) in directions roughly 180° apart at approximately the same time. If it has been decided that the radiation which has been released is simultaneous, the PET device 900 is built so as to take the RI as being present upon a straight line which joins the detection positions of the radiation detectors 901 upon which these two rays have respectively been incident, and so as thereby to construct its image. In other words, it decides that the RI is distributed upon the straight line which joins the positions which are indicated by the respective address signals.

Figure 55:
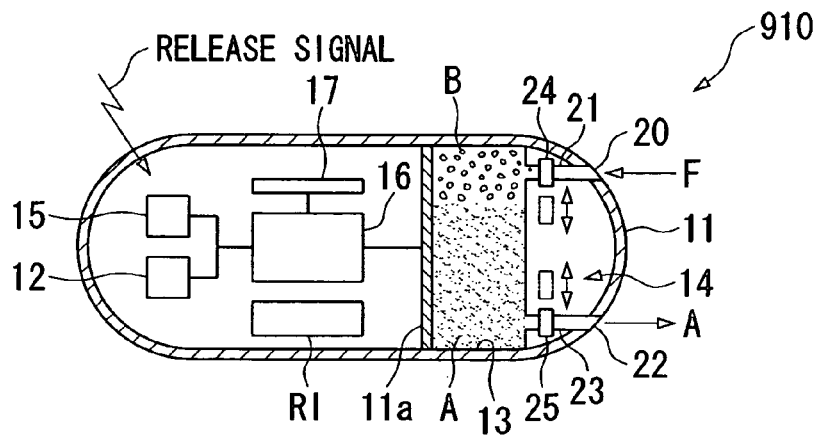
FIG. 55 is a sectional view showing a capsule for medication which is orally ingested when using the PET device shown in FIG. 53.

Furthermore, if the above described PET device 900 is employed as the specification device, the above described RI may be housed within the casing 11 of the capsule for medication 910, as shown in FIG. 55.

If this PET device 900 is taken advantage of for administering medication to a diseased part X, then, when the capsule for medication is orally ingested, the position of the diseased part X and the position of the capsule for medication 901 are displayed upon the monitor 906 in the form of a so called RI position display. The shifting of the capsule for medication 910 (for example, peristaltic movement) is checked upon the monitor 906, and, when it is superimposed over the position of the diseased part X, or when it is in a position in the vicinity thereof, then it is possible to transmit the release signal from the external device 35 and to perform the release of the drug A in the capsule for medication 910.

Figure 56:
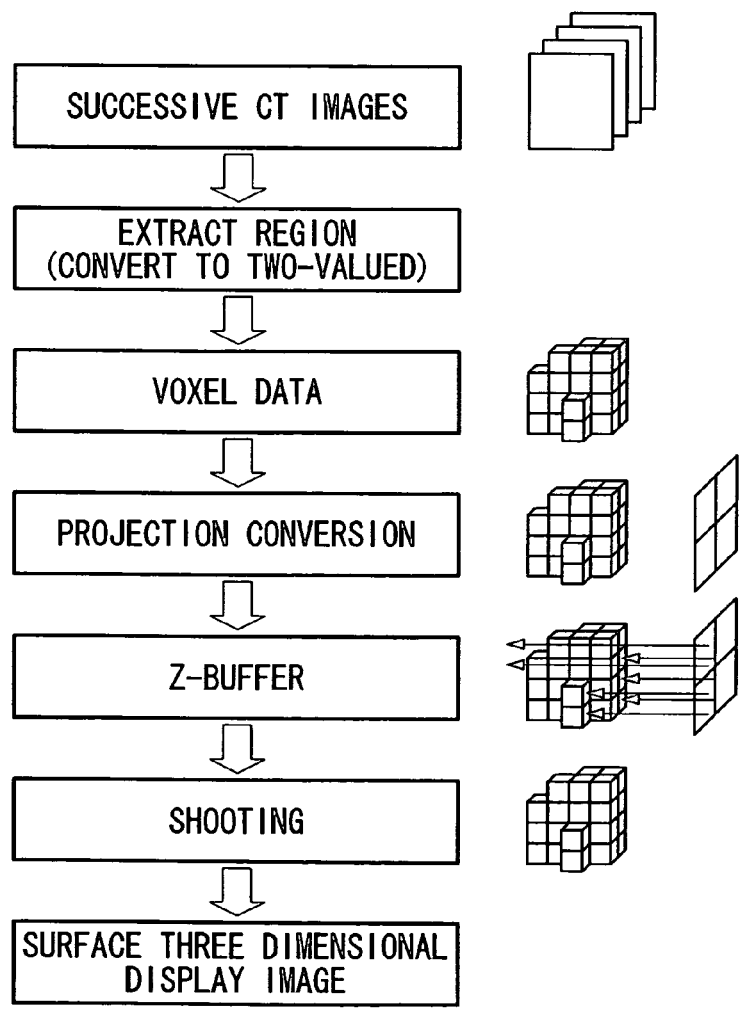
FIG. 56 is a figure showing procedures of a surface rendering method for obtaining a three dimensional image of a diseased part, when using a three dimensional CT device, which is another example of a specification device.

Moreover, it would also be acceptable to utilize a diagnostic device such as a three dimensional CT device or an MRI device or the like as the specification device. With these diagnostic devices, it is possible to construct a surface image in three dimensions by, for example, the surface rendering procedure shown in FIG. 56, in which, in detail, for successive CT images of the patient P, voxel data are created by performing binarization processing, and thereafter, along with creating a Z-buffer which shows distance from the projection surface, shading is performed while considering light reflection. It should be understood that this three dimensional image may be created internally or externally to the tissue.

After having constructed the three dimensional surface image, the physician or the like, along with specifying the diseased part X based upon the three dimensional surface image which is displayed upon a personal computer, a monitor or the like, also specifies the three dimensional position of the diseased part X. It should be understood that, if a plurality of information items are present, a plurality of positions may be obtained.

After having specified the diseased part X and the position of the diseased part X, the positional information for the diseased part X is downloaded into the memory 53 of the external device 35, and is recorded. After this, the decision section 51 of the external device 35 compares together the positional information which has been sent from the capsule for medication 910 which has been orally ingested, and the information about the position of the diseased part X which has been recorded in the memory 53, and if the capsule for medication 910 has arrived near the diseased part X, then it is able to transmit the release signal and to perform release of the drug A in the capsule for medication 910.

It should be understood that, if the positional information which is sent from the capsule for medication 910 and arrives is far separated from the positional information for the diseased part X, then the decision section 51 may transmit a command to the capsule for medication 910 to stop the release of the drug A. Furthermore, if a plurality of diseased parts X have been specified, then the above described procedure is repeated each time the capsule for medication 910 comes near the position of one of these diseased parts X.

Yet further, if the specification device is a diagnostic device which can obtain a tomographic image, such as a helical CT or an ultrasonic wave observation device or the like, this can also be applied.

Even further, although an electromagnetic wave is transmitted from the capsule for medication in order to detect the positional information of the capsule for medication, this is not to be considered as being limitative; anything will be acceptable, provided that it is information by which the unit external to the living body can detect the position of the capsule for medication. For example, it would be acceptable to provide a magnet or the like within the capsule for medication, and for the unit external to the living body to detect the position of the capsule for medication according to the strength of the magnetic attraction thereof. Furthermore, in addition to the magnet which is within the capsule for medication, it would also be acceptable to provide a fixed magnet to the patient or the like, and to detect the position of the capsule for medication by measuring the difference between the magnetic attractions which are generated by these two magnets.

Moreover it would be acceptable, in order to perform communication with the capsule for medication, for the patient to put on an antenna unit which is made up from a plurality of antennas. When doing so, the position of each of the antennas should be stuck in a location which is set in advance. Therefore, since it is possible to acquire the intensity of the electromagnetic waves which are transmitted from the capsule for medication for each of the antennas individually, accordingly it is possible for the device external to the living body to recognize the position of the capsule for medication with high accuracy. Furthermore, since the system performs communication in both directions between the capsule for medication and the device external to the living body, accordingly a system would also be acceptable in which the strength of the electromagnetic waves which have been transmitted via the antennas which are connected to the device external to the living body is detected with the capsule for medication, and the position is calculated from the difference in the strengths of these electromagnetic waves which have been detected.

Furthermore, in the second embodiment, it would be acceptable for the decision section to be made so as to detect the red color from the photographic images, and to compare it with a threshold value. Yet further, it would be acceptable, along with noting other colors than red (such as blue, green, fluorescence, infrared, or the like), to compare the detected amounts of these colors with threshold values. Even further, it would also be acceptable to extract a shape characteristic, and to made the diagnosis based thereupon.

Moreover although, in the above described third embodiment, fifth embodiment, and sixth embodiment, the specification device, in other words the endoscope device, specified the positional information for the diseased part according to the image information corresponding to the insertion distance, or the image information corresponding to the moving distance, this is not to be considered as being limitative.

Still further, it would also be acceptable to record three dimensional information for the capsule for medication in the memory, and for the capsule for medication itself to decide whether or not it has arrived at the position of the diseased part.

Furthermore although, in the above described fifth embodiment, light is emitted against the surface of the alimentary canal lumen wall by the measurement section and the surface information is captured, and the moving distance is calculated based upon the variation along with the passage of time of the surface information, this is not to be considered as being limitative; any method would serve, provided that it is able to measure the moving distance within the living body. For example, it would be acceptable for the image formation section to also serve as the measurement section. In other words, it would also be acceptable to form an image of the surface of the alimentary canal lumen wall, and to calculate the moving distance based upon the variation along with the passage of time of this surface information. In particular, it is possible to measure the moving distance with high accuracy by obtaining the central line of the alimentary canal and performing image processing thereupon. Moreover, it is possible to obtain the running line of a smooth alimentary canal by performing low pass filter processing according to requirements.

Yet further although, in the above described embodiments, the capsule for medication caused the release of the drug by taking advantage of an expandable chemical, this is not to be considered as being limitative; a system of any structure will be acceptable, provided that it is capable of releasing the drug which is being retained in the reservoir.

Even further although, in the various embodiments described above, the photographic images which are formed of the various parts within the living body are taken as being the in-vivo information, this is not to be considered as being limitative; it would also be acceptable to photograph the interior of the living body continuously, as by video or the like. In this case, the video signal would be stored.

Even furthermore, there is no limitation to a device which takes photographs of the interior of the living body with video or the like; provided that the device is one which is capable of detecting information about the interior of the living body, and of transmitting the resulting data to a device external to the living body, that will also be acceptable. For example, it would also be possible to apply a capsule for hemorrhage check which included a hemoglobin sensor, or a capsule for checking information about the interior of the living body which acquired in-vivo information intermittently over a long time period such as pH value, microbe amount, and genetic abnormality, or the like, or an ultrasonic wave capsule which acquired ultrasonic wave images or the like intermittently.

Moreover although, in the various embodiments described above, the capsule for observation and the capsule for medication each emitted light against the surface of the alimentary canal lumen wall with LEDs in order to capture surface information with an optical sensor, and the moving distance is calculated based upon variation of the surface information along with the passage of time, it is not always necessary to use LEDs or the like as structural elements; it would also be acceptable to make the observation device also serve as the measurement device for observation. In other words, it would be acceptable to form an image of the surface of the alimentary canal lumen wall with an objective lens, and to calculate the moving distance based upon the variation along with the passage of time of this surface information. Therefore, it would be possible to anticipate a further enhancement of the compactness.

Furthermore, although the measurement device for observation and the measurement device for medication are arranged to calculate the moving distance by the variation along with the passage of time of the surface information, this is not to be considered as being limitative; any construction would be acceptable, provided that it is able to measure the moving distance within the living body.

Yet further, it would also be acceptable to house an observation device within the capsule for medication, just as for the capsule for observation. In this case, since it would be possible to perform measure the moving distance and to form images within the living body at the same time, accordingly the accuracy of application of the medication to the diseased part is further enhanced. Moreover, in the same manner as described above, it would also be acceptable to make the observation device also serve the function of the measurement device for medication.

Still further, although the photographic images of the interior of the living body which are formed by the observation device are taken as being the in-vivo information, this information is not to be considered as being limited to being photographic images. For example, it would also be possible to utilize a sensor which detects pH value within the living body, or a blood sensor or the like which detects hemorrhage. In this case, it would be possible to employ blood information such as the presence or absence of hemorrhage within the living body, or the amount thereof, or a blood component or the like, as the in-vivo information. Furthermore, it would also be acceptable to combine a blood sensor and the above described observation device which serve as the acquisition device. Therefore, it would be possible to acquire more accurate in-vivo information.

Even further, although the capsule for medication utilized an expandable chemical for releasing the drug, this is not to be considered as being limitative; any structure would be acceptable, provided that it is capable of releasing the drug which is being retained in the reservoir.

Furthermore, although the specification section detected the red color from the photographic images, which are the in-vivo information, and compared it with the threshold value, this is not to be considered as being limitative; it would also be acceptable for it to take advantage of a method like a finite element method or the like, or, along with taking note of colors other than red color (such as blue, green, fluorescence, infrared, or the like), to compare the detected amounts of these colors with threshold values. Yet further, it would be acceptable to specify the diseased part, not only based upon color, but upon extraction of shape characteristics, Still further although, in the fifth embodiment and in the eighth embodiment, the diseased part for which medication is required is specified by the specification section of the unit external to the living body comparing together the in-vivo information and the threshold value, this is not to be considered as being limitative; it would also be acceptable for the diseased part to be specified by a decision of the physician. Therefore, a more detailed diagnosis would be possible, and it would be possible to specify the diseased part more certainly.

Moreover, although the moving distance which is specified is taken as only being singular, this is not to be taken as being limitative; if diseased parts are present at a plurality of locations, it would also be possible to set individual moving distances to each of these diseased parts, and to arrange to provide medication at each of these positions. Furthermore, it would also be acceptable to provide a plurality of reservoirs in the capsule for medication, to store various different types of drugs in these various reservoirs, and to perform the administration of medication in correspondence to each of the diseased parts.

Yet further although, in the eighth embodiment, the structure is such that a magnet is housed in the capsule for observation, and magnetic force is generated as the positional information, this is not to be construed as being limitative; it would also be acceptable to transmit electromagnetic waves. In this case it would also be acceptable, along with receiving these electromagnetic waves with a unit external to the living body, also to calculate the position of the capsule for observation based upon the intensity of these electromagnetic waves.

Even further, it would also be acceptable to measure the moving distance within the living body by housing an acceleration sensor within the capsule for observation and/or the capsule for medication, thus transmitting acceleration information as positional information towards the unit external to the living body by data communication, and by, along with receiving this information with the unit external to the living body, detecting the acceleration within the living body by subtracting the value of a body acceleration sensor which is provided to the living body, and then integrating the acceleration twice.

Furthermore although, in the various embodiments described above, the photographic images which are formed of the various portions within the living body are taken as the in-vivo information, this is not to be considered as being limitative; it would also be acceptable to utilize a device which took photographs of the interior of the living body continuously, such as by video or the like. In this case, the video signal would be stored.

Still further, there is no limitation to a device which takes photographs of the interior of the living body with video or the like; provided that the device is one which is capable of detecting information about the interior of the living body, and of transmitting the resulting data to a device external to the living body, that will also be acceptable. For example, it would also be possible to apply a capsule for hemorrhage check which included a hemoglobin sensor, or a capsule for checking information about the interior of the living body which acquired information about the interior of the living body, such as pH value, microbe amount, genetic abnormality, or the like intermittently over a long time period, or an ultrasonic wave capsule which acquired ultrasonic wave images or the like intermittently.

Figure 57:
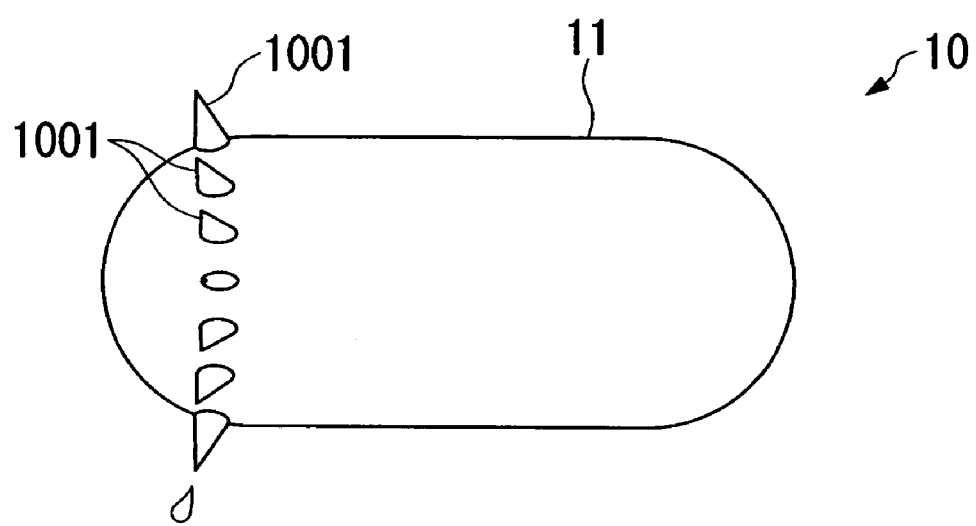
FIG. 57 is an external view showing an example in which injection needles for discharge of a marking material or of a liquid medicine have been provided to the capsule for medication.

Yet further, with the above described embodiments in which a medication device or a marking device with spots of black ink are employed, a construction would also be acceptable in which, as a method of discharging a liquid substance, a short fine injection needle (an injection device) is provided to the capsule for medication, and this needle is stuck into the alimentary canal wall, so as to administer a marking material or a liquid drug. With such a structure, after the capsule for medication has arrived at the predetermined site, as shown in FIG. 57, a plurality of minute injection needles 1001 which are embedded within the capsule 10 are projected in all directions from the outer surface of the casing 11, and stick into the mucosa of the tube wall, then discharging a marking material or a liquid medicine. This projection of the injection needles 1001 may be done by taking advantage of a piezoelectric actuator or an electrically conductive macromolecular actuator or the like. Moreover, if ultrasonic wave oscillators are provided to the injection needles 1001, and if the injection needles 1001 are projected while vibrating these oscillators, it becomes easier for these injection needles 1001 to penetrate into the mucosa. Furthermore, it would also be acceptable not to move all of the injection needles 1001 at the same time, but to arrange to move them individually, one at a time. Therefore, it would be possible to make the markings with the marking material more certainly upon the wall of the alimentary canal. Yet further, it would be possible to administer the drug to the diseased part more certainly, and it would be possible to anticipate further enhancement of the beneficial healing effects.

With the capsule medication administration system according to the present invention, the transmission and reception of signals is performed by the communication section with the external device while the capsule type medical device which has been orally ingested is shifting within the living body. On the other hand, the information acquisition section performs acquisition of various types of in-vivo information. The comparison section compares together the information which has been acquired by the information acquisition section and the conditions which have been inputted by the condition input section to the external device in order to operate the drug release section, and when, for example, the information which has been acquired and the conditions which have been inputted agree with one another, decides that the capsule type medical device has arrived at the position of the diseased part for which the medication is required. Upon receipt of this information, the external device transmits a signal to the capsule type medical device, and causes the drug release section to operate so as to release the drug.

Therefore, it is possible to release the drug at the position which has been inputted by the condition input section, so that it is possible to apply the medication directly to the diseased part which is desired.

With the capsule medication administration system according to the present invention, since the medication position specification device is connected to the condition input section, it is possible to input the data for deciding upon the site at which medication is required to an external device. Accordingly, it is possible to perform the administration of medication to the site for which medication is required at high accuracy.

With the capsule medication administration system according to the present invention, since the data which has been specified by the CT scanner can be reflected within the capsule type medical device, accordingly it is possible to perform the administration of the medication in an accurate manner.

With the capsule medication administration system according to the present invention, since the data which has been specified by an X-ray observation device can be reflected within the capsule type medical device, accordingly it is possible to perform accurate medication.

With the capsule medication administration system according to the present invention, since the data which has been specified by an MRI scanner can be reflected within the capsule type medical device, accordingly it is possible to perform accurate medication.

With the capsule medication administration system according to the present invention, since the data which has been specified by a PET scanner can be reflected within the capsule type medical device, accordingly it is possible to perform accurate medication.

Moreover, with the capsule medication administration system according to the present invention, since the data which has been specified by an ultrasonic tomographic observation device can be reflected within the capsule type medical device, accordingly it is possible to perform accurate medication.

With the capsule medication administration system according to the present invention, since the data which has been specified by an endoscope device can be reflected within the capsule type medical device, accordingly it is possible to perform accurate medication.

With the capsule medication administration system according to the present invention, since the information from the medical position specification device is abridged, accordingly, in the comparison section, the comparison is performed in the state in which the total amount of comparison calculation is kept relatively low, so that it is possible to perform this comparison of the data easily.

With the capsule medication administration system according to the present invention, since the medication is administered at the position of the marking which has been detected by the marking detection device, accordingly it is possible to administer the medication to the diseased part with high accuracy.

With the capsule medication administration system according to the present invention, since the medication is administered at the position of the diseased part for which the medication is required based upon the moving distance within the lumen, accordingly it is possible to administer the medication to the diseased part with high accuracy.

With the capsule medication administration system according to the present invention, it is possible to release the drug at the position which has been inputted by the condition input section, so that it is possible to administer the medication directly to the desired diseased part.

With the capsule for medication according to the present invention, after it has been orally ingested to within the living body, it shifts within the living body while the detection device searches for the indicator. When the detection device detects the indicator, such as a characteristic shape, color, or marking while shifting, it sends information to that effect to the release control device. The release control device, upon receipt of this output of the detection device, causes the release device to operate and thereby causes the drug within the drug retention section to be released within the living body. Thus, in more detail, release of the drug is performed at the position of the indicator which indicates the position of the diseased part. In this manner, along with being able to approach the desired site within the living body (the diseased part) easily and moreover directly, it is also possible to administer the medication. In particular, since the administration of the medicine is not performed upon detection of the diseased part, but rather the medication is administered upon detection of the indicator which indicates the position of the diseased part, accordingly it does not happen that the diseased part is passed over before the medication has been administered, and it is possible to administer the medication efficiently to the diseased part.

With the capsule type medical device according to the present invention, after it has been orally ingested to within the living body, it shifts within the living body while, along with the in-vivo information acquisition device acquiring in-vivo information, the marking device also is leaving indications within the coelom. Furthermore, the transmission device transmits in-vivo information and the indicators to the exterior of the casing. Based upon this in-vivo information and these indicators which have been transmitted, it is possible to detect the desired site within the living body easily by these indicators, and it is possible to perform a direct approach to the desired site.

With the capsule type medical device system according to the present invention, along with inserting a medical device such as, for example, an endoscope device or the like within the coelom, and performing the acquisition of the in-vivo information within the coelom with this in-vivo information acquisition device, also an indication is left with the marking device at the desired site such as a diseased part or the like. After this, the capsule type medical device which has been orally ingested shifts within the coelom while detecting, with the indicator detection device, the indicators which have been left within the coelom. When the indicator detection device detects an indicator, based upon this detected information, the control section causes the drug release section to operate, and thereby causes the release of the drug within the drug storage section.

In this manner, along with it being possible to approach the desired site easily and moreover directly, it is also possible to administer the medication. In particular, since the medication is not administered upon detection of the diseased part, but, rather, the medication is administered upon detection of the indicator which indicates the position of the diseased part, accordingly the diseased part is not passed over before having been medicated, and it is possible to administer the medication to the diseased part with good efficiency.

With the capsule type medical device system according to the present invention, by orally ingesting the second capsule type medical device, the information transmission section transmits the in-vivo information which has been acquired by the in-vivo information acquisition device and also the movement information of the marking device towards the exterior of the sheathing section. Furthermore, the reception device, along with receiving the in-vivo information and the movement information which have been transmitted, also, from this information, detects the desired site within the coelom as an indicator. After this, the position of the indicator is detected by the capsule type medical device which has been orally ingested, and the release of the drug at the indicator position is performed. Since it is possible to embody the medical device in this manner as the second capsule type medical device, accordingly it is possible to anticipate an enhancement of the compactness, and it is possible for it to be simply and conveniently orally ingested into the patient or the like.

With the CONTROL METHOD according to the present invention, for example, along with obtaining the in-vivo information by forming images of the interior of the living body with an endoscope device or the like, determination of the position for medication is performed based upon this information which has been obtained. Furthermore, after having determined the position for medication, an indicator is affixed near the medication position. Next, the capsule for medication is, for example, inserted within the coelom by being orally ingested. When the capsule for medication which has thus been inserted shifts within the coelom, detection of the indicator which has been affixed near the position for medication is performed. When the indicator has been detected, the drug release control section performs control so as to operate the drug release section. In this manner, it is possible to perform control of the operational timing of the drug release section by taking the fact that the indicator has been detected as a trigger.

With the control method according to the present invention, for example, a capsule which is separate from the capsule for medication is inserted into the living body, and, along with acquiring the in-vivo information, it shifts within the living body while leaving the indicators. Furthermore, at the same time the in-vivo information and the timing at which the indicators have been affixed are recorded in correspondence to one another. Yet further, the position for medication is determined from the in-vivo information, and, after having set the medication position into the capsule for medication, the capsule for medication is inserted within the coelom by, for example, being orally ingested. While the capsule for medication which has thus been inserted is shifting within the coelom, along with performing detection of the indicators, it performs detection of the position for medication from the indicators. When the medication position has been detected, the drug release control section performs control so as to operate the drug release section. In this manner, it is possible to perform control of the operational timing of the drug release section by taking the detection of the position for medication as a trigger.

According to the capsule for medication according to the present invention, when, during the shifting within the living body, when the detection device detects the indicator such as a shape, a color, a marking, or the like which has a special characteristic, the release control device causes the release device to operate and causes the drug within the drug retention section to be released to within the living body. Accordingly, along with it being possible to approach the desired site (the diseased part) within the living body easily and moreover directly, it is also possible to administer the medication. In particular, since the medication is not administered upon detection of the diseased part, but, rather, the medication is administered upon detection of the indicator which indicates the position of the diseased part, accordingly it never happens that the diseased part is passed over before the medication, and it is possible to administer the medication to the diseased part at high efficiency.

With the capsule medication administration system according to the present invention, when the capsule for observation is orally ingested within the living body or the like and shifts within the living body, along with acquiring the in-vivo information such as photographic images or the like with the acquisition device, also the measurement of the moving distance from when the capsule is orally ingested is performed by the measurement device for observation. At this time, the in-vivo information which has been acquired is recorded in order in the memory with a correspondence being established with the moving distance. The specification device, along with deciding that hemorrhage is occurring, based upon the in-vivo information which is recorded in the memory, when, for example, the amount of red color of the photographic images of the interior of the living body has become greater than a threshold value, and specifying that this is the diseased part for which the medication is required, also specifies the moving distance to this diseased part for which the medication is required from the in-vivo information which specifies the diseased part and the moving distance which is established in correspondence with the in-vivo information which is recorded in the memory.

After specification of the moving distance, the capsule for medication which has been orally ingested shifts within the living body while measuring the moving distance with the measurement device for medication. The decision device compares the moving distance which has been measured with the moving distance which has been specified by the specification device, and, if it decides that it is the specified moving distance, then it notifies the control device to that effect. Upon receipt of this message, the control device causes the release device to operate and releases the drug within the drug retention section.

Therefore, it is possible to release the drug at the position of the diseased part, and it is possible to administer the medication to the diseased part in an accurate manner. In particular, since the medication is not applied while detecting the diseased part, but is applied based upon the moving distance, accordingly it is possible to administer the drug appropriately (directly) without passing over the diseased part. Furthermore, since the capsule for medication itself decides whether it is the specified moving distance and performs the medication, therefore there is no requirement for any separate external device or the like for performing this decision. Therefore, since there is no loss of time due to communication with such an external device or the like, and it is possible to manage with a short period of time after the moving distance has been measured for the release of the drug, accordingly it is possible to administer the drug to the diseased part with high accuracy.

With the capsule medication administration system according to the present invention, when the capsule for observation has been orally ingested to within the living body or the like and shifts within the living body, along with acquiring the in-vivo information such as photographic images or the like with the acquisition device, it also performs measurement of the moving distance from when it is orally ingested with the measurement device for observation. At this time, the in-vivo information which has been acquired is transmitted towards the unit external to the living body by the transmission device with a correspondence being established with the moving distance.

The information which has been transmitted, along with being received by the reception device of the unit external to the living body, is also sent to the specification device. The specification device, along with deciding that this is a hemorrhagic location based upon the in-vivo information which has been sent from the reception device for example, when the amount of red color on the photographic image of the interior of the living body is greater than or equal to the threshold value and specifying it as being the diseased part for which the medication is required, also, from the in-vivo information which specifies the diseased part and the moving distance which has been established in correspondence with the in-vivo information which has been sent from the reception device, specifies the moving distance to this diseased part for which the medication is required.

After the moving distance has been specified, the capsule for medication which has been orally ingested shifts within the living body while measuring the moving distance with the measurement device for medication. At this time, the decision device compares the moving distance which has been measured and the moving distance which has been specified by the specification device, and, if it decides that it is the moving distance which has been specified, informs the control device to that effect. Upon receipt of this message, the control device causes the release device to operate and releases the drug within the drug retention section.

Therefore, it is possible to release the drug at the position of the diseased part, and it is possible to administer the medication to the diseased part certainly and moreover directly. In particular, since the unit external to the living body performs the diagnosis and the specification of the moving distance, accordingly it is possible to make the capsule for observation simple, and it is thus possible to anticipate an enhancement in compactness.

With the capsule medication administration system according to the present invention, when the capsule for observation has been orally ingested to within the living body or the like shifts within the living body, along with the in-vivo information such as photographic images or the like being acquired by the acquisition device, it is also transmitted towards the unit external to the living body by the transmission device. Furthermore, it notifies its own position with the position transmission device by transmitting positional information by magnetic force or electromagnetic waves to the exterior of the living body.

The position detection device of the unit external to the living body detects the position of the capsule for medication within the living body by detecting the positional information which has been transmitted from the position transmission device. In more detail, it performs positional detection while shifting within the living body after it has been orally ingested. On the other hand, the in-vivo information which has been transmitted from the transmission device is received by the reception device of the unit external to the living body and is sent to the specification device. The specification device, along with deciding that this is a hemorrhage, based upon the in-vivo information which has been sent from the reception device, when, for example, the amount of red color in the photographic image of the interior of the living body is greater than a threshold value, and specifying that this is a diseased part for which medication is required, also performs the specification of the moving distance to the position of that diseased part, based upon the position of the capsule for medication which has been detected by the position detection device.

After specification of the moving distance, the capsule for medication which has been orally ingested shifts within the living body while measuring the moving distance with the measurement device for medication. In detail, the decision device compares together the moving distance which has been measured with the moving distance which has been specified by the specification device, and if it decides that it is the specified moving distance, it notifies the control device to that effect. Upon receipt of this message, the control device causes the release device to operate, and releases the drug within the drug retention section.

Therefore, it is possible to release the drug at the position of the diseased part, and it is possible to administer the medication to the diseased part certainly and moreover directly. In particular, since along with the unit external to the living body performing the detection of the position of the capsule for observation, it also performs the specification of the moving distance, accordingly it is possible to make the capsule for observation of a simple structure, and it is possible to anticipate a further enhancement of the compactness.

With the capsule medication administration system according to the present invention, for example, the acquisition of surface information about the surface of the alimentary canal lumen wall such as convex shapes and concave shapes and the like is performed by forming images intermittently of the surface. The calculation device performs calculation of the moving distance, based upon the variation along with the passage of time of this surface information which has been acquired, in other words of these concave and convex shapes. By paying attention to the surface information about the alimentary canal lumen wall in this manner, it is possible to measure the moving distance easily and moreover reliably, and it is accordingly possible to enhance the accuracy of the medication for the diseased part.

With the capsule medication administration system according to the present invention, formation of images of the interior of the living body by the image formation device is performed more certainly by illuminating the living body with the illumination device it is possible to acquire photographic images which have been obtained by the observation device in this manner as in-vivo information.

With the capsule medication administration system according to the present invention, it is possible to acquire, as the in-vivo information, blood information such as the presence or absence, or the amount or the component or the like, of the blood within the living body which has been acquired by a blood sensor.

According to the capsule medication administration system of the present invention, since the release of the drug is performed when the capsule has shifted by just the specified moving distance which indicates the position of the diseased part, accordingly it is possible to administer the medication directly to the diseased part. At this time, since the medication is not administered from when the diseased part is detected, but, rather, the medication is performed based upon the moving distance, accordingly it is possible to administer the drug accurately, without the diseased part being passed over. In particular, since the capsule for medication itself decides whether or not it is the moving distance which has been specified and performs the medication, therefore it is possible to manage with a short time period for release of the drug from when the moving distance is measured, and it is possible to administer the medication to the diseased part with high accuracy.

Furthermore, the following concepts are included within the present invention:

(Supplementary Notes, Item 1)

A capsule medication administration system, characterized by including a capsule for medication which is orally ingested to within the living body and which includes an information transmission section which transmits its own positional information to outside the living body, and a unit external to the living body which includes a specification device which specifies a diseased part for which medication is required and the position of the diseased part; wherein:

the unit external to the living body includes an ex-body reception section which receives the positional information, a decision section which decides whether or not it has arrived at the diseased part from the positional information which has been received by the ex-body reception section and the positional information for the diseased part which has been specified by the specification device, and an ex-body transmission section which transmits a release signal towards the capsule for medication when the decision section has decided that the capsule for medication has arrived at the position of the diseased part; and the capsule for medication includes, within a capsule shaped casing, a drug retention section which retains a drug, a release section which releases a drug which has been retained in the drug retention section, a reception section which receives the release signal, and a control section which causes the release section to operate when the release signal has been received by the reception section.

With the capsule medication administration system according to this invention, the interior of the living body is diagnosed with a specification device such as an X-ray CT device or an endoscope device or the like, and the diseased part within the living body, and the position of the diseased part, are specified. After this specification, the capsule for medication which has been orally ingested to within the living body shifts within the living body while transmitting its own position information to the outside of the living body by the information transmission section transmitting electromagnetic waves or the like. This positional information is received by the ex-body reception section of the unit external to the living body, and is sent to the decision section. The decision section performs the decision that the capsule for medication has arrived at the position of the diseased part, when the positional information that has thus been sent, and the positional information for the diseased part that has been specified by the specification device agree with one another. Upon this decision, the ex-body transmission section transmits the release signal towards the capsule for medication. On the other hand, in the capsule for medication which is shifting within the living body, when the reception section receives this release signal, the control section causes the release section to operate, so as to release the drug which is being retained in the drug retention section to the exterior of the casing.

Therefore, the drug can be released at the position of the diseased part which has been specified by the specification device, and it is possible to administer the medication directly to the diseased part. In particular, since the positional information for the diseased part which has been specified by the specification device such as an X-ray CT device or the like, which is the actual result of diagnosis of the diseased part, is reflected by the capsule for medication, accordingly it is possible to administer accurate medication.

(Supplementary Notes, Item 2)

A capsule medication administration system as described in item 1 of these Supplementary, wherein:

the capsule for medication includes, within the casing, an observation section which acquires in-vivo information;

the ex-body transmission section is equipped with the function of, upon receipt of the decision result of the decision section, transmitting an in-vivo information acquisition signal towards the capsule for medication;

the reception section is equipped with the function of receiving the in-vivo information acquisition signal;

the control section is equipped with the function of causing the observation section to operate when it has received the in-vivo information acquisition signal from the reception section;

the information transmission section is equipped with the function of transmitting the in-vivo information which has been acquired by the observation section to outside the living body;

the ex-body reception section is equipped with the function of receiving the in-vivo information; and the decision section is equipped with the function of, along with deciding whether or not medication is to be performed based upon the in-vivo information which has been received by the ex-body reception section, also, when it has decided to perform medication, controlling the ex-body transmission section so as to transmit the release signal towards the capsule for medication.

With the capsule medication administration system according to this invention, when the decision section of the unit external to the living body decides that the capsule for medication has arrived at the position of the diseased part, the in-vivo information acquisition signal is transmitted towards the capsule for medication by the ex-body transmission section. When the capsule for medication, which is shifting within the living body, receives this in-vivo information acquisition signal from the reception section, the control section causes the observation section to operate. Upon receipt of this signal, the observation section acquires the in-vivo information, such as an image of the position of the diseased part, a pH value, a blood component, or the like. This in-vivo information which has been acquired is transmitted by the information transmission section to outside the living body. Furthermore, this in-vivo information which has been transmitted is received by the ex-body reception section of the unit external to the living body, and is sent to the decision section. The decision section decides whether or not the medication is required by comparing this in-vivo information which has been sent, for example, a threshold value which has been set in advance. When the result is that it has been decided that the medication is required, then a release signal is transmitted by the ex-body transmission section towards the capsule for medication. Upon receipt of this signal, the capsule for medication performs the release of the drug.

In this manner, since it is decided whether or not to perform the medication after the capsule has arrived at the position of the diseased part, and moreover based upon the in-vivo information at the position, therefore it is possible to decide reliable whether the diseased part which has been specified by the specification device has been reached, and to perform the medication. Accordingly, it is possible to enhance the reliability of administration of the medication.

(Supplementary Notes, Item 3)

A capsule medication administration system as described in item 1 or item 2 of these Supplementary, wherein:

the specification device is an endoscope device which includes an insertion section which, along with being inserted within the living body, also includes an image acquisition device at its tip end which forms an image of the interior of the living body; and, along with specifying the diseased part based upon an image which has been formed by the image acquisition device, also specifies the position of the diseased part based upon the insertion distance of the insertion section while the insertion section is inserted within the living body, and the image information due to the image acquisition device which corresponds thereto;

the capsule for medication includes, within the casing, an image formation section which forms images of the interior of the living body; and the information transmission section transmits, as its own the positional information, based upon the period of time that has elapsed from oral ingestion to within the living body, and the image information which has been imaged by the image formation section which corresponds thereto.

With the capsule medication administration system according to this invention, the insertion section is inserted within the living body, and specification of the diseased part is performed based upon the photographic images from the image acquisition device. At this time, the specification device performs the specification of the diseased part based upon the insertion distance of the insertion section within the living body, and upon the image information from the image acquisition device which corresponds thereto.

Furthermore, when the capsule for medication which has been orally ingested shifts within the living body, it shifts while forming images of the interior of the living body with the image formation section. Yet further, the information transmission section determines positional information for itself, based upon the time period which has elapsed from the oral ingestion of the capsule, and upon the image information which has been imaged by the image formation section which corresponds thereto, and transmits it to the exterior of the living body. It should be understood that brightness and/or color balance and the like are included in this image information. In other words, as position information for itself, there may be, for example, variation along with the passage of time of the brightness or of the color balance of the photographic images.

Furthermore, the decision section of the unit external to the living body compares together the positional information for the diseased part, in other words the variation of the image information which corresponds to the insertion distance of the insertion section, and the positional information for the capsule for medication, in other words the variation of the image information which corresponds to the passage of time from the oral ingestion of the capsule, and, when these two items of information agree with one another, decides that the capsule for medication has arrived at the position of the diseased part.

In this manner, by specifying the positional information for the diseased part which has been accurately specified by the endoscope device by the image information which corresponds to the insertion distance, and by moreover specifying the positional information for the capsule for medication by the image information which corresponds to the time period which has elapsed, it is possible easily to compare together these two items of information, and it is possible to administer the medication at the position of the diseased part which has been accurately specified by the endoscope device.

(Supplementary Notes, Item 4)

A capsule medication administration system as described in item 1 or item 2 of these Supplementary, wherein:

the specification device is an endoscope device which includes an insertion section which, along with being inserted within the living body, also includes an image acquisition device at its tip end which forms an image of the interior of the living body; and, along with specifying the diseased part based upon an image which has been formed by the image acquisition device, also specifies the position of the diseased part based upon the insertion distance of the insertion section while the insertion section is inserted within the living body, and the image information due to the image acquisition device which corresponds thereto;

the capsule for medication includes, within the casing, an image formation section which forms images of the interior of the living body, and a measurement section which measures the moving distance within the living body; and the information section transmits its own positional information, based upon the moving distance which has been measured by the measurement section, and the image information which has been imaged by the image formation section which corresponds thereto.

With the capsule medication administration system according to this invention, the insertion section is inserted within the living body, and specification of the diseased part is performed based upon the photographic images from the image acquisition device. At this time, the specification device performs the specification of the diseased part based upon the insertion distance of the insertion section within the living body, and upon the image information from the image acquisition device which corresponds thereto.

Furthermore, when the capsule for medication which has been orally ingested shifts within the living body, it shifts while measuring the moving distance within the living body with the measurement section. Yet further, the information transmission section determines positional information for itself, based upon the moving distance which has been measured by the measurement section, and upon the image information which has been imaged by the image formation section which corresponds thereto, and transmits it to the exterior of the living body.

Furthermore, the decision section of the unit external to the living body compares together the positional information for the diseased part, in other words the variation of the image information which corresponds to the insertion distance of the insertion section, and the positional information for the capsule for medication, in other words the variation of the image information which corresponds to the moving distance, and, when these two items of information agree with one another, decides that the capsule for medication has arrived at the position of the diseased part.

In this manner, by specifying the positional information for the diseased part which has been accurately specified by the endoscope device by the image information which corresponds to the insertion distance, and by moreover specifying the positional information for the capsule for medication by the image information which corresponds to the moving distance, it is possible easily to compare together these two items of information, and it is possible to administer the medication at the position of the diseased part which has been accurately specified by the endoscope device.

(Supplementary Notes, Item 5)

A capsule medication administration system includes, a capsule for medication which is orally ingested to within the living body, and a specification device which specifies a diseased part for which medication is required and the position of the diseased part; and the capsule for medication includes, within a capsule shaped casing, a drug retention section which retains a drug, a release section which releases the drug which is retained in the drug retention section, a memory which records the positional information for the diseased part which has been specified by the specification device, a detection section which detects its own position within the living body, a decision section which decides whether or not the capsule has arrived at the position of the diseased part from its own positional information which has been detected by the detection section and from the positional information for the diseased part which is recorded in the memory, and a control section which causes the release section to operate when the decision section has decided that the capsule has arrived at the position of the diseased part.

With the capsule medication administration system according to this invention, the inside of the living body is diagnosed by the specification device such as an X-ray CT device or an endoscope device or the like, and the diseased part within the living body and the position of the diseased part are specified. After this specification, the positional information for the diseased part is recorded in the memory of the capsule for medication. After this, while its own position is being detected by the detection section, the capsule for medication which has been orally ingested shifts within the living body while, for example, forming images of the interior of the living body, or while detecting variation of the pH value. Furthermore, the decision section decides whether or not the position of the diseased part has been arrived at, based upon the positional information for itself which has been detected by the detection section, and upon the positional information for the diseased part which is recorded in the memory. When it has been decided that the capsule has arrived at the position of the diseased part, the control section causes the release section to operate, so as to release the drug which is being retained in the drug retention section to the exterior of the casing.

Therefore, since the drug is released at the position of the diseased part which has been specified by the specification device, accordingly it is possible to apply the medication directly to the diseased part. At this time, since the positional information for the diseased part which has been specified by the specification device such as the X-ray CT device or the like, which is the actual result of diagnosis of the diseased part, is reflected in the capsule for medication, accordingly it is possible to perform accurate medication. Furthermore, since the capsule for medication itself performs the decision as to whether or not it has arrived at the position of the diseased part, accordingly it is possible to shorten the time period which is required for release of the drug from when it has detected its own position, and thus it is possible to apply the medication at the position of the diseased part with high accuracy.

(Supplementary Notes, Item 6)

A capsule medication administration system as described in item 5 of these Supplementary, wherein:

the specification device is an endoscope device which includes an insertion section which, along with being inserted within the living body, also includes an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto;

the capsule for medication includes, within the casing, an image formation section which forms images of the interior of the living body; and the detection section detects its own the positional information, based upon the period of time that has elapsed from oral ingestion to within the living body, and the image information which has been imaged by the image formation section which corresponds thereto.

With the capsule medication administration system according to this invention, along with performing insertion of the insertion section while forming images of the interior of the living body with the image acquisition device, the specification device performs the specification of the diseased part based upon the photographic images from the image acquisition device. At this time, the specification device performs the specification of the diseased part based upon the insertion distance of the insertion section within the living body, and upon the image information from the image acquisition device which corresponds thereto.

Furthermore, when the capsule for medication which has been orally ingested shifts within the living body, it shifts while forming images of the interior of the living body with the image formation section. Yet further, the detection section determines positional information for itself, based upon the time period which has elapsed from the oral ingestion of the capsule, and the image information which has been imaged by the image formation section which corresponds thereto, and compares together the positional information for itself, and the positional information for the diseased part, in other words the variation of the image information which corresponds to the insertion distance of the insertion section, and, when these two items of information agree with one another, decides that the capsule has arrived at the position of the diseased part. It should be understood that brightness and/or color balance and the like are included in this image information. In other words, as position information for itself, there may be, for example, variation along with the passage of time of the brightness or of the color balance of the photographic images.

In this manner, by specifying the positional information for the diseased part which has been accurately specified by the endoscope device by the image information which corresponds to the insertion distance, and by moreover specifying the positional information for the capsule for medication by the image information which corresponds to the time period which has elapsed, it is possible easily to compare together these two items of information, and it is possible to administer the medication at the position of the diseased part which has been accurately specified by the endoscope device.

(Supplementary Notes, Item 7)

A capsule medication administration system as described item 5 of these Supplementary, wherein:

the specification device is an endoscope device which includes an insertion section which, along with being inserted within the living body, also includes an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto;

the capsule for medication includes, within the casing, an image formation section which forms images of the interior of the living body, and a measurement section which measures the moving distance within the living body; and the detection section detects its own the positional information, based upon the moving distance which has been measured by the measurement section, and the image information which has been imaged by the image formation section which corresponds thereto.

With the capsule medication administration system according to this invention, along with performing insertion of the insertion section while forming images of the interior of the living body with the image acquisition device, the specification device performs the specification of the diseased part based upon the photographic images from the image acquisition device. At this time, the specification device performs the specification of the diseased part based upon the insertion distance of the insertion section within the living body, and upon the image information from the image acquisition device which corresponds thereto.

Furthermore, when the capsule for medication which has been orally ingested shifts within the living body, it shifts while measuring the moving distance within the living body with the measurement section. Yet further, the detection section determines positional information for itself, based upon the moving distance which has been measured by the measurement section, and the image information which has been imaged by the image formation section which corresponds thereto, and compares together the positional information for itself, and the positional information for the diseased part, in other words the variation of the image information which corresponds to the insertion distance of the insertion section, and, when these two items of information agree with one another, decides that the capsule has arrived at the position of the diseased part.

In this manner, by specifying the positional information for the diseased part which has been accurately specified by the endoscope device by the image information which corresponds to the insertion distance, and by moreover specifying the positional information for the capsule for medication by the image information which corresponds to the moving distance, it is possible easily to compare together these two items of information, and it is possible to administer the medication at the position of the diseased part which has been accurately specified by the endoscope device.

(Supplementary Notes, Item 8)

A capsule medication administration system as described in any one of items 5 through 7 of these Supplementary, wherein:

the capsule for medication includes, within the casing, a sensor which, while shifting within the living body, measures the hardness of the living tissue with which it is in contact; and the decision section, in addition to its the own positional information and the positional information for the diseased part, also makes its decision as to whether or not it has arrived at the position of the diseased part, based upon the hardness of the living tissue which has been measured.

With the capsule medication administration system according to this invention, while shifting within the living body, the sensor, for example, shifts while performing measurement of the hardness within his alimentary canal. The decision section, in addition to its the own positional information and the positional information for the diseased part, also makes its decision as to whether or not it has arrived at the position of the diseased part by comparing together the hardness which has been measured by the sensor and a threshold value, based upon the hardness of the living tissue which has been measured, or the like. Accordingly, it is possible to detect when the capsule has arrived at the diseased part more accurately.

(Supplementary Notes, Item 9)

A capsule medication administration system including, a capsule for medication which is orally ingested to within the living body, and a specification device which specifies a diseased part for which medication is required and the position of the diseased part; and wherein:

the specification device includes a marking device which makes a mark at the position of the diseased part which has been specified; and the capsule for medication includes, within a capsule shaped casing, a drug retention section which retains a drug, a release section which releases the drug which has been retained in the drug retention section, a marker detection section which detects the marker, and a control section which causes the release section to operate when the marker has been detected by the marker detection section.

With the capsule medication administration system according to this invention, the interior of the living body is diagnosed with the specification device such as an X-ray CT device or an endoscope device or the like, and the diseased part within the living body and the position of the diseased part are specified. After this specification, the marking device makes a marker at the position of the diseased part from within the living body, or from outside his body. After this, while the capsule for medication which has been orally ingested is shifting within the living body, when the marker detection section detects the marker which has been made by the marking device, the control section causes the release section to operate, and thereby releases the drug which is being retained in the drug retention section to the exterior of the casing.

Therefore, it is possible to release the drug at the position of the diseased part which has been specified by the specification device, so that it is possible to administer the medication directly to the diseased part. In particular, since it is possible to reflect the positional information for the diseased part which has been specified by the specification device such as an X-ray CT device or the like, which is the actual result of diagnosis of the diseased part, by the capsule for medication via the marker, accordingly it is possible to perform accurate medication. Furthermore, since the detection of the position of the diseased part is performed just by providing the marker detection section, accordingly it is possible to make the capsule for medication of a simple structure, so that it is possible to anticipate an enhancement of its compactness.

(Supplementary Notes, Item 10)

A capsule medication administration system as described in item 9 of these Supplementary, wherein:

the specification device is an endoscope device which includes an insertion section which is inserted within the living body; and the marking device makes the marker at the diseased part by using a tip end section of the insertion section.

With the capsule medication administration system according to this invention, the marker is made at the position of the diseased part using the tip end of the insertion section, by, for example, attaching a clip, adhering a fluorescent substance, or scattering a colored element. Therefore, it is possible for the capsule for medication which is shifting within the living body to detect the marker easily and moreover directly, and it is possible to administer the medication reliably to the diseased part.

(Supplementary Notes, Item 11)

A capsule medication administration system as described in item 9 of these Supplementary, wherein:

the marking device is an emission device which emits an ultrasonic wave or an electromagnetic wave at the diseased part which passes through the living body and has directivity from outside the living body towards the interior thereof; and the marker detection section detects the ultrasonic wave or the electromagnetic wave.

With the capsule medication administration system according to this invention, the emission device emits the ultrasonic wave or the electromagnetic wave from outside the living body towards the position of the diseased part which has been specified. At this time, since the ultrasonic wave or the electromagnetic wave passes through the living body and is equipped with directivity, accordingly it is possible to indicate the position to the diseased part accurately from outside the living body. Due to this, it is possible for the capsule for medication which is shifting within the living body to detect the marker easily and moreover directly, and thus it is possible to administer the medication reliably at the position of the diseased part.

(Supplementary Notes, Item 12)

A capsule for medication including:

within a capsule shaped casing which is orally ingested to within the living body, a drug retention section which retains a drug;

a release device which releases the drug which has been retained in the drug retention section;

a release control device which causes the operation of the release device; and a detection device which detects an indicator which indicates a drug release position;

wherein the release control device causes the operation of the release device, based upon the output of the detection device.

(Supplementary Notes, Item 13)

A capsule for medication as described in item 12 of these Supplementary, wherein the indicator is a specified marking which is made within the living body.

(Supplementary Notes, Item 14)

A capsule for medication as described in item 13 of these Supplementary, wherein:

the detection device is one which detects a plurality of markings which have been made within the living body; and in that:

the release control device includes a memory which stores in advance the specified marking as the number of the marking, and, by counting the markings which have been detected by the detection device, causes the operation of the release device when this count agrees with the number which is stored in the memory (Supplementary Notes, Item 15)

A capsule type medical device including:

a capsule type casing which is orally ingested to within the living body;

an in-vivo information acquisition device, which acquires in-vivo information;

a marking device which leaves an indicator within the coelom; and a transmission device which transmits to the exterior of the casing the in-vivo information which has been acquired by the in-vivo information acquisition device, and the indicator which has been left within the coelom by the marking device.

(Supplementary Notes, item 16)

A capsule type medical device as described in item 15 of these Supplementary, further including an information processing section which establishes a correspondence between the in-vivo information which has been acquired by the in-vivo information acquisition device, and the information about the indicator which has been left within the coelom by the marking device.

(Supplementary Notes, Item 17)

A capsule type medical device as described in item 16 of these Supplementary, further including a storage device which stores information which has been processed by the information processing system.

(Supplementary Notes, Item 18)

A capsule type medical device as described in any one of items 14 through 17 of these Supplementary, wherein the marking device performs intermittent movement.

(Supplementary Notes, Item 19)

A capsule type medical device as described in item 15 of these Supplementary, wherein the indicator includes at least one of a magnetic material, a fluorescent chemical, a dye, a radioactive isotope, or a metallic material.

(Supplementary Notes, Item 20)

A capsule type medical device system, including:

a medical device which includes an in-vivo information acquisition device which obtains in-vivo information within his coelom, and a marking device which leaves an indicator within the coelom; and a capsule type medical device which includes a capsule shaped sheathing section, an indicator detection device which detects an indicator which has been left by the medical device within the coelom, a drug storage section, a drug release section which releases a drug within the drug storage section, and a control section which controls the drug release section based upon the information from the indicator detection device.

(Supplementary Notes, Item 21)
A capsule type medical device system as described in item 20 of these Supplementary, wherein the medical device is an endoscope.

(Supplementary Notes, Item 22)
A capsule type medical device system as described in item 21 of these Supplementary, wherein the marking device is a clip for an endoscope.

(Supplementary Notes, Item 23)
A capsule type medical device system as described in item 20 of these Supplementary, wherein:
the medical device includes: a second capsule type medical system which includes a capsule shaped sheathing section, the in-vivo information acquisition device, the marking device, and an information transmission section which transmits to the exterior of the sheathing section the in-vivo information which has been detected by the in-vivo information acquisition device, and the operation information of the marking device;
and a reception device which receives information which has been transmitted to the exterior of the sheathing section by the information transmission section.

(Supplementary Notes, Item 24)
A capsule type medical device system as described in item 23 of these Supplementary, wherein:
the second capsule type medical device includes a storage device which stores the in-vivo information which has been detected by the in-vivo information acquisition device, and the operation information for the marking device, with a correspondence established between them; and
the information transmission section transmits the information which is stored in the storage device to the exterior of the sheathing section.

(Supplementary Notes, Item 25)
A capsule type medical device system as described in item 23 or 24 of these Supplementary, wherein the information transmission section includes an infrared communication device.

(Supplementary Notes, Item 26)
A capsule type medical device system as described in item 23 or 24 of these Supplementary, wherein the information transmission section includes a communication device by electromagnetic waves.

(Supplementary Notes, Item 27)
A capsule type medical device system as described in any one of items 23 through 25 of these Supplementary, wherein the second capsule type medical device leaves indicators intermittently.

(Supplementary Notes, Item 28)
A capsule type medical device system as described in item 20 of these Supplementary, wherein the marking device leaves indicators intermittently.

(Supplementary Notes, Item 29)
A capsule type medical device system as described in item 28 of these Supplementary, wherein the marking device leaves indicators at fixed time intervals.

(Supplementary Notes, Item 30)
A capsule type medical device system as described in item 28 of these Supplementary, further including a position detection device, and in that the marking device leaves an indicator based upon position information which has been detected by the position detection device.

(Supplementary Notes, Item 31)
A capsule type medical device system as described in item 28 of these Supplementary, wherein the second capsule type medical device includes a shift amount detection device, and in that the marking device leaves an indicator based upon the output of the shift amount detection device.

(Supplementary Notes, Item 32)
A capsule type medical device system as described in any one of items 28 through 31 of these Supplementary, wherein the indicator is a drug of low reflectivity ratio with respect to the living tissue within the coelom.

(Supplementary Notes, Item 33)
A capsule type medical device system as described in any one of items 28 through 31 of these Supplementary, wherein the indicator is a drug of high reflectivity ratio with respect to the living tissue within the coelom.

(Supplementary Notes, Item 34)
A capsule type medical device system as described in any one of items 28 through 31 of these Supplementary, wherein the indicator is a magnetic material.

(Supplementary Notes, Item 35)
A capsule type medical device system as described in any one of items 28 through 31 of these Supplementary, wherein the indicator is a fluorescent material.

(Supplementary Notes, Item 36)
A control method including:
a step of observing the interior of the living body;
a step of determining a medication position within the living body;
a step of appending an indicator near the medication position;
a step of inserting within the coelom a capsule for medication which includes a device for detecting the indicator, a drug retention section, a drug release section, and a release control device;
a step of detecting the indicator; and
a step of performing control of the drug release section.

(Supplementary Notes, Item 37)
A control method including:
a step of observing the interior of the living body;
a step of leaving an indicator within the living body;
a step of establishing a correspondence between in-vivo information which has been obtained by the step of obtaining in-vivo information, and the fact that the step of leaving an indicator within the living body has been performed, and recording the same as in-vivo information;
a step of determining a medication position from the in-vivo information;
a step of setting the medication position into a capsule for medication which includes a device for detecting the indicator, a drug retention section, a drug release section, and a release control device;
a step of inserting the capsule for medication within the coelom;
a step of detecting the indicator;
a step of detecting the medication position; and
a step of performing control of the drug release section.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A capsule medication administration system, comprising:
   a capsule type medical device which includes a drug retention section, a drug release section which releases a drug which is retained in the drug retention section, a communication section which performs signal sending and reception to and from the outside, and an observation section which acquires a photographic image of the body;
   a specification device which specifies a diseased body part based on an observation from outside of the body; and
   an external device which comprises an external communication section which performs signal sending and reception to and from the capsule type medical device;
   wherein the capsule medication system further comprises:
   a condition input section which inputs position information which are conditions for causing the operation of the drug release section to the external device;
   an information acquisition section which acquires position information for comparison with conditions which have been inputted by the condition input section; and
   a comparison section which compares together the position information which has been acquired by the information acquisition section and the position information which have been inputted with the condition input section;
   a medication position specification device which supplies data for deciding upon a site for which medication is required is connected to the condition input section; and
   a decision section which forms an image of the diseased body part by using the observation section of the capsule type medical device when the result of comparison by the comparison section fits and decides whether there is a diseased body part for which medication is required based on the image; and
   a control section which control the drug release section so that releasing the drug when the decision section decides that there is a diseased body part for which medication is required.

2. A capsule medication administration system as claimed in claim 1, wherein the comparison section is provided to the external device.

3. A capsule medication administration system as claimed in claim 2, wherein:
   the capsule type medical device comprises, within a casing, an observation section which acquires in-vivo information, and a control section which causes the observation section to operate when an in-vivo information acquisition signal has been received by the communication section;
   the external communication section is equipped with the function of transmitting the in-vivo information acquisition signal towards the capsule type medical device, based upon the comparison decision result of the comparison section;
   the communication section is equipped with the function of receiving the in-vivo information acquisition signal;
   the communication section is equipped with the function of transmitting the in-vivo information which has been acquired by the observation section;
   the external communication section is equipped with the function of receiving the in-vivo information; and
   the comparison section is equipped with the function of, along with deciding whether or not to administer medication based upon the in-vivo information which has been received by the external communication section, also, when it has decided to administer medication, controlling the external communication section so as to transmit a release signal towards the capsule type medical device.

4. A capsule medication administration system as claimed in claim 2, wherein:
   the medication position specification device is an endoscope device which comprises an insertion section which, along with being inserted within the living body, also comprises an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto;
   the information acquisition section of the capsule type medical device comprises an image formation section which forms images of the interior of the living body; and
   the communication section transmits the positional information itself, based upon the period of time that has elapsed from oral ingestion to within the living body, and the image information which has been imaged by the image formation section which corresponds thereto.

5. A capsule medication system as claimed in claim 4, wherein:
   the information acquisition section of the capsule type medical device comprises a measurement section which measures the moving distance within the living body.

6. A capsule medication administration system as claimed in claim 1, wherein the comparison section is provided to the capsule type medical device.

7. A capsule medication administration system as claimed in claim 1, wherein:
   the specification device is an endoscope device which comprises an insertion section which, along with being inserted within the living body, also comprises an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto;
   the information acquisition section of the capsule type medical device comprises an image formation section which forms images of the interior of the living body; and a detection section which detects its own the positional information, based upon the period of time that has elapsed from oral ingestion to within the living body, and the image information which has been imaged by the image formation section which corresponds thereto.

8. A capsule medication administration system as claimed in claim 6, wherein:
   the specification device is an endoscope device which comprises an insertion section which, along with being inserted within the living body, also comprises an image acquisition device at its tip end which forms an image of the interior of the living body; and, along with specifying a diseased part based upon an image which has been formed by the image acquisition device, also specifies the position of the diseased part based upon the insertion distance of the insertion section while the insertion section is inserted within the living body, and the image information due to the image acquisition device which corresponds thereto;

the information acquisition section of the capsule type medical device comprises an image formation section which forms images of the interior of the living body, and a measurement section which measures the moving distance within the living body; and a detection section which detects its own the positional information, based upon the moving distance which has been measured by the measurement section, and the image information which has been imaged by the image formation section which corresponds thereto.

9. A capsule medication administration system as claimed in claim 6, wherein:

the information acquisition section of the capsule type medical device comprises a sensor which, while moving within the living body, measures the hardness of the living tissue with which it is in contact; and the comparison section, in addition to its own positional information and positional information for the diseased part, also makes its decision by comparing whether or not it has arrived at the position of the diseased part, based upon the hardness of the living tissue which has been measured by the sensor.

10. A capsule medication administration system as claimed in claim 1, comprising:

the capsule type medical device which is orally ingested within the living body, and a specification device which specifies a diseased part for which medication is required and the position of the diseased part;

the specification device comprises a marking device which makes a mark at the position of the diseased part which has been specified, the information acquisition section of the capsule type medical device comprises a marker detection section which detects the marker, and a release control device which causes the drug release section to operate when the marker has been detected by the marker detection section.

11. A capsule medication administration system as claimed in claim 10, wherein:

the specification device is an endoscope device which comprises an insertion section which is inserted within the living body; and the marking device makes the marker at the diseased part by using a tip end section of the insertion section.

12. A capsule medication administration system as claimed in claim 10, wherein:

the marking device is an emission device which emits an ultrasonic wave or an electromagnetic wave at the diseased part which passes through the living body and has directivity from outside the living body towards the interior thereof; and the marker detection section detects the ultrasonic wave or the electromagnetic wave.

13. A capsule medication administration system as claimed in claim 1, further comprising a traversed distance calculation device which obtains the distance traversed within the lumen from the information of the medication position specification device, and the information acquisition section is a moving distance detection device.

14. A capsule medication administration system as claimed in claim 1, wherein the condition input section simplifies or approximates the information from the medication position specification device.

15. A capsule medication administration system as claimed in claim 1, wherein the medication position specification device comprises an external in-vivo information acquisition device which acquires an in-vivo information from outside living body.

16. A capsule medication administration system as claimed in claim 15, wherein the medical position specification device comprises an external marker to the living body for detecting the relative position of the site within the living body and the site external to the living body.

17. A capsule medication administration system as claimed in claim 15, wherein the external in-vivo information acquisition device is a transilluminated image acquisition device which acquires a transilluminated image of the interior of the living body from outside the living body.

18. A capsule medication administration system as claimed in claim 17, wherein the transilluminated image acquisition device is an X-ray device.

19. A capsule medication administration system as claimed in claim 17, wherein the transilluminated image acquisition device is a PET device.

20. A capsule medication administration system as claimed in claim 15, wherein the external in-vivo information acquisition device is a tomographic image acquisition device which acquires a tomographic image of the interior of the living body from outside the living body.

21. A capsule medication administration system as claimed in claim 20, wherein the tomographic image acquisition device is capable of acquiring a three dimensional image of the interior of the living body based upon a plurality of tomographic images.

22. A capsule medication administration system as claimed in claim 20, wherein the tomographic image acquisition device is a CT device.

23. A capsule medication administration system as claimed in claim 20, wherein the tomographic image acquisition device is an MRI device.

24. A capsule medication administration system as claimed in claim 20, wherein the tomographic image acquisition device is an ultrasonic tomographic device.

25. A capsule medication administration system as claimed in claim 1, wherein the medication position specification device has an in-body insertion section which is inserted into the living body.

26. A capsule medication administration system as claimed in claim 25, wherein the in-body insertion section comprises an in-body indicator device which places an indicator within the living body.

27. A capsule medication administration system as claimed in claim 26, wherein the in-body indicator device is an indicator liquid indwell device which discharges or injects an indicator liquid which becomes an indicator in the living body.

28. A capsule medication administration system as claimed in claim 27, wherein the indicator liquid is a dye or a fluorescent dye.

29. A capsule medication administration system as claimed in claim 27, wherein the indicator liquid is a radioactive substance or a magnetic substance.

30. A capsule medication administration system as claimed in claim 26, wherein the indicator is an indicator which has the difference of reflectivity ratio with respect to living tissue within the coelom.

31. A capsule medication administration system as claimed in claim 25, wherein the medication position specification device is an endoscope device which has an in-body insertion section.

32. A capsule medication administration system as claimed in claim 31, wherein the endoscope device comprises an insertion amount detection section which detects the insertion distance of the in-body insertion section to within the living body.

33. A capsule medication administration system as claimed in claim 31, wherein the endoscope device comprises an in-body indicator device which places an indicator within the living body, and the indicator is a clip or a stent made from metal.

34. A capsule medication administration system as claimed in claim 25, wherein the in-body insertion section is a capsule type medical device for acquiring in-vivo information, which comprises an in-vivo information acquisition device which acquires information about the interior of the living body.

35. A capsule medication administration system as claimed in claim 34, wherein the capsule type medical device for acquiring in-vivo information comprises a moving distance calculation device which calculates the moving distance, based upon the variation along with the passage of time of the surface information of the living body lumen wall which has been acquired by the in-vivo information acquisition device.

36. A capsule medication administration system as claimed in claim 34, wherein the capsule type medical device for acquiring in-vivo information comprises, within a capsule shaped casing, a measurement device for observation which measures the moving distance within the living body, a memory which records the moving distance which has been measured by the measurement device for observation and the in-vivo information which has been acquired by the in-vivo information acquisition device with a correspondence being established between them, and a specification device which specifies the body part for which medication is required and the moving distance to the diseased part, based upon the in-vivo information which has been recorded in the memory; and the capsule type medical device for medication which is equipped with the drug retention section and the drug release section comprises, within a capsule shaped casing, a measurement device for medication which measures the moving distance within the living body, a decision device which decides whether or not the moving distance which has been measured by the measurement device for medication is the moving distance which has been specified by the specification device, and a control device which causes the drug release section to operate, when the decision device has decided that it is the moving distance which has been specified.

37. A capsule medication administration system as claimed in claim 34, wherein the capsule type medical device for acquiring in-vivo information comprises, within a capsule shaped casing, a measurement device for observation which measures the moving distance within the living body, and a transmission device which transmits the moving distance which has been measured by the measurement device for observation and the in-vivo information which has been acquired by the in-vivo information acquisition device towards the external device with a correspondence being established between them;

the external device comprises a specification device which acquires in-vivo information by the exterior communication device, and specifies the diseased part for which medication is required, and the moving distance to the diseased part, based upon the in-vivo information which has been received; and the capsule type medical device for medication which is equipped with the drug retention section and the drug release section comprises, within a capsule shaped casing, a measurement device for medication which measures the moving distance within the living body, a decision device which decides whether or not the moving distance which has been measured by the measurement device for medication is the moving distance which has been specified by the specification device, and a control device which causes the drug release section to operate, when the decision device has decided that it is the moving distance which has been specified.

38. A capsule medication administration system as claimed in claim 34, wherein the capsule type medical device for acquiring in-vivo information comprises, within a capsule shaped casing, a position transmission device which transmits positional information for itself to outside the living body;

the external device comprises a position detection device which detects the position information which has been transmitted by the position communication device, a specification device which specifies the diseased part for which medication is required, the moving distance to the diseased part, based upon the in-vivo information which has been received by the external communication section, and the positional information which has been detected by the position detection device; and the capsule type medical device for medication which is equipped with the drug retention section and the drug release section comprises, within a capsule shaped casing, a measurement device for medication which measures the moving distance within the living body, a decision device which decides whether or not the moving distance which has been measured by the measurement device for medication is the moving distance which has been specified by the specification device, and a control device which causes the drug release section to operate, when the decision device has decided that it is the moving distance which has been specified.

39. A capsule medication administration system as claimed in claim 34, wherein the capsule type medical device for acquiring in-vivo information comprises a measurement device for observation which measures the moving distance within the living body.

40. A capsule medication administration system as claimed in claim 34, wherein the capsule type medical device for acquiring in-vivo information comprises, as the in-vivo information acquisition device, an image formation device which forms an image of the interior of the living body, and an illumination device which illuminates the interior of the living body.

41. A capsule medication administration system as claimed in claim 34, wherein the capsule type medical device for acquiring in-vivo information comprises, as the in-vivo information acquisition device, a blood sensor which detects hemorrhage within the living body.

42. A capsule medication administration system as claimed in claim 34, wherein the capsule type medical device for acquiring in-vivo information comprises an in-body indicator device which places an indicator within the living body.

43. A capsule medication administration system as claimed in claim 42, wherein the in-body indicator device places the indicator within the living body intermittently.

44. A capsule medication administration system as claimed in claim 43, wherein the in-body indicator device discharges or injects the indicator at constant time intervals.

45. A capsule medication administration system as claimed in claim 43, wherein the in-body indicator device discharges or injects the indicator at constant distance intervals.

46. A capsule medication administration system as claimed in claim 42, comprising a capsule type medical device which comprises an indicator detection device which detects an indicator which is left within the coelom, and a release control device which controls the drug release section based upon the information of the indicator detection device.

47. A capsule medication administration system as claimed in claim 42, wherein the capsule type medical device for acquiring in-vivo information comprises an external communication section which transmits to the exterior the in-vivo information which has been acquired by the in-vivo information acquisition device, and movement information of the in-body indicator device;
- wherein the capsule medication administration system comprises an external device which receives the information which has been transmitted to the exterior by the external communication section.

48. A capsule medication administration system comprising:
- within a capsule shaped casing which is orally ingested to within the living body, a drug retention section which retains a drug;
- a drug release section which releases the drug which has been retained in the drug retention section;
- a release control device which causes the operation of the drug release section; and
- an indicator detection device which detects an indicator which indicates a drug release position; wherein
- the indicator detection device is a device which detects a plurality of markings which have been made within the living body;
- the release control device comprises a memory which stores the specified marking in advance as a marking number; and
- the release device is caused to operate by counting the markings which have been detected by the detection device, when this count agrees with the number which is stored in the memory.

49. A capsule medication administration system as claimed in claim 42, comprising:
- a capsule shaped casing which is orally ingested within the living body;
- a transmission device which transmits the in-vivo information which has been acquired by the in-vivo information acquisition device and the indicator which has been left within the coelom by the in-body indicator device to the exterior of the casing; and
- an information processing section which establishes a correspondence between the in-vivo information which has been acquired by the in-vivo information acquisition device and information about the indicator which has been left within the living body by the marking device.

50. A capsule medication administration system as claimed in claim 49, comprising a storage device which stores information which has been processed by the information processing section.

51. A capsule medication system comprising:
- an acquisition means for acquiring information about a body which obtains information about the body within a coelom and a medical device that includes a marking means which is able to put a marking at a different position of the coelom by leaving a plurality of indicators intermittently within the coelom;
- a capsule type medical device that includes a capsule shaped sheathing section, an indicator detection means which detects an indicator which has been left by said medical device within the coelom, a drug storage section, a drug release section which releases a drug within said drug storage section, and a control section which controls the drug release section based upon the information from said indicator detection means;
- wherein the control section that stores in advance a specified indicator which is an indicator out of the plurality of indicators which a drug release section needs to release a drug as the number of indicator and causes the drug release section to operate when the number of indicator which is informed from the indicator detection means agrees with the number which is stored in the control section.

52. A capsule medication system as described in claim 51, wherein the medical device further comprises a storage means which stores the information about the body and a position at which the marking is put, with a correspondence established between them.

\* \* \* \* \*